(12) United States Patent
Pleguezuelos Mateo et al.

(10) Patent No.: US 10,973,897 B2
(45) Date of Patent: Apr. 13, 2021

(54) CHAGAS ANTIGENS AND ANTIBODIES AND COMPOSITIONS, METHODS AND USES THEREOF

(71) Applicant: PepTcell Limited, London (GB)

(72) Inventors: Olga Pleguezuelos Mateo, Bicester (GB); Wilson Caparros-Wanderley, Buckinghamshire (GB); Gregory A. Stoloff, London (GB)

(73) Assignee: PepTcell Limited, London (GB)

( * ) Notice: Subject to any disclaimer, the term of this patent is extended or adjusted under 35 U.S.C. 154(b) by 184 days.

(21) Appl. No.: 15/487,935

(22) Filed: Apr. 14, 2017

(65) Prior Publication Data

US 2017/0296637 A1 Oct. 19, 2017

Related U.S. Application Data

(60) Provisional application No. 62/322,770, filed on Apr. 14, 2016.

(51) Int. Cl.
*A61K 39/005* (2006.01)
*C07K 14/44* (2006.01)
*A61K 39/00* (2006.01)

(52) U.S. Cl.
CPC ............ *A61K 39/005* (2013.01); *C07K 14/44* (2013.01); *A61K 2039/545* (2013.01); *A61K 2039/55566* (2013.01); *A61K 2039/57* (2013.01); *A61K 2039/575* (2013.01); *Y02A 50/30* (2018.01)

(58) Field of Classification Search
None
See application file for complete search history.

(56) References Cited

FOREIGN PATENT DOCUMENTS

| EP | 1279679 A1 | 1/2003 | |
|---|---|---|---|
| WO | WO-2011058137 A1 * | 5/2011 | ............ C07K 14/44 |
| WO | 2015001383 A1 | 1/2015 | |
| WO | 2015048072 A2 | 4/2015 | |

OTHER PUBLICATIONS

Schijnnan et al. (Nucleic Acids Research vol. 18 pp. 3399-3399).*
Dumonteil, et al., Accelerating the development of a therapeutic vaccine for human Chagas disease: rationale and prospects, Expert Rev Vaccines. 11(9): 1043-1055 (2012).
Eickhoff, et al., An immunoinformatic approach for identification of Trypanosoma cruzi HLA-A2-restricted CD8C T cell epitopes, Hum. Vaccines Immunother. 11(9): 2322-2328 (2015).
Sema, et al., A synthetic peptide from Trypanosoma cruzi mucin-like associated surface protein as candidate for a vaccine against Chagas disease, Vaccine 32: 3525-3532 (2014).
Teh-Poot, From Genome Screening to Creation of Vaccine Against Trypanosoma cruzi by Use of Immunoinformatics, J. Infect. Dis. 211: 258-266 (2015).
WIPO, PCT Form ISA 210, International Search Report for PCT/EP2017/059189, pp. 9 (dated Sep. 5, 2017).
WIPO, PCT Form ISA 237, Written Opinion for PCT/EP2017/059189, pp. 11 (dated Sep. 5, 2017).
WIPO, PCT Form IB 373, International Preliminary Report on Patentability for PCT/EP2017/059189, pp. 11 (dated Oct. 26, 2018).

* cited by examiner

*Primary Examiner* — Robert A Zeman
(74) *Attorney, Agent, or Firm* — UltimatEdge IP Law Group, P.C.; Dean G. Stathakis

(57) ABSTRACT

The present specification discloses *Trypanosoma* antigens, immunogenic compositions and medicaments comprising such *Trypanosoma* antigens, methods and uses for such *Trypanosoma* antigens and immunogenic compositions for treating a *Trypanosoma*-based disease.

14 Claims, 12 Drawing Sheets

Specification includes a Sequence Listing.

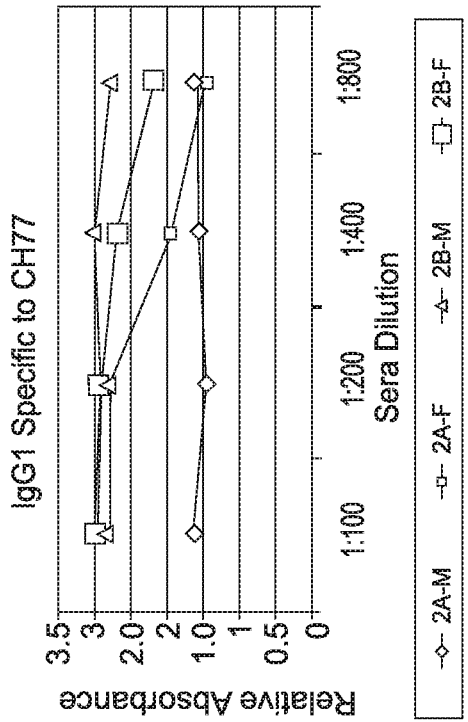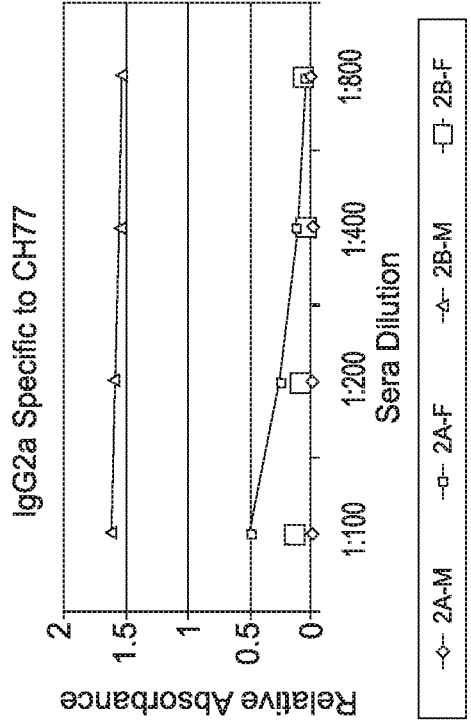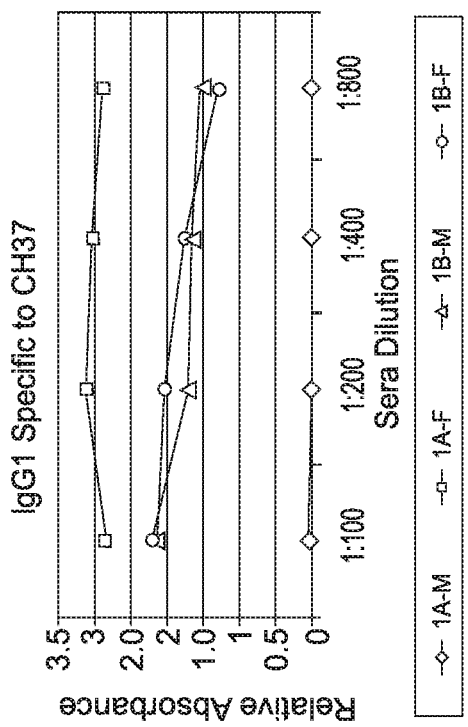
*Fig. 8A*
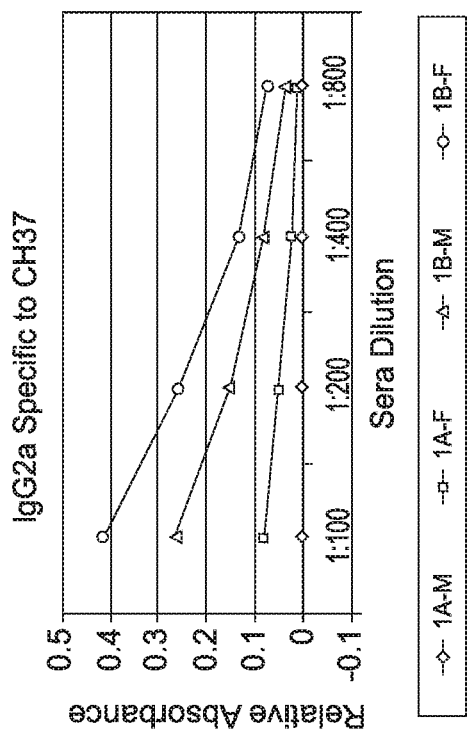

GROUP A (control) n=6

GROUP B (immunization with CHv) n=12

GROUP C (control) n=6

GROUP D (immunization with CHv and CH-v+CH47) n=12

GROUP A (peptide 47) n=12

Days 47                              47                         Challenge

GROUP B (immunization with CHv and (CH-v/CH47) n=12

Days

CHv                    CH-v+CH47              Challenge

GROUP C (control) n=12

Days

Adjuvant                 Adjuvant                 Challenge ly found in the amastigote form. The trypomastigote morphology is unique to species in the genus *Trypanosoma*.

CHAGAS ANTIGENS AND ANTIBODIES AND COMPOSITIONS, METHODS AND USES THEREOF

This application claims the benefit of priority and the filing date of U.S. Provisional Patent Application 62/322,770, filed on Apr. 14, 2016, the contents of which are hereby incorporated by reference in its entirety.

*Trypanosoma* is a genus of kinetoplastids (class Kinetoplastida), a monophyletic group of unicellular parasitic flagellate protozoa. Most trypanosomes are heteroxenous (requiring more than one obligatory host to complete life cycle) and most are transmitted via a vector. The majority of species are transmitted by blood-feeding invertebrates, but there are different mechanisms among the varying species. In an invertebrate host they are generally found in the intestine, but normally occupy the bloodstream or an intracellular environment in the mammalian host.

Two different types of trypanosomes exist, and their life cycles are different, the stercorarian species and the salivarian species. Stercorarian trypanosomes infect the insect, most often the triatomid kissing bug, develop in its posterior gut and infective organisms are released in the feces and deposited on the skin of the host. The organism then penetrates and can disseminate throughout the body. Insects become infected when taking a blood meal. Salivarian trypanosomes develop in the anterior gut of insects, most importantly the Tsetse fly, and infective organisms are inoculated into the host by the insect bite before it feeds. As trypanosomes progress through their life cycle they undergo a series of morphological changes as is typical of trypanosomatids. The life cycle often consists of the trypomastigote form in the vertebrate host and the trypomastigote or promastigote form in the gut of the invertebrate host. Intracellular lifecycle stages are normally found in the amastigote form. The trypomastigote morphology is unique to species in the genus *Trypanosoma*.

Trypanosomes infect a variety of hosts and cause various diseases, including the fatal human diseases Chagas disease, caused by *Trypanosoma cruzi* and African sleeping sickness, caused by *T. brucei*.

For many years *Trypanosoma*-based infections were not a condition susceptible of treatment. Disclosed herein are *Trypanosoma* antigens, immunogenic compositions and antibodies that induces immune responses effective in protecting against one or more *Trypanosoma* strains.

SUMMARY

Thus, aspects disclosed in the present specification provide *Trypanosoma* antigens. A *Trypanosoma* antigen disclosed herein may trigger an immune response that produce an α-*Trypanosoma* antibody capable of binding an epitope present on the surface of a *Trypanosoma*-infected cell.

Other aspects disclosed in the present specification provide immunogenic compositions comprising one or more *Trypanosoma* antigens disclosed herein. Compositions can further comprise an adjuvant.

Other aspects disclosed in the present specification provide methods of treating an individual infected with a *Trypanosoma* pathogen or having a *Trypanosoma*-based disease. The disclosed methods comprise administering a *Trypanosoma* antigen or immunogenic composition disclosed herein to an individual infected with a *Trypanosoma* pathogen or having a *Trypanosoma*-based disease.

Other aspects disclosed in the present specification provide use of a *Trypanosoma* antigen or immunogenic composition disclosed herein for the manufacture of a medicament.

Other aspects disclosed in the present specification provide use of a *Trypanosoma* antigen or immunogenic composition disclosed herein for treatment of an individual infected with a *Trypanosoma* pathogen.

Other aspects disclosed in the present specification provide a *Trypanosoma* antigen or immunogenic composition disclosed herein for use in the treatment of an individual infected with a *Trypanosoma* pathogen.

BRIEF DESCRIPTION OF THE DRAWINGS

FIG. 1B showing IL-4 production in Group B animals; FIG. 1C showing IFN-γ production in Group A animals; and FIG. 1D showing IFN-γ production in Group B animals.

FIG. 2B showing total immunoglobulin responses in female animals.

FIG. 3B showing IgG2 responses in female animals; FIG. 3C showing IgG1 responses in male animals; and FIG. 3D showing IgG1 responses in female animals.

FIG. 4B showing IFN-γ production.

FIG. 6B showing total immunoglobulin responses against CH69 in animals; FIG. 6C showing total immunoglobulin responses against CH72 in animals; FIG. 6D showing total immunoglobulin responses against CH77 in animals; FIG. 6E showing total immunoglobulin responses against CH84 in animals; and FIG. 6F showing total immunoglobulin responses against CH93 in animals.

FIG. 7B showing IgG1 responses against CH47 in animals; FIG. 7C showing IgG2a responses against CH77 in animals; and FIG. 7D showing IgG2a responses against CH47 in animals.

FIGS. 8A-D shows IgG1 and IgG2 responses specific to individual peptides in serum of vaccinated mice with FIG. 8A showing IgG1 responses against CH37 in animals; FIG. 8B showing IgG1 responses against CH77 in animals; FIG. 8C showing IgG2a responses against CH37 in animals; and FIG. 8D showing IgG2a responses against CH77 in animals.

FIG. 9B showing total immunoglobulin responses against CH37 in animals; FIG. 9C showing total immunoglobulin responses against CH47 in animals; FIG. 9D showing total immunoglobulin responses against CH69 in animals; FIG. 9E showing total immunoglobulin responses against CH72 in animals; FIG. 9F showing total immunoglobulin responses against CH77 in animals; FIG. 9G showing total immunoglobulin responses against CH84 in animals; and FIG. 9H showing total immunoglobulin responses against peptide mix in animals.

DETAILED DESCRIPTION

Figure 1A:
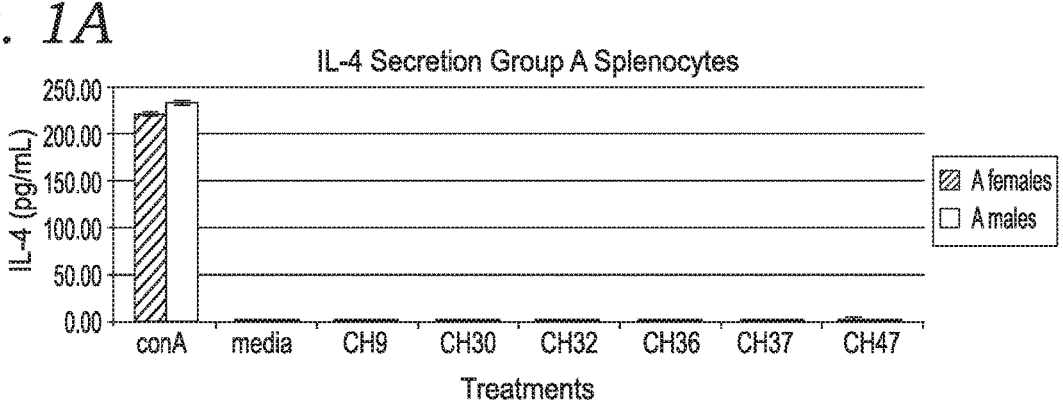
FIGS. 1A-D show the production of IL-4 and IFN-γ by splenocytes after 48 hour exposure to single peptides in vitro with FIG. 1A showing IL-4 production in Group A animals.

The life cycle of trypanosomes can be divided into a vector stage where the trypanosomes proliferate and differentiate in the vector to produce an infecting form of the parasite, and a human stage where the trypanosome differentiates and proliferates in a human host. During the human stage, the vector feeds on a human host and passes the infecting form of the trypanosome, called metacyclic trypomastigote, into the circulatory system. The metacyclic trypomastigotes invade host cells and then differentiate into amastigotes and begins proliferating intracellularly. Intracellular amastigotes differentiate into trypomastigotes and eventually rupture the host cells and enter into the blood system where the parasite is capable of infecting new host cells and/or be transferred to a new vector.

When intracellular amastigotes infect host cells, various proteins derived from these parasites accumulate in the cytoplasm. These protein can be processed by the proteasome, a cytosolic protease complex, to generate small protein fragments or peptides typically between 8 to 11 amino acid in length. These peptides are then bound to the cleft of histocompatibility complex class I (MHC-I) glycoproteins in the endoplasmic reticulum and are transported to the plasma membrane of the infected cells. These peptides can also protrude or sit within the cell membrane if they contain a membrane anchor in their sequence. Antigen presenting cells can also engulf *Trypanosoma* or *Trypanosoma*-infected cells and process the parasite proteins into larger peptides fragments between 12 and 35 amino acids that can also be presented to the immune system bound to MHC Class II molecules.

The present specification takes advantage of these peptide fragments expressed on the surface of infected cells by providing immunogenic compositions comprising CD8$^+$ and CD4$^+$ T Cells that can recognize the peptide fragments within Class I and II MHC complexes and B Cells that can recognize these peptides within the cell membrane and Class II MHC molecules. The immunogenic compositions elicit the generation of T cells and antibodies to these antigens, which, in turn, recognize the trypanosome peptide fragments located on the cell surface of infected cells. The recognition of these cell surface peptide fragments by T cells and/or antibodies disrupts the cell membrane, ultimately resulting in the destruction of these infected cells, disruption of the proliferation of the trypanosomes and death of the intracellular amastigotes.

One key discovery of the present specification is that the disclosed trypanosome antigens used to generate an immune response are derived from intracellular proteins of the parasite. This is important because the resulting immune response does not directly attack the *trypanosoma* itself to any great extent. Another key discovery is that the disclosed treatments can more effectively control trypanosome populations as the immune response targets infected cells where the parasite is proliferating.

Aspects of the present disclosure comprise, in part, a *Trypanosoma* antigen. An antigen is a molecule that elicits an immune response and includes, without limitation, peptides, polysaccharides and conjugates of lipids, such as, e.g., lipoproteins and glycolipids. A *Trypanosoma* antigen is any antigen that can elicit an immune response against a *Trypanosoma* pathogen or component comprising a *Trypanosoma* pathogen. A component comprising a *Trypanosoma* pathogen includes, without limitation, the genome of *Trypanosoma*, a protein encoded by the genome of *Trypanosoma*, and lipid membrane components of the *Trypanosoma* pathogen. In an aspect of this embodiment, *Trypanosoma* antigen is any antigen that can elicit an immune response against a single *Trypanosoma* strain or component comprising a *Trypanosoma* strain. In another aspect of this embodiment, *Trypanosoma* antigen is any antigen that can elicit an immune response against a two or more *Trypanosoma* strains or component comprising two or more *Trypanosoma* strains.

A *Trypanosoma* antigen must be large enough to be substantially unique in sequence, thus reducing the possibility of producing antibodies that are cross-reactive against antigens other than a *Trypanosoma* antigen disclosed herein. Typically, a *Trypanosoma* antigen disclosed herein has a length of about 5 to about 100 amino acids.

In aspects of this embodiment, a *Trypanosoma* antigen disclosed herein may have a length of, e.g., about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, or about 75 amino acids. In other aspects of this embodiment, a *Trypanosoma* antigen disclosed herein may have a length of, e.g., at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, or at least 75 amino acids. In yet other aspects of this embodiment, a *Trypanosoma* antigen disclosed herein may have a length of, e.g., at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, at most 50, at most 55, at most 60, at most 65, at most 70, or at most 75 amino acids.

In still other aspects of this embodiment, a *Trypanosoma* antigen disclosed herein may have a length of, e.g., between about 7 to about 10 amino acids, about 7 to about 12 amino acids, about 7 to about 15 amino acids, about 7 to about 18 amino acids, about 7 to about 20 amino acids, about 7 to about 25 amino acids, about 7 to about 30 amino acids, about 7 to about 35 amino acids, about 7 to about 40 amino acids, about 7 to about 45 amino acids, about 7 to about 50 amino acids, about 7 to about 55 amino acids, about 7 to about 60 amino acids, about 7 to about 65 amino acids, about 7 to about 70 amino acids, about 7 to about 75 amino acids, about 10 to about 12 amino acids, about 10 to about 15 amino acids, about 10 to about 18 amino acids, about 10 to about 20 amino acids, about 10 to about 25 amino acids, about 10 to about 30 amino acids, about 10 to about 35 amino acids, about 10 to about 40 amino acids, about 10 to about 45 amino acids, about 10 to about 50 amino acids, about 10 to about 55 amino acids, about 10 to about 60 amino acids, about 10 to about 65 amino acids, about 10 to about 70 amino acids, about 10 to about 75 amino acids, about 12 to about 15 amino acids, about 12 to about 18 amino acids, about 12 to about 20 amino acids, about 12 to about 25 amino acids, about 12 to about 30 amino acids, about 12 to about 35 amino acids, about 12 to about 40 amino acids, about 12 to about 45 amino acids, about 12 to about 50 amino acids, about 12 to about 55 amino acids, about 12 to about 60 amino acids, about 12 to about 65 amino acids, about 12 to about 70 amino acids, about 12 to about 75 amino acids, about 15 to about 18 amino acids, about 15 to about 20 amino acids, about 15 to about 25 amino acids, about 15 to about 30 amino acids, about 15 to about 35 amino acids, about 15 to about 40 amino acids, about 15 to about 45 amino acids, about 15 to about 50 amino acids, about 15 to about 55 amino acids, about 15 to about 60 amino acids, about 15 to about 65 amino acids, about 15 to about 70 amino acids, about 15 to about 75 amino acids, about 18 to about 20 amino acids, about 18 to about 25 amino acids, about 18 to about 30 amino acids, about 18 to about 35 amino acids, about 18 to about 40 amino acids, about 18 to about 45 amino acids, about 18 to about 50 amino acids, about 18 to about 55 amino acids, about 18 to about 60 amino acids, about 18 to about 65 amino acids, about 18 to about 70 amino acids, about 18 to about 75 amino acids, about 20 to about 25 amino acids, about 20 to about 30 amino acids, about 20 to about 35 amino acids, about 20 to about 40 amino acids, about 20 to about 45 amino acids, about 20 to about 50 amino acids, about 20 to about 55 amino acids, about 20 to about 60 amino acids, about 20 to about 65 amino acids, about 20 to about 70 amino acids, about 20 to about 75 amino acids, about 25 to about 30 amino acids, about 25 to about 35 amino acids, about 25 to about 40 amino acids, about 25 to about 45 amino acids, about 25 to about 50 amino acids, about 25 to about 55 amino acids, about 25 to about 60 amino acids, about 25 to about 65 amino acids, about 25 to about 70 amino acids, about 25 to about 75 amino acids, about 30 to about 35 amino acids, about 30 to about 40 amino acids, about 30 to about 45 amino acids, about 30 to about 50 amino acids, about 30 to about 55 amino acids, about 30 to about 60 amino acids, about 30 to about 65 amino acids, about 30 to about 70 amino acids, about 30 to about 75 amino acids, about 35 to about 40 amino acids, about 35 to about 45 amino acids, about 35 to about 50 amino acids, about 35 to about 55 amino acids, about 35 to about 60 amino acids, about 35 to about 65 amino acids, about 35 to about 70 amino acids, about 35 to about 75 amino acids, about 40 to about 45 amino acids, about 40 to about 50 amino acids, about 40 to about 55 amino acids, about 40 to about 60 amino acids, about 40 to about 65 amino acids, about 40 to about 70 amino acids, about 40 to about 75 amino acids, about 45 to about 50 amino acids, about 45 to about 55 amino acids, about 45 to about 60 amino acids, about 45 to about 65 amino acids, about 45 to about 70 amino acids, about 45 to about 75 amino acids, about 50 to about 55 amino acids, about 50 to about 60 amino acids, about 50 to about 65 amino acids, about 50 to about 70 amino acids, or about 50 to about 75 amino acids.

In another embodiment, a *Trypanosoma* antigen disclosed herein comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12. In aspects of this embodiment, a *Trypanosoma* antigen disclosed herein has an amino acid identity of, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12. In yet other aspects of this embodiment, a *Trypanosoma* antigen disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

In other aspects of this embodiment, a *Trypanosoma* antigen disclosed herein comprises an amino acid sequence having a length of, e.g., at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, at least 25 amino acids, at least 26 amino acids, at least 27 amino acids, at least 28 amino acids, at least 29 amino acids, at least 30 amino acids, at least 31 amino acids, at least 32 amino acids, at least 33 amino acids, at least 34 amino acids, at least 35 amino acids, at least 36 amino acids, at least 37 amino acids, at least 38 amino acids, at least 39 amino acids or at least 40 amino acids, the amino acid sequence being taken from a contiguous amino acid subsequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12. In yet other aspects of this embodiment, a *Trypanosoma* antigen disclosed herein comprises an amino acid sequence having a length of, e.g., at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, at most 25 amino acids, at most 26 amino acids, at most 27 amino acids, at most 28 amino acids, at most 29 amino acids, at most 30 amino acids, at most 31 amino acids, at most 32 amino acids, at most 33 amino acids, at most 34 amino acids, at most 35 amino acids, at most 36 amino acids, at most 37 amino acids, at most 38 amino acids, at most 39 amino acids or at most 40 amino acids, the amino acid sequence being taken from a contiguous amino acid subsequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

In other aspects of this embodiment, a *Trypanosoma* antigen disclosed herein has, e.g., at least 1, 2, 3, 4, 5, 6, 7, 8, 9, 10, 11, 12, 13, 14, or 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12; or at most 1, 2, 3, 4, 5, 6, 7, 8, 9, 10, 11, 12, 13, 14, or 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12. In yet other aspects of this embodiment, a *Trypanosoma* antigen disclosed herein has, e.g., at least 1, 2, 3, 4, 5, 6, 7, 8, 9, 10, 11, 12, 13, 14, or 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12; or at most 1, 2, 3, 4, 5, 6, 7, 8, 9, 10, 11, 12, 13, 14, or 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., *Align-M—A New Algorithm for Multiple Alignment of Highly Divergent Sequences*, 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

The present specification describes various polypeptide variants where one amino acid is substituted for another, such as, e.g., a *Trypanosoma* antigen disclosed herein. A substitution can be assessed by a variety of factors, such as, e.g., the physic properties of the amino acid being substituted (Table 1) or how the original amino acid would tolerate a substitution (Table 2). The selections of which amino acid can be substituted for another amino acid in a polypeptide are known to a person of ordinary skill in the art.

TABLE 1

Amino Acid Properties

| Property | Amino Acids |
| --- | --- |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

Amino Acid Substitutions

| Amino Acid | Favored Substitution | Neutral Substitutions | Disfavored substitution |
| --- | --- | --- | --- |
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |

TABLE 2-continued

Amino Acid Substitutions

| Amino Acid | Favored Substitution | Neutral Substitutions | Disfavored substitution |
|---|---|---|---|
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

In aspects of this embodiment, a hydrophic amino acid at one particular position in a *Trypanosoma* antigen disclosed herein can be substituted with another hydrophic amino acid. Examples of hydrophic amino acids include, e.g., C, F, I, L, M, V and W. In another aspect of this embodiment, an aliphatic amino acid at one particular position in a *Trypanosoma* antigen disclosed herein can be substituted with another aliphatic amino acid. Examples of aliphatic amino acids include, e.g., A, I, L, P, and V. In yet another aspect of this embodiment, an aromatic amino acid at one particular position in a *Trypanosoma* antigen disclosed herein can be substituted with another aromatic amino acid. Examples of aromatic amino acids include, e.g., F, H, W and Y. In still another aspect of this embodiment, a stacking amino acid at one particular position in a *Trypanosoma* antigen disclosed herein can be substituted with another stacking amino acid. Examples of stacking amino acids include, e.g., F, H, W and Y. In a further aspect of this embodiment, a polar amino acid at one particular position in a *Trypanosoma* antigen disclosed herein can be substituted with another polar amino acid. Examples of polar amino acids include, e.g., D, E, K, N, Q, and R. In a further aspect of this embodiment, a less polar or indifferent amino acid at one particular position in a *Trypanosoma* antigen disclosed herein can be substituted with another less polar or indifferent amino acid. Examples of less polar or indifferent amino acids include, e.g., A, H, G, P, S, T, and Y. In a yet further aspect of this embodiment, a positive charged amino acid at one particular position in a *Trypanosoma* antigen disclosed herein can be substituted with another positive charged amino acid. Examples of positive charged amino acids include, e.g., K, R, and H. In a still further aspect of this embodiment, a negative charged amino acid at one particular position in a *Trypanosoma* antigen disclosed herein can be substituted with another negative charged amino acid. Examples of negative charged amino acids include, e.g., D and E. In another aspect of this embodiment, a small amino acid at one particular position in a *Trypanosoma* antigen disclosed herein can be substituted with another small amino acid. Examples of small amino acids include, e.g., A, D, G, N, P, S, and T. In yet another aspect of this embodiment, a C-beta branching amino acid at one particular position in a *Trypanosoma* antigen disclosed herein can be substituted with another C-beta branching amino acid. Examples of C-beta branching amino acids include, e.g., I, T and V.

One or more carriers may be linked to a *Trypanosoma* antigen disclosed herein in order to enhance the immunogenicity of a *Trypanosoma* antigen that is immunogenic, non-immunogenic, or weakly immunogenic when not associated with the carrier. Non-limiting examples, include, e.g., a keyhole limpet hemacyanin (KLH), an ovalbumin (OVA), a thyroglobulin (THY), a bovine serum albumin (BSA), a soybean trypsin inhibitor (STI), or a multiple attachment peptide (MAP). A non-antigenic or weakly antigenic antigen can be made antigenic by coupling the antigen to a carrier. Various other carrier and methods for coupling an antigen to a carrier are described in, e.g., Harlow and Lane, supra, 1998a; Harlow and Lane, supra, 1998b; and David W. Waggoner, Jr. et al., *Immunogenicity-enhancing carriers and compositions thereof and methods of using the same*, U.S. Patent Publication No. 20040057958, each of which is incorporated by reference in its entirety. A *Trypanosoma* antigen disclosed herein may also be generated by expressing the antigen as a fusion protein. Methods for expressing polypeptide fusions are described in, e.g., Ausubel et al., Current Protocols in Molecular Biology (Supplement 47), John Wiley & Sons, New York (1999), each of which is incorporated by reference in its entirety.

Aspects of the present disclosure comprise, in part, an immunogenic composition. An immunogenic composition disclosed herein comprises one or more *Trypanosoma* antigens disclosed herein and optionally one or more adjuvants. An immunogenic composition comprising one or more *Trypanosoma* antigens disclosed herein, when administered to an individual, stimulates an immune response against the one or more *Trypanosoma* strains, thereby producing α-*Trypanosoma* antibodies. An immune response is any response by the immune system of an individual to an immunogenic composition disclosed herein. Exemplary immune responses include, but are not limited to, cellular as well as local and systemic humoral immunity, such as, e.g., CTL responses, including antigen-specific induction of CD8+ CTLs, helper T-cell responses, including T-cell proliferative responses and cytokine release, and B-cell responses including, e.g., an antibody producing response. In an aspect of this embodiment, an immunogenic composition is a vaccine. In another aspect of this embodiment, immunogenic composition comprising one *Trypanosoma* antigen disclosed herein, when administered to an individual, stimulates an immune response against one *Trypanosoma* strain, thereby producing α-*Trypanosoma* antibodies. In another aspect of this embodiment, immunogenic composition comprising one *Trypanosoma* antigen disclosed herein, when administered to an individual, stimulates an immune response against two or more *Trypanosoma* strains, thereby producing α-*Trypanosoma* antibodies against each strain. In another aspect of this embodiment, immunogenic composition comprising one or more *Trypanosoma* antigens disclosed herein, when administered to an individual, stimulates an immune response against one *Trypanosoma* strain, thereby producing α-*Trypanosoma* antibodies. In another aspect of this embodiment, immunogenic composition comprising one or more *Trypanosoma* antigens disclosed herein, when administered to an individual, stimulates an immune response against two or more *Trypanosoma* strains, thereby producing α-*Trypanosoma* antibodies against each strain.

In an aspect of this embodiment, an immunogenic composition disclosed herein comprises one or more *Trypanosoma* antigens comprising SEQ ID NO: 6 (CH47), SEQ ID NO: 9 (CH77), SEQ ID NO: 5 (CH37) or any combination thereof. In a preferred aspect of this embodiment, an immunogenic composition disclosed herein comprises one or more *Trypanosoma* antigens comprising SEQ ID NO: 5 (CH37) and SEQ ID NO: 9 (CH77). In another preferred embodiment, an immunogenic composition disclosed herein comprises one or more *Trypanosoma* antigens comprising SEQ ID NO: 5 (CH37), SEQ ID NO: 6 (CH 47) and SEQ ID NO: 9 (CH77). In a most preferred embodiment, an immunogenic composition disclosed herein comprises one or more *Trypanosoma* antigens comprising SEQ ID NO: 6 (CH 47).

In an aspect of this embodiment, an immunogenic composition disclosed herein comprises one or more *Trypanosoma* antigens comprising SEQ ID NO: 2 (CH30), SEQ ID NO: 5 (CH37), SEQ ID NO: 6 (CH47), SEQ ID NO: 7 (CH 69), SEQ ID NO: 8 (CH72), SEQ ID NO: 9 (CH 77), SEQ ID NO: 11 (CH84), or any combination thereof. In a preferred aspect of this aspect of this embodiment, an immunogenic composition disclosed herein comprises one or more *Trypanosoma* antigens comprising SEQ ID NO: 2 (CH30), SEQ ID NO: 6 (CH47), SEQ ID NO: 7 (CH 69), SEQ ID NO: 8 (CH72), SEQ ID NO: 9 (CH 77) and SEQ ID NO: 11 (CH84). In a preferred aspect of this aspect of this embodiment, an immunogenic composition disclosed herein comprises one or more *Trypanosoma* antigens comprising SEQ ID NO: 2 (CH30), SEQ ID NO: 5 (CH37), SEQ ID NO: 6 (CH47), SEQ ID NO: 7 (CH 69), SEQ ID NO: 8 (CH72), SEQ ID NO: 9 (CH 77) and SEQ ID NO: 11 (CH84). In a preferred aspect of this embodiment, an immunogenic composition disclosed herein comprises one or more *Trypanosoma* antigens comprising SEQ ID NO: 2 (CH30), SEQ ID NO: 5 (CH37), SEQ ID NO: 6 (CH47), SEQ ID NO: 7 (CH 69), SEQ ID NO: 8 (CH72), SEQ ID NO: 9 (CH 77) and SEQ ID NO: 11 (CH84).

In another aspect of this embodiment, an immunogenic composition is a medicament for the treatment of a *Trypanosoma*-based disease. In aspects of this embodiment, a *Trypanosoma* antigen disclosed herein is used to manufacture a medicament for the treatment of a *Trypanosoma*-based disease. In aspects of this embodiment, use of a *Trypanosoma* antigen disclosed herein is in an amount sufficient to treat a *Trypanosoma*-based disease by reducing one or more physiological conditions or symptom associated with a *Trypanosoma* infection or pathology. In other aspects of this embodiment, use of a *Trypanosoma* antigen disclosed herein is in an amount sufficient to immunize or vaccinate the individual against the *Trypanosoma* infection or pathology.

In one embodiment, an immunogenic composition disclosed herein comprises a single *Trypanosoma* antigen disclosed herein. In one embodiment, an immunogenic composition disclosed herein comprises a plurality of *Trypanosoma* antigens disclosed herein. In aspects of this embodiment, an immunogenic composition disclosed herein comprises, e.g., 1, 2, 3, 4, 5, 6, 7, 8, 9, 10, 11, 12, 13, 14, or 15 *Trypanosoma* antigens disclosed herein. In other aspects of this embodiment, an immunogenic composition disclosed herein comprises, e.g., at least 1, at least 2, at least 3, at least 4, at least 5, at least 6, at least 7, at least 8, at least 9, at least 10, at least 11, at least 12, at least 13, at least 14, or at least 15 *Trypanosoma* antigens disclosed herein. In yet other aspects of this embodiment, an immunogenic composition disclosed herein comprises, e.g., at most 1, at most 2, at most 3, at most 4, at most 5, at most 6, at most 7, at most 8, at most 9, at most 10, at most 11, at most 12, at most 13, at most 14, or at most 15 *Trypanosoma* antigens disclosed herein. In still other aspects of this embodiment, an immunogenic composition disclosed herein comprises, e.g., 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 3 to 4, 3 to 5, 3 to 6, 3 to 7, 3 to 8, 3 to 9, 3 to 10, 3 to 11, 3 to 12, 3 to 13, 3 to 14, 3 to 15, 4 to 5, 4 to 6, 4 to 7, 4 to 8, 4 to 9, 4 to 10, 4 to 11, 4 to 12, 4 to 13, 4 to 14, 4 to 15, 5 to 6, 5 to 7, 5 to 8, 5 to 9, 5 to 10, 5 to 11, 5 to 12, 5 to 13, 5 to 14, 5 to 15, 6 to 7, 6 to 8, 6 to 9, 6 to 10, 6 to 11, 6 to 12, 6 to 13, 6 to 14, 6 to 15, 7 to 8, 7 to 9, 7 to 10, 7 to 11, 7 to 12, 7 to 13, 7 to 14, 7 to 15, 8 to 9, 8 to 10, 8 to 11, 8 to 12, 8 to 13, 8 to 14, 8 to 15, 9 to 10, 9 to 11, 9 to 12, 9 to 13, 9 to 14, 9 to 15, 10 to 11, 10 to 12, 10 to 13, 10 to 14, 10 to 15, 11 to 12, 11 to 13, 11 to 14, 11 to 15, 12 to 13, 12 to 14, 12 to 15, 13 to 14, 13 to 15, or 14 to 15 *Trypanosoma* antigens disclosed herein.

The amount of a *Trypanosoma* antigen disclosed herein included in an immunogenic composition is an amount sufficient to elicit an appropriate immune response in the individual. Typically, this amount is also one that does not cause significant adverse side effects. Such amount will vary depending on which specific *Trypanosoma* antigen or antigens are employed. An optimal amount for a particular immunogenic composition can be ascertained by standard studies involving observation of antibody titers and other responses in individuals. A primary immunogenic composition course may include 1, 2 or 3 doses of an immunogenic composition, given at intervals optimal for providing an immunoprotective response.

Generally, an effective and safe amount of a *Trypanosoma* antigen disclosed herein included in an immunogenic composition varies from about 1 µg to 1,000 mg. In aspects of this embodiment, an amount of *Trypanosoma* antigen disclosed herein included in an immunogenic composition may be, e.g., about 1 µg, about 2 µg, about 3 µg, about 4 µg, about 5 µg, about 6 µg, about 7 µg, about 8 µg, about 9 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, 260 µg, about 270 µg, about 280 µg, about 290 µg, about 300 µg, about 310 µg, about 320 µg, about 330 µg, about 340 µg, about 350 µg, 360 µg, about 370 µg, about 380 µg, about 390 µg, about 400 µg, about 410 µg, about 420 µg, about 430 µg, about 440 µg, about 450 µg, 460 µg, about 470 µg, about 480 µg, about 490 µg, about 500 µg, about 510 µg, about 520 µg, about 530 µg, about 540 µg, about 550 µg, 560 µg, about 570 µg, about 580 µg, about 590 µg, about 600 µg, about 610 µg, about 620 µg, about 630 µg, about 640 µg, about 650 µg, 660 µg, about 670 µg, about 680 µg, about 690 µg, about 700 µg, about 710 µg, about 720 µg, about 730 µg, about 740 µg, about 750 µg, 760 µg, about 770 µg, about 780 µg, about 790 µg, about 800 µg, about 810 µg, about 820 µg, about 830 µg, about 840 µg, about 850 µg, 860 µg, about 870 µg, about 880 µg, about 890 µg, about 900 µg, about 910 µg, about 920 µg, about 930 µg, about 940 µg, about 950 µg, 960 µg, about 970 µg, about 980 µg, about 990 µg, or about 1,000 µg.

In other aspects of this embodiment, an amount of *Trypanosoma* antigen disclosed herein included in an immunogenic composition may be, e.g., at least 1 µg, at least 2 µg, at least 3 µg, at least 4 µg, at least 5 µg, at least 6 µg, at least 7 µg, at least 8 µg, at least 9 µg, at least 10 µg, at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 110 µg, at least 120 µg, at least 130 µg, at least 140 µg, at least 150 µg, at least 160 µg, at least 170 µg, at least 180 µg, at least 190 µg, at least 200 µg, at least 210 µg, at least 220 µg, at least 230 µg, at least 240 µg, at least 250 µg, 260 µg, at least 270 µg, at least 280 µg, at least 290 µg, at least 300 µg, at least 310 µg, at least 320 µg, at least 330 µg, at least 340 µg, at least 350 µg, 360 µg, at least 370 µg, at least 380 µg, at least 390 µg, at least 400 µg, at least 410 µg, at least 420 µg, at least 430 µg, at least 440 µg, at least 450 µg, 460 µg, at least 470 µg, at least 480 µg, at least 490 µg, at least 500 µg, at least 510 µg, at least 520 µg, at least 530 µg, at least 540 µg, at least 550 µg, 560 µg, at least 570 µg, at least 580 µg, at least 590 µg, at least 600 µg, at least 610 µg, at least 620 µg, at least 630 µg, at least 640 µg, at least 650 µg, 660 µg, at least 670 µg, at least 680 µg, at least 690 µg, at least 700 µg, at least 710 µg, at least 720 µg, at least 730 µg, at least 740 µg, at least 750 µg, 760 µg, at least 770 µg, at least 780 µg, at least 790 µg, at least 800 µg, at least 810 µg, at least 820 µg, at least 830 µg, at least 840 µg, at least 850 µg, 860 µg, at least 870 µg, at least 880 µg, at least 890 µg, at least 900 µg, at least 910 µg, at least 920 µg, at least 930 µg, at least 940 µg, at least 950 µg, 960 µg, at least 970 µg, at least 980 µg, at least 990 µg, or at least 1,000 µg.

In yet other aspects of this embodiment, an amount of *Trypanosoma* antigen disclosed herein included in an immunogenic composition may be, e.g., at most 1 µg, at most 2 µg, at most 3 µg, at most 4 µg, at most 5 µg, at most 6 µg, at most 7 µg, at most 8 µg, at most 9 µg, at most 10 µg, at most 15 µg, at most 20 µg, at most 25 µg, at most 30 µg, at most 35 µg, at most 40 µg, at most 45 µg, at most 50 µg, at most 55 µg, at most 60 µg, at most 65 µg, at most 70 µg, at most 75 µg, at most 80 µg, at most 85 µg, at most 90 µg, at most 95 µg, at most 100 µg, at most 110 µg, at most 120 µg, at most 130 µg, at most 140 µg, at most 150 µg, at most 160 µg, at most 170 µg, at most 180 µg, at most 190 µg, at most 200 µg, at most 210 µg, at most 220 µg, at most 230 µg, at most 240 µg, at most 250 µg, 260 µg, at most 270 µg, at most 280 µg, at most 290 µg, at most 300 µg, at most 310 µg, at most 320 µg, at most 330 µg, at most 340 µg, at most 350 µg, 360 µg, at most 370 µg, at most 380 µg, at most 390 µg, at most 400 µg, at most 410 µg, at most 420 µg, at most 430 µg, at most 440 µg, at most 450 µg, 460 µg, at most 470 µg, at most 480 µg, at most 490 µg, at most 500 µg, at most 510 µg, at most 520 µg, at most 530 µg, at most 540 µg, at most 550 µg, 560 µg, at most 570 µg, at most 580 µg, at most 590 µg, at most 600 µg, at most 610 µg, at most 620 µg, at most 630 µg, at most 640 µg, at most 650 µg, 660 µg, at most 670 µg, at most 680 µg, at most 690 µg, at most 700 µg, at most 710 µg, at most 720 µg, at most 730 µg, at most 740 µg, at most 750 µg, 760 µg, at most 770 µg, at most 780 µg, at most 790 µg, at most 800 µg, at most 810 µg, at most 820 µg, at most 830 µg, at most 840 µg, at most 850 µg, 860 µg, at most 870 µg, at most 880 µg, at most 890 µg, at most 900 µg, at most 910 µg, at most 920 µg, at most 930 µg, at most 940 µg, at most 950 µg, 960 µg, at most 970 µg, at most 980 µg, at most 990 µg, or at most 1,000 µg.

In still other aspects of this embodiment, an amount of *Trypanosoma* antigen disclosed herein included in an immunogenic composition may be in the range of, e.g., about 1 µg to about 10 µg, about 1 µg to about 20 µg, about 1 µg to about 30 µg, about 1 µg to about 40 µg, about 1 µg to about 50 µg, about 1 µg to about 60 µg, about 1 µg to about 70 µg, about 1 µg to about 80 µg, about 1 µg to about 90 µg, about 1 µg to about 100 µg, about 1 µg to about 110 µg, about 1 µg to about 120 µg, about 1 µg to about 130 µg, about 1 µg to about 140 µg, about 1 µg to about 150 µg, about 5 µg to about 10 µg, about 5 µg to about 20 µg, about 5 µg to about 30 µg, about 5 µg to about 40 µg, about 5 µg to about 50 µg, about 5 µg to about 60 µg, about 5 µg to about 70 µg, about 5 µg to about 80 µg, about 5 µg to about 90 µg, about 5 µg to about 100 µg, about 5 µg to about 110 µg, about 5 µg to about 120 µg, about 5 µg to about 130 µg, about 5 µg to about 140 µg, about 5 µg to about 150 µg, about 10 µg to about 20 µg, about 10 µg to about 30 µg, about 10 µg to about 40 µg, about 10 µg to about 50 µg, about 10 µg to about 60 µg, about 10 µg to about 70 µg, about 10 µg to about 80 µg, about 10 µg to about 90 µg, about 10 µg to about 100 µg, about 10 µg to about 110 µg, about 10 µg to about 120 µg, about 10 µg to about 130 µg, about 10 µg to about 140 µg, about 10 µg to about 150 µg, about 10 µg to about 175 µg, about 10 µg to about 200 µg, about 10 µg to about 225 µg, about 10 µg to about 250 µg, about 25 µg to about 50 µg, about 25 µg to about 75 µg, about 25 µg to about 100 µg, about 25 µg to about 125 µg, about 25 µg to about 150 µg, about 25 µg to about 175 µg, about 25 µg to about 200 µg, about 25 µg to about 225 µg, about 25 µg to about 250 µg, about 50 µg to about 75 µg, about 50 µg to about 100 µg, about 50 µg to about 125 µg, about 50 µg to about 150 µg, about 50 µg to about 175 µg, about 50 µg to about 200 µg, about 50 µg to about 225 µg, about 50 µg to about 250 µg, about 75 µg to about 100 µg, about 75 µg to about 125 µg, about 75 µg to about 150 µg, about 75 µg to about 175 µg, about 75 µg to about 200 µg, about 75 µg to about 225 µg, or about 75 µg to about 250 µg.

In still other aspects of this embodiment, an amount of *Trypanosoma* antigen disclosed herein included in an immunogenic composition may be in the range of, e.g., about 100 µg to about 125 µg, about 100 µg to about 150 µg, about 100 µg to about 175 µg, about 100 µg to about 200 µg, about 100 µg to about 225 µg, about 100 µg to about 250 µg, about 100 µg to about 275 µg, about 100 µg to about 300 µg, about 100 µg to about 325 µg, about 100 µg to about 350 µg, about 100 µg to about 375 µg, about 100 µg to about 400 µg, about 100 µg to about 425 µg, about 100 µg to about 450 µg, about 100 µg to about 475 µg, about 100 µg to about 500 µg, about 100 µg to about 525 µg, about 100 µg to about 550 µg, about 100 µg to about 575 µg, about 100 µg to about 600 µg, about 125 µg to about 150 µg, about 125 µg to about 175 µg, about 125 µg to about 200 µg, about 125 µg to about 225 µg, about 125 µg to about 250 µg, about 125 µg to about 275 µg, about 125 µg to about 300 µg, about 125 µg to about 325 µg, about 125

µg to about 350 µg, about 125 µg to about 375 µg, about 125 µg to about 400 µg, about 125 µg to about 425 µg, about 125 µg to about 450 µg, about 125 µg to about 475 µg, about 125 µg to about 500 µg, about 125 µg to about 525 µg, about 125 µg to about 550 µg, about 125 µg to about 575 µg, about 125 µg to about 600 µg, about 150 µg to about 175 µg, about 150 µg to about 200 µg, about 150 µg to about 225 µg, about 150 µg to about 250 µg, about 150 µg to about 275 µg, about 150 µg to about 300 µg, about 150 µg to about 325 µg, about 150 µg to about 350 µg, about 150 µg to about 375 µg, about 150 µg to about 400 µg, about 150 µg to about 425 µg, about 150 µg to about 450 µg, about 150 µg to about 475 µg, about 150 µg to about 500 µg, about 150 µg to about 525 µg, about 150 µg to about 550 µg, about 150 µg to about 575 µg, about 150 µg to about 600 µg, about 200 µg to about 225 µg, about 200 µg to about 250 µg, about 200 µg to about 275 µg, about 200 µg to about 300 µg, about 200 µg to about 325 µg, about 200 µg to about 350 µg, about 200 µg to about 375 µg, about 200 µg to about 400 µg, about 200 µg to about 425 µg, about 200 µg to about 450 µg, about 200 µg to about 475 µg, about 200 µg to about 500 µg, about 200 µg to about 525 µg, about 200 µg to about 550 µg, about 200 µg to about 575 µg, about 200 µg to about 600 µg, about 200 µg to about 625 µg, about 200 µg to about 650 µg, about 200 µg to about 675 µg, about 200 µg to about 700 µg, about 200 µg to about 725 µg, about 200 µg to about 750 µg, about 200 µg to about 775 µg, about 200 µg to about 800 µg, about 200 µg to about 825 µg, about 200 µg to about 850 µg, about 200 µg to about 875 µg, about 200 µg to about 900 µg, about 200 µg to about 925 µg, about 200 µg to about 950 µg, about 200 µg to about 975 µg, or about 200 µg to about 1,000 µg.

In still other aspects of this embodiment, an amount of *Trypanosoma* antigen disclosed herein included in an immunogenic composition may be in the range of, e.g., about 250 µg to about 275 µg, about 250 µg to about 300 µg, about 250 µg to about 325 µg, about 250 µg to about 350 µg, about 250 µg to about 375 µg, about 250 µg to about 400 µg, about 250 µg to about 425 µg, about 250 µg to about 450 µg, about 250 µg to about 475 µg, about 250 µg to about 500 µg, about 250 µg to about 525 µg, about 250 µg to about 550 µg, about 250 µg to about 575 µg, about 250 µg to about 600 µg, about 250 µg to about 625 µg, about 250 µg to about 650 µg, about 250 µg to about 675 µg, about 250 µg to about 700 µg, about 250 µg to about 725 µg, about 250 µg to about 750 µg, about 250 µg to about 775 µg, about 250 µg to about 800 µg, about 250 µg to about 825 µg, about 250 µg to about 850 µg, about 250 µg to about 875 µg, about 250 µg to about 900 µg, about 250 µg to about 925 µg, about 250 µg to about 950 µg, about 250 µg to about 975 µg, about 250 µg to about 1,000 µg, about 300 µg to about 325 µg, about 300 µg to about 350 µg, about 300 µg to about 375 µg, about 300 µg to about 400 µg, about 300 µg to about 425 µg, about 300 µg to about 450 µg, about 300 µg to about 475 µg, about 300 µg to about 500 µg, about 300 µg to about 525 µg, about 300 µg to about 550 µg, about 300 µg to about 575 µg, about 300 µg to about 600 µg, about 300 µg to about 625 µg, about 300 µg to about 650 µg, about 300 µg to about 675 µg, about 300 µg to about 700 µg, about 300 µg to about 725 µg, about 300 µg to about 750 µg, about 300 µg to about 775 µg, about 300 µg to about 800 µg, about 300 µg to about 825 µg, about 300 µg to about 850 µg, about 300 µg to about 875 µg, about 300 µg to about 900 µg, about 300 µg to about 925 µg, about 300 µg to about 950 µg, about 300 µg to about 975 µg, about 300 µg to about 1,000 µg, about 400 µg to about 425 µg, about 400 µg to about 450 µg, about 400 µg to about 475 µg, about 400 µg to about 500 µg, about 400 µg to about 525 µg, about 400 µg to about 550 µg, about 400 µg to about 575 µg, about 400 µg to about 600 µg, about 400 µg to about 625 µg, about 400 µg to about 650 µg, about 400 µg to about 675 µg, about 400 µg to about 700 µg, about 400 µg to about 725 µg, about 400 µg to about 750 µg, about 400 µg to about 775 µg, about 400 µg to about 800 µg, about 400 µg to about 825 µg, about 400 µg to about 850 µg, about 400 µg to about 875 µg, about 400 µg to about 900 µg, about 400 µg to about 925 µg, about 400 µg to about 950 µg, about 400 µg to about 975 µg, or about 400 µg to about 1,000 µg.

In still other aspects of this embodiment, an amount of *Trypanosoma* antigen disclosed herein included in an immunogenic composition may be in the range of, e.g., about 500 µg to about 525 µg, about 500 µg to about 550 µg, about 500 µg to about 575 µg, about 500 µg to about 600 µg, about 500 µg to about 625 µg, about 500 µg to about 650 µg, about 500 µg to about 675 µg, about 500 µg to about 700 µg, about 500 µg to about 725 µg, about 500 µg to about 750 µg, about 500 µg to about 775 µg, about 500 µg to about 800 µg, about 500 µg to about 825 µg, about 500 µg to about 850 µg, about 500 µg to about 875 µg, about 500 µg to about 900 µg, about 500 µg to about 925 µg, about 500 µg to about 950 µg, about 500 µg to about 975 µg, about 500 µg to about 1,000 µg, about 600 µg to about 625 µg, about 600 µg to about 650 µg, about 600 µg to about 675 µg, about 600 µg to about 700 µg, about 600 µg to about 725 µg, about 600 µg to about 750 µg, about 600 µg to about 775 µg, about 600 µg to about 800 µg, about 600 µg to about 825 µg, about 600 µg to about 850 µg, about 600 µg to about 875 µg, about 600 µg to about 900 µg, about 600 µg to about 925 µg, about 600 µg to about 950 µg, about 600 µg to about 975 µg, about 600 µg to about 1,000 µg, about 700 µg to about 725 µg, about 700 µg to about 750 µg, about 700 µg to about 775 µg, about 700 µg to about 800 µg, about 700 µg to about 825 µg, about 700 µg to about 850 µg, about 700 µg to about 875 µg, about 700 µg to about 900 µg, about 700 µg to about 925 µg, about 700 µg to about 950 µg, about 700 µg to about 975 µg, about 700 µg to about 1,000 µg, about 800 µg to about 825 µg, about 800 µg to about 850 µg, about 800 µg to about 875 µg, about 800 µg to about 900 µg, about 800 µg to about 925 µg, about 800 µg to about 950 µg, about 800 µg to about 975 µg, or about 800 µg to about 1,000 µg.

In aspects of this embodiment, an amount of *Trypanosoma* antigen disclosed herein included in an immunogenic composition may be, e.g., about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, 260 mg, about 270 mg, about 280 mg, about 290 mg, about 300 mg, about 310 mg, about 320 mg, about 330 mg, about 340 mg, about 350 mg, 360 mg, about 370 mg, about 380 mg, about 390 mg, about 400 mg, about 410 mg, about 420 mg, about 430 mg, about 440 mg, about 450 mg, 460 mg, about 470 mg, about 480 mg, about 490 mg, about 500 mg, about 510 mg, about 520 mg, about 530 mg, about 540 mg, about 550 mg, 560 mg, about 570 mg, about 580 mg, about 590 mg, about 600 mg, about 610 mg, about 620 mg, about 630 mg, about 640 mg, about 650 mg, 660 mg, about 670 mg, about 680 mg, about 690 mg, about 700 mg, about 710 mg, about 720 mg, about 730 mg, about 740 mg, about 750 mg, 760 mg, about 770 mg, about 780 mg, about 790 mg, about 800 mg, about 810 mg, about 820 mg, about 830 mg, about 840 mg, about 850 mg, 860 mg, about 870 mg, about 880 mg, about 890 mg, about 900 mg, about 910 mg, about 920 mg, about 930 mg, about 940 mg, about 950 mg, 960 mg, about 970 mg, about 980 mg, about 990 mg, or about 1,000 mg.

In other aspects of this embodiment, an amount of *Trypanosoma* antigen disclosed herein included in an immunogenic composition may be, e.g., at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, 260 mg, at least 270 mg, at least 280 mg, at least 290 mg, at least 300 mg, at least 310 mg, at least 320 mg, at least 330 mg, at least 340 mg, at least 350 mg, 360 mg, at least 370 mg, at least 380 mg, at least 390 mg, at least 400 mg, at least 410 mg, at least 420 mg, at least 430 mg, at least 440 mg, at least 450 mg, 460 mg, at least 470 mg, at least 480 mg, at least 490 mg, at least 500 mg, at least 510 mg, at least 520 mg, at least 530 mg, at least 540 mg, at least 550 mg, 560 mg, at least 570 mg, at least 580 mg, at least 590 mg, at least 600 mg, at least 610 mg, at least 620 mg, at least 630 mg, at least 640 mg, at least 650 mg, 660 mg, at least 670 mg, at least 680 mg, at least 690 mg, at least 700 mg, at least 710 mg, at least 720 mg, at least 730 mg, at least 740 mg, at least 750 mg, 760 mg, at least 770 mg, at least 780 mg, at least 790 mg, at least 800 mg, at least 810 mg, at least 820 mg, at least 830 mg, at least 840 mg, at least 850 mg, 860 mg, at least 870 mg, at least 880 mg, at least 890 mg, at least 900 mg, at least 910 mg, at least 920 mg, at least 930 mg, at least 940 mg, at least 950 mg, 960 mg, at least 970 mg, at least 980 mg, at least 990 mg, or at least 1,000 mg.

In yet other aspects of this embodiment, an amount of *Trypanosoma* antigen disclosed herein included in an immunogenic composition may be, e.g., at most 1 mg, at most 2 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 45 mg, at most 50 mg, at most 55 mg, at most 60 mg, at most 65 mg, at most 70 mg, at most 75 mg, at most 80 mg, at most 85 mg, at most 90 mg, at most 95 mg, at most 100 mg, at most 110 mg, at most 120 mg, at most 130 mg, at most 140 mg, at most 150 mg, at most 160 mg, at most 170 mg, at most 180 mg, at most 190 mg, at most 200 mg, at most 210 mg, at most 220 mg, at most 230 mg, at most 240 mg, at most 250 mg, 260 mg, at most 270 mg, at most 280 mg, at most 290 mg, at most 300 mg, at most 310 mg, at most 320 mg, at most 330 mg, at most 340 mg, at most 350 mg, 360 mg, at most 370 mg, at most 380 mg, at most 390 mg, at most 400 mg, at most 410 mg, at most 420 mg, at most 430 mg, at most 440 mg, at most 450 mg, 460 mg, at most 470 mg, at most 480 mg, at most 490 mg, at most 500 mg, at most 510 mg, at most 520 mg, at most 530 mg, at most 540 mg, at most 550 mg, 560 mg, at most 570 mg, at most 580 mg, at most 590 mg, at most 600 mg, at most 610 mg, at most 620 mg, at most 630 mg, at most 640 mg, at most 650 mg, 660 mg, at most 670 mg, at most 680 mg, at most 690 mg, at most 700 mg, at most 710 mg, at most 720 mg, at most 730 mg, at most 740 mg, at most 750 mg, 760 mg, at most 770 mg, at most 780 mg, at most 790 mg, at most 800 mg, at most 810 mg, at most 820 mg, at most 830 mg, at most 840 mg, at most 850 mg, 860 mg, at most 870 mg, at most 880 mg, at most 890 mg, at most 900 mg, at most 910 mg, at most 920 mg, at most 930 mg, at most 940 mg, at most 950 mg, 960 mg, at most 970 mg, at most 980 mg, at most 990 mg, or at most 1,000 mg.

In still other aspects of this embodiment, an amount of *Trypanosoma* antigen disclosed herein included in an immunogenic composition may be in the range of, e.g., about 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, about 1 mg to about 90 mg, about 1 mg to about 100 mg, about 1 mg to about 110 mg, about 1 mg to about 120 mg, about 1 mg to about 130 mg, about 1 mg to about 140 mg, about 1 mg to about 150 mg, about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, about 5 mg to about 90 mg, about 5 mg to about 100 mg, about 5 mg to about 110 mg, about 5 mg to about 120 mg, about 5 mg to about 130 mg, about 5 mg to about 140 mg, about 5 mg to about 150 mg, about 10 mg to about 20 mg, about 10 mg to about 30 mg, about 10 mg to about 40 mg, about 10 mg to about 50 mg, about 10 mg to about 60 mg, about 10 mg to about 70 mg, about 10 mg to about 80 mg, about 10 mg to about 90 mg, about 10 mg to about 100 mg, about 10 mg to about 110 mg, about 10 mg to about 120 mg, about 10 mg to about 130 mg, about 10 mg to about 140 mg, about 10 mg to about 150 mg, about 10 mg to about 175 mg, about 10 mg to about 200 mg, about 10 mg to about 225 mg, about 10 mg to about 250 mg, about 25 mg to about 50 mg, about 25 mg to about 75 mg, about 25 mg to about 100 mg, about 25 mg to about 125 mg, about 25 mg to about 150 mg, about 25 mg to about 175 mg, about 25 mg to about 200 mg, about 25 mg to about 225 mg, about 25 mg to about 250 mg, about 50 mg to about 75 mg, about 50 mg to about 100 mg, about 50 mg to about 125 mg, about 50 mg to about 150 mg, about 50 mg to about 175 mg, about 50 mg to about 200 mg, about 50 mg to about 225 mg, about 50 mg to about 250 mg, about 75 mg to about 100 mg, about 75 mg to about 125 mg, about 75 mg to about 150 mg, about 75 mg to about 175 mg, about 75 mg to about 200 mg, about 75 mg to about 225 mg, or about 75 mg to about 250 mg.

In still other aspects of this embodiment, an amount of *Trypanosoma* antigen disclosed herein included in an immunogenic composition may be in the range of, e.g., about 100 mg to about 125 mg, about 100 mg to about 150 mg, about 100 mg to about 175 mg, about 100 mg to about 200 mg, about 100 mg to about 225 mg, about 100 mg to about 250 mg, about 100 mg to about 275 mg, about 100 mg to about 300 mg, about 100 mg to about 325 mg, about 100 mg to about 350 mg, about 100 mg to about 375 mg, about 100 mg to about 400 mg, about 100 mg to about 425 mg, about 100 mg to about 450 mg, about 100 mg to about 475 mg, about 100 mg to about 500 mg, about 100 mg to about 525 mg, about 100 mg to about 550 mg, about 100 mg to about 575 mg, about 100 mg to about 600 mg, about 125 mg to about 150 mg, about 125 mg to about 175 mg, about 125 mg to about 200 mg, about 125 mg to about 225 mg, about 125 mg to about 250 mg, about 125 mg to about 275 mg, about 125 mg to about 300 mg, about 125 mg to about 325 mg, about 125 mg to about 350 mg, about 125 mg to about 375 mg, about 125 mg to about 400 mg, about 125 mg to about 425 mg, about 125 mg to about 450 mg, about 125 mg to about 475 mg, about 125 mg to about 500 mg, about 125 mg to about 525 mg, about 125 mg to about 550 mg, about 125 mg to about 575 mg, about 125 mg to about 600 mg, about 150 mg to about 175 mg, about 150 mg to about 200 mg, about 150 mg to about 225 mg, about 150 mg to about 250 mg, about 150 mg to about 275 mg, about 150 mg to about 300 mg, about 150 mg to about 325 mg, about 150 mg to about 350 mg, about 150 mg to about 375 mg, about 150 mg to about 400 mg, about 150 mg to about 425 mg, about 150 mg to about 450 mg, about 150 mg to about 475 mg, about 150 mg to about 500 mg, about 150 mg to about 525 mg, about 150 mg to about 550 mg, about 150 mg to about 575 mg, about 150 mg to about 600 mg, about 200 mg to about 225 mg, about 200 mg to about 250 mg, about 200 mg to about 275 mg, about 200 mg to about 300 mg, about 200 mg to about 325 mg, about 200 mg to about 350 mg, about 200 mg to about 375 mg, about 200 mg to about 400 mg, about 200 mg to about 425 mg, about 200 mg to about 450 mg, about 200 mg to about 475 mg, about 200 mg to about 500 mg, about 200 mg to about 525 mg, about 200 mg to about 550 mg, about 200 mg to about 575 mg, about 200 mg to about 600 mg, about 200 mg to about 625 mg, about 200 mg to about 650 mg, about 200 mg to about 675 mg, about 200 mg to about 700 mg, about 200 mg to about 725 mg, about 200 mg to about 750 mg, about 200 mg to about 775 mg, about 200 mg to about 800 mg, about 200 mg to about 825 mg, about 200 mg to about 850 mg, about 200 mg to about 875 mg, about 200 mg to about 900 mg, about 200 mg to about 925 mg, about 200 mg to about 950 mg, about 200 mg to about 975 mg, or about 200 mg to about 1,000 mg.

In still other aspects of this embodiment, an amount of *Trypanosoma* antigen disclosed herein included in an immunogenic composition may be in the range of, e.g., about 250 mg to about 275 mg, about 250 mg to about 300 mg, about 250 mg to about 325 mg, about 250 mg to about 350 mg, about 250 mg to about 375 mg, about 250 mg to about 400 mg, about 250 mg to about 425 mg, about 250 mg to about 450 mg, about 250 mg to about 475 mg, about 250 mg to about 500 mg, about 250 mg to about 525 mg, about 250 mg to about 550 mg, about 250 mg to about 575 mg, about 250 mg to about 600 mg, about 250 mg to about 625 mg, about 250 mg to about 650 mg, about 250 mg to about 675 mg, about 250 mg to about 700 mg, about 250 mg to about 725 mg, about 250 mg to about 750 mg, about 250 mg to about 775 mg, about 250 mg to about 800 mg, about 250 mg to about 825 mg, about 250 mg to about 850 mg, about 250 mg to about 875 mg, about 250 mg to about 900 mg, about 250 mg to about 925 mg, about 250 mg to about 950 mg, about 250 mg to about 975 mg, about 250 mg to about 1,000 mg, about 300 mg to about 325 mg, about 300 mg to about 350 mg, about 300 mg to about 375 mg, about 300 mg to about 400 mg, about 300 mg to about 425 mg, about 300 mg to about 450 mg, about 300 mg to about 475 mg, about 300 mg to about 500 mg, about 300 mg to about 525 mg, about 300 mg to about 550 mg, about 300 mg to about 575 mg, about 300 mg to about 600 mg, about 300 mg to about 625 mg, about 300 mg to about 650 mg, about 300 mg to about 675 mg, about 300 mg to about 700 mg, about 300 mg to about 725 mg, about 300 mg to about 750 mg, about 300 mg to about 775 mg, about 300 mg to about 800 mg, about 300 mg to about 825 mg, about 300 mg to about 850 mg, about 300 mg to about 875 mg, about 300 mg to about 900 mg, about 300 mg to about 925 mg, about 300 mg to about 950 mg, about 300 mg to about 975 mg, about 300 mg to about 1,000 mg, about 400 mg to about 425 mg, about 400 mg to about 450 mg, about 400 mg to about 475 mg, about 400 mg to about 500 mg, about 400 mg to about 525 mg, about 400 mg to about 550 mg, about 400 mg to about 575 mg, about 400 mg to about 600 mg, about 400 mg to about 625 mg, about 400 mg to about 650 mg, about 400 mg to about 675 mg, about 400 mg to about 700 mg, about 400 mg to about 725 mg, about 400 mg to about 750 mg, about 400 mg to about 775 mg, about 400 mg to about 800 mg, about 400 mg to about 825 mg, about 400 mg to about 850 mg, about 400 mg to about 875 mg, about 400 mg to about 900 mg, about 400 mg to about 925 mg, about 400 mg to about 950 mg, about 400 mg to about 975 mg, or about 400 mg to about 1,000 mg.

In still other aspects of this embodiment, an amount of *Trypanosoma* antigen disclosed herein included in an immunogenic composition may be in the range of, e.g., about 500 mg to about 525 mg, about 500 mg to about 550 mg, about 500 mg to about 575 mg, about 500 mg to about 600 mg, about 500 mg to about 625 mg, about 500 mg to about 650 mg, about 500 mg to about 675 mg, about 500 mg to about 700 mg, about 500 mg to about 725 mg, about 500 mg to about 750 mg, about 500 mg to about 775 mg, about 500 mg to about 800 mg, about 500 mg to about 825 mg, about 500 mg to about 850 mg, about 500 mg to about 875 mg, about 500 mg to about 900 mg, about 500 mg to about 925 mg, about 500 mg to about 950 mg, about 500 mg to about 975 mg, about 500 mg to about 1,000 mg, about 600 mg to about 625 mg, about 600 mg to about 650 mg, about 600 mg to about 675 mg, about 600 mg to about 700 mg, about 600 mg to about 725 mg, about 600 mg to about 750 mg, about 600 mg to about 775 mg, about 600 mg to about 800 mg, about 600 mg to about 825 mg, about 600 mg to about 850 mg, about 600 mg to about 875 mg, about 600 mg to about 900 mg, about 600 mg to about 925 mg, about 600 mg to about 950 mg, about 600 mg to about 975 mg, about 600 mg to about 1,000 mg, about 700 mg to about 725 mg, about 700 mg to about 750 mg, about 700 mg to about 775 mg, about 700 mg to about 800 mg, about 700 mg to about 825 mg, about 700 mg to about 850 mg, about 700 mg to about 875 mg, about 700 mg to about 900 mg, about 700 mg to about 925 mg, about 700 mg to about 950 mg, about 700 mg to about 975 mg, about 700 mg to about 1,000 mg, about 800 mg to about 825 mg, about 800 mg to about 850 mg, about 800 mg to about 875 mg, about 800 mg to about 900 mg, about 800 mg to about 925 mg, about 800 mg to about 950 mg, about 800 mg to about 975 mg, or about 800 mg to about 1,000 mg.

An immunogenic compositions disclosed herein may optionally and further comprise one or more adjuvants. An adjuvant is any substance or mixture of substances that increases or diversifies the immune response to a *Trypanosoma* antigen disclosed herein. An adjuvant may serve to reduce the number of immunizations or the amount of antigen required for protective immunization. Non-limiting adjuvants include, e.g., liposomes, virus-like particles (VLPs), nanoparticles, oily phases, including, without limitation, the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); and lipopolysaccharide (LPS). Such adjuvants are generally used in the form of an emulsion with an aqueous phase, or, more commonly, with water-insoluble inorganic salts. These inorganic salts include aluminum hydroxide, zinc sulfate, colloidal iron hydroxide, calcium phosphate or calcium chloride.

Another example of an adjuvant are the aluminum-based adjuvants (or alum-based adjuvants). Aluminum-based adjuvants stimulates an immune response against co-administered antigens by precipitating antigens to form a "depot." Aluminum-based adjuvants primarily stimulate a $T_{H2}$ immune response. Commonly used alum-based adjuvants include aluminum hydroxide ($Al(OH)_3$), aluminum phosphate ($AlPO_4$), aluminum hydroxyphosphate, amorphous aluminum hydroxyphosphate sulfate (AAHS) and so-called "alum" $KAl(SO_4).12H_2O$.

Specific adjuvants and methods of making and using are described in, e.g., Gupta et al. Vaccine, 11: 993-306, 1993; Arnon, R. (Ed.) Synthetic Vaccines 1:83-92, CRC Press, Inc., Boca Raton, Fla., 1987; and David W. Waggoner, Jr. et al., Immunogenicity-Enhancing Carriers and Compositions Thereof and Methods of Using the Same, U.S. Patent Publication No. 20040057958 (Mar. 25, 2004). Additional adjuvants include any compound described in Chapter 7 (pp 141-227) of "Vaccine Design, The Subunit and Adjuvant Approach" (eds. Powell, M. F. and Newman, M. J.) Pharmaceutical Biotechnology, Volume 6, Plenum Press (New York). Examples from this compendium include Muramyl Dipeptide (MDP) and Montanide 720. Molecules such as Poly Inosine:Cytosine (Poly I:C) or plasmid DNA containing CpG motifs can also be administered as adjuvants in combination with antigens encapsulated in microparticles. In another example, the adjuvant is an agent that facilitates entry of the antigenic compound into the cytoplasm of a cell such as listeriolysin, streptolysin or a mixture thereof.

In one embodiment, an immunogenic composition disclosed herein comprises a single adjuvant disclosed herein. In one embodiment, an immunogenic composition disclosed herein comprises a plurality of adjuvants disclosed herein. In aspects of this embodiment, an immunogenic composition disclosed herein comprises, e.g., 1, 2, 3, 4, or 5 adjuvants disclosed herein. In other aspects of this embodiment, an immunogenic composition disclosed herein comprises, e.g., at least 1, at least 2, at least 3, at least 4, or at least 5 adjuvants disclosed herein. In yet other aspects of this embodiment, an immunogenic composition disclosed herein comprises, e.g., at most 1, at most 2, at most 3, at most 4, or at most 5 adjuvants disclosed herein. In still other aspects of this embodiment, an immunogenic composition disclosed herein comprises, e.g., 1 to 2, 1 to 3, 1 to 4, 1 to 5, 2 to 3, 2 to 4, 2 to 5, 3 to 4, 3 to 5, or 4 to 5 adjuvants disclosed herein.

An adjuvant is typically comprises half the volume of the administered dose. Typically, an immunogenic composition comprising an adjuvant will be administered in a dose of about 0.25 mL to about 1 mL. Thus, if an immunogenic composition is administered in about 1 mL dose, about 0.5 mL of this composition will be an adjuvant. Similarly, if an immunogenic composition is administered in about 0.5 mL dose, about 0.25 mL of this composition will be an adjuvant.

The amount of an adjuvant disclosed herein included in an immunogenic composition is an amount effective in increasing an appropriate immune response of the targeted *Trypanosoma* antigen in the individual. Typically, this amount is also one that does not cause significant adverse side effects. Such amount will vary depending on which adjuvant or adjuvants are employed. An optimal amount of an adjuvant for a particular immunogenic composition can be ascertained by standard studies involving observation of antibody titers and other responses in individuals.

Generally, an effective and safe dose of adjuvant disclosed herein varies from about 100 μg/mL to about 1,500 μg/mL concentration. In aspects of this embodiment, an amount of adjuvant disclosed herein included in an immunogenic composition may be, e.g., about 100 μg/mL, about 200 μg/mL, about 300 μg/mL, about 400 μg/mL, about 500 μg/mL, about 600 μg/mL, about 700 μg/mL, about 800 μg/mL, about 900 μg/mL, about 1,000 μg/mL, about 1,100 μg/mL, about 1,200 μg/mL, about 1,300 μg/mL, about 1,400 μg/mL, or about 1,500 μg/mL. In other aspects of this embodiment, an amount of adjuvant disclosed herein included in an immunogenic composition may be, e.g., at least 100 μg/mL, at least 200 μg/mL, at least 300 μg/mL, at least 400 μg/mL, at least 500 μg/mL, at least 600 μg/mL, at least 700 μg/mL, at least 800 μg/mL, at least 900 μg/mL, at least 1,000 μg/mL, at least 1,100 μg/mL, at least 1,200 μg/mL, at least 1,300 μg/mL, at least 1,400 μg/mL, or at least 1,500 μg/mL. In yet other aspects of this embodiment, an amount of adjuvant disclosed herein included in an immunogenic composition may be, e.g., at most 100 μg/mL, at most 200 μg/mL, at most 300 μg/mL, at most 400 μg/mL, at most 500 μg/mL, at most 600 μg/mL, at most 700 μg/mL, at most 800 μg/mL, at most 900 μg/mL, at most 1,000 μg/mL, at most 1,100 μg/mL, at most 1,200 μg/mL, at most 1,300 μg/mL, at most 1,400 μg/mL, or at most 1,500 μg/mL.

In yet other aspects of this embodiment, an amount of adjuvant disclosed herein included in an immunogenic composition may be, e.g., about 100 μg/mL to about 200 μg/mL, about 100 μg/mL to about 300 μg/mL, about 100 μg/mL to about 400 μg/mL, about 100 μg/mL to about 500 μg/mL, about 100 μg/mL to about 600 μg/mL, about 100 μg/mL to about 700 μg/mL, about 100 μg/mL to about 800 μg/mL, about 100 μg/mL to about 900 μg/mL, about 100 μg/mL to about 1,000 μg/mL, about 100 μg/mL to about 1,200 μg/mL, about 100 μg/mL to about 1,300 μg/mL, about 100 μg/mL to about 1,400 μg/mL, about 100 μg/mL to about 1,500 μg/mL, about 200 μg/mL to about 300 μg/mL, about 200 μg/mL to about 400 μg/mL, about 200 μg/mL to about 500 μg/mL, about 200 μg/mL to about 600 μg/mL, about 200 μg/mL to about 700 μg/mL, about 200 μg/mL to about 800 μg/mL, about 200 μg/mL to about 900 μg/mL, about 200 μg/mL to about 1,000 μg/mL, about 200 μg/mL to about 1,200 μg/mL, about 200 μg/mL to about 1,300 μg/mL, about 200 μg/mL to about 1,400 μg/mL, about 200 μg/mL to about 1,500 μg/mL, about 300 μg/mL to about 400 μg/mL, about 300 μg/mL to about 500 μg/mL, about 300 μg/mL to about 600 μg/mL, about 300 μg/mL to about 700 μg/mL, about 300 μg/mL to about 800 μg/mL, about 300 μg/mL to about 900 μg/mL, about 300 μg/mL to about 1,000 μg/mL, about 300 μg/mL to about 1,200 μg/mL, about 300 μg/mL to about 1,300 μg/mL, about 300 μg/mL to about 1,400 μg/mL, about 300 μg/mL to about 1,500 μg/mL, about 400 μg/mL to about 500 μg/mL, about 400 μg/mL to about 600 μg/mL, about 400 μg/mL to about 700 μg/mL, about 400 μg/mL to about 800 μg/mL, about 400 μg/mL to about 900 μg/mL, about 400 μg/mL to about 1,000 μg/mL, about 400 μg/mL to about 1,200 μg/mL, about 400 μg/mL to about 1,300 μg/mL, about 400 μg/mL to about 1,400 μg/mL, about 400 μg/mL to about 1,500 μg/mL, about 500 μg/mL to about 600 μg/mL, about 500 μg/mL to about 700 μg/mL, about 500 μg/mL to about 800 μg/mL, about 500 μg/mL to about 900 μg/mL, about 500 μg/mL to about 1,000 μg/mL, about 500 μg/mL to about 1,200 μg/mL, about 500 μg/mL to about 1,300 μg/mL, about 500 μg/mL to about 1,400 μg/mL, about 500 μg/mL to about 1,500 μg/mL, about 600 μg/mL to about 700 μg/mL, about 600 μg/mL to about 800 μg/mL, about 600 μg/mL to about 900 μg/mL, about 600 μg/mL to about 1,000 μg/mL, about 600 μg/mL to about 1,200 μg/mL, about 600 μg/mL to about 1,300 μg/mL, about 600 μg/mL to about 1,400 μg/mL, about 600 μg/mL to about 1,500 μg/mL, about 700 μg/mL to about 800 μg/mL, about 700 μg/mL to about 900 μg/mL, about 700 μg/mL to about 1,000 μg/mL, about 700 μg/mL to about 1,200 μg/mL, about 700 µg/mL to about 1,300 µg/mL, about 700 µg/mL to about 1,400 µg/mL, about 700 µg/mL to about 1,500 µg/mL, about 800 µg/mL to about 900 µg/mL, about 800 µg/mL to about 1,000 µg/mL, about 800 µg/mL to about 1,200 µg/mL, about 800 µg/mL to about 1,300 µg/mL, about 800 µg/mL to about 1,400 µg/mL, about 800 µg/mL to about 1,500 µg/mL, about 900 µg/mL to about 1,000 µg/mL, about 900 µg/mL to about 1,200 µg/mL, about 900 µg/mL to about 1,300 µg/mL, about 900 µg/mL to about 1,400 µg/mL, about 900 µg/mL to about 1,500 µg/mL, about 1,000 µg/mL to about 1,200 µg/mL, about 1,000 µg/mL to about 1,300 µg/mL, about 1,000 µg/mL to about 1,400 µg/mL, about 1,000 µg/mL to about 1,500 µg/mL, about 1,100 µg/mL to about 1,200 µg/mL, about 1,100 µg/mL to about 1,300 µg/mL, about 1,100 µg/mL to about 1,400 µg/mL, about 1,100 µg/mL to about 1,500 µg/mL, about 1,200 µg/mL to about 1,300 µg/mL, about 1,200 µg/mL to about 1,400 µg/mL, about 1,200 µg/mL to about 1,500 µg/mL, about 1,300 µg/mL to about 1,400 µg/mL, about 1,300 µg/mL to about 1,500 µg/mL, or about 1,400 µg/mL to about 1,500 µg/mL.

An immunogenic composition disclosed herein may further comprise one or more pharmaceutically acceptable carriers. Pharmaceutically acceptable carriers useful in the immunogenic compositions disclosed herein include any compatible agent that is nontoxic to an individual at the dosages and concentrations employed, and has substantially no long term or permanent detrimental effect when administered and encompasses terms such as pharmacologically acceptable vehicle, stabilizer, solubilizer, diluent, additive, auxiliary or excipient. Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. A carrier disclosed herein may also act as an adjuvant. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); GOODMAN & GILMAN'S THE PHARMACOLOGICAL BASIS OF THERAPEUTICS (Joel G. Hardman et al., eds., McGraw-Hill Professional, 10th ed. 2001); and HANDBOOK OF PHARMACEUTICAL EXCIPIENTS (Raymond C. Rowe et al., APhA Publications, 4th edition 2003).

An immunogenic composition disclosed herein may further comprise one or more pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

Aspects of the present specification disclose, in part, a method of treating a *Trypanosoma*-based disease. Such methods include therapeutic (following *Trypanosoma* infection) and prophylactic (prior to *Trypanosoma* exposure, infection or pathology). For example, therapeutic and prophylactic methods of treating an individual for a *Trypanosoma* infection include treatment of an individual having or at risk of having a *Trypanosoma* infection or pathology, treating an individual with a *Trypanosoma* infection, and methods of protecting an individual from a *Trypanosoma* infection, to reduce, suppress or eliminate the probability of a *Trypanosoma* infection in an individual, to reduce, suppress or eliminate susceptibility of an individual to a *Trypanosoma* infection, to reduce, suppress or eliminate a *Trypanosoma* infection in an individual, to reduce, suppress or eliminate an symptomology, a morbidity and/or mortality, or to reduce, suppress or eliminate transmission of a *Trypanosoma* from an infected individual to an uninfected individual. Such methods include administering an immunogenic composition disclosed herein to therapeutically or prophylactically treat (vaccinate or immunize) an individual having or at risk of having a *Trypanosoma* infection or pathology. Accordingly, methods can treat the *Trypanosoma* infection or pathology, or provide the individual with protection from infection (e.g., prophylactic protection).

In one embodiment, a method of treating a *Trypanosoma*-based disease comprises administering to an individual in need thereof a *Trypanosoma* antigen or an immunogenic composition disclosed herein in an amount sufficient to reduce one or more physiological conditions or symptom associated with a *Trypanosoma* infection or pathology, thereby treating the *Trypanosoma*-based disease. In aspects of this embodiment, an immunogenic composition comprises one or more *Trypanosoma* antigens disclosed herein.

In one embodiment, a *Trypanosoma* antigen or an immunogenic composition disclosed herein is used to treat a *Trypanosoma*-based disease. Use of a *Trypanosoma* antigen or an immunogenic composition disclosed herein treats a

*Trypanosoma*-based disease by reducing one or more physiological conditions or symptom associated with a *Trypanosoma* infection or pathology. In aspects of this embodiment, administration of a *Trypanosoma* antigen or an immunogenic composition disclosed herein is in an amount sufficient to reduce one or more physiological conditions or symptom associated with a *Trypanosoma* infection or pathology, thereby treating the *Trypanosoma*-based disease. In other aspects of this embodiment, administration of a *Trypanosoma* antigen or an immunogenic composition disclosed herein is in an amount sufficient to increase, induce, enhance, augment, promote or stimulate *Trypanosoma* clearance or removal; or decrease, reduce, inhibit, suppress, prevent, control, or limit transmission of *Trypanosoma* to another individual.

In one embodiment, a method of treating a *Trypanosoma*-based disease comprises administering to an individual in need thereof a *Trypanosoma* antigen or immunogenic composition disclosed herein in an amount sufficient to immunize or vaccinate the individual against the *Trypanosoma* infection or pathology, thereby treating the *Trypanosoma*-based disease. In aspects of this embodiment, an immunogenic composition comprises one or more *Trypanosoma* antigens disclosed herein. In other aspects of this embodiment, administration of an immunogenic composition disclosed herein is in an amount sufficient to increase, induce, enhance, augment, promote or stimulate an immune response against a *Trypanosoma*. In yet other aspects of this embodiment, administration of an immunogenic composition disclosed herein is in an amount sufficient to increase, induce, enhance, augment, promote or stimulate *Trypanosoma* clearance or removal; or decrease, reduce, inhibit, suppress, prevent, control, or limit transmission of *Trypanosoma* to another individual.

In one embodiment, a method of treating a *Trypanosoma*-based disease comprises administering to an individual in need thereof a *Trypanosoma* antigen or immunogenic composition disclosed herein in an amount sufficient to protect the individual against a *Trypanosoma* infection or pathology, thereby treating the *Trypanosoma*-based disease. In aspects of this embodiment, an immunogenic composition comprises one or more *Trypanosoma* antigens disclosed herein. In other aspects of this embodiment, administration of an immunogenic composition disclosed herein is in an amount sufficient to immunize or vaccinate the individual against the *Trypanosoma* infection or pathology, or reduce, decrease, limit, control or inhibit susceptibility to a *Trypanosoma* infection or pathology.

In one embodiment, a *Trypanosoma* antigen or immunogenic composition disclosed herein is used to treat a *Trypanosoma*-based disease. In an aspect of this embodiment, use of a *Trypanosoma* antigen or immunogenic composition disclosed herein is in an amount sufficient to immunize or vaccinate the individual against the *Trypanosoma* infection or pathology.

A *Trypanosoma*-based disease refers to any condition, disease or disorder where a pathophysiology effect is due to the presence of *Trypanosoma*. Two different types of trypanosomes exist, and their life cycles are different, the stercorarian species and the salivarian species. Stercorians are trypanosomes passed to the recipient in the feces of insects from the subfamily Triatominae (most importantly *Triatoma infestans*). This group includes *Trypanosoma cruzi, T. lewisi, T. melophagium, T. nabiasi, T. rangeli, T. theileri, T. theodori*. The sub genus *Herpetosoma* contains the species *T. lewisi* and the sub genus *Schizotrypanum* contains *T. cruzi*. Salivarians are trypanosomes of the sub-genera of *Duttonella, Trypanozoon, Pycnomonas* and *Nannomonas*. These trypanosomes are passed to the recipient in the saliva of the tsetse fly (*Glossina* spp.). Antigenic variation is a characteristic shared by the *Salivaria*, which has been particularly well-studied in *T. brucei*. The *Trypanozoon* subgenus contains the species *T. brucei, T. rhodesiense* and *T. equiperdum*. The sub genus *Duttonella* contains the species *T. vivax*. Nannomonas contains *T. congolense*.

In an aspect of this embodiment, a *Trypanosoma*-based disease is a Chagas disease. In another aspect of this embodiment, a *Trypanosoma*-based disease is an African sleeping sickness, including without limitation, East African sleeping sickness and West African sleeping sickness.

Chagas disease, or American trypanosomiasis, is caused by the parasite *T. cruzi*, which is transmitted to animals and people by insect vectors found only in the Americas. If untreated, infection is lifelong and can be life threatening. It is estimated that as many as 8 million people in rural Mexico, Central America, and South America have Chagas disease, most of whom do not know they are infected. In addition, large-scale population movements from rural to urban areas of Latin America and to other regions of the world have increased the geographic distribution and changed the epidemiology of Chagas disease. For example, most people with Chagas disease in the United States acquired their infections in endemic countries and current estimates indicate that more than 300,000 persons with *T. cruzi* infection live in the United States.

*T. cruzi* is a zoonotic disease that can be transmitted to humans by blood-sucking the triatomid kissing bugs. Common triatomine vector species for trypanosomiasis belong to the genera *Triatoma, Rhodnius*, and *Panstrongylus*. A triatomid kissing bug becomes infected by feeding on human or animal blood that contains circulating trypomastigotes of the *T. cruzi* parasites. The ingested trypomastigotes transform into epimastigotes in the vector's midgut, where the parasites multiply and differentiate and then migrate to the hindgut where they differentiate into infective metacyclic trypomastigotes. A human or animal host can become infected by *T. cruzi* when, after an infected triatomid vector takes a blood meal, it defecates and releases trypomastigotes in its feces near the site of the bite wound. Trypomastigotes enter the host through the wound or other breaks in the skin, by ingestion or through intact mucosal membranes, such as the conjunctiva. Inside the host, the trypomastigotes invade cells near the site of inoculation, where they differentiate into intracellular amastigotes. The amastigotes multiply by binary fission and differentiate into trypomastigotes, and then are released into the circulation as bloodstream trypomastigotes. Trypomastigotes infect cells from a variety of tissues and transform into intracellular amastigotes in new infection sites. Clinical manifestations can result from this infective cycle. The bloodstream trypomastigotes do not replicate (different from the African trypanosomes). Replication resumes only when the parasites enter another cell or are ingested by another vector. Although the primary means to obtain Chagas disease is through vector-bourne transmission, *T. cruzi* can also be transmitted through contaminated blood products via transfusions, organ transplanted from an infected donor, trans-placentally from mother to baby (congenital), ingestion of contaminated food or drink and/or by accidental exposure.

Chagas disease has an acute and a chronic phase. Acute Chagas disease occurs immediately after infection, may last up to a few weeks or months, and parasites may be found in the circulating blood. Infection may be mild or asymptomatic. There may be fever or swelling around the site of inoculation (where the parasite entered into the skin or mucous membrane). Rarely, acute infection may result in severe inflammation of the heart muscle or the brain and lining around the brain. Following the acute phase, most infected people enter into a prolonged asymptomatic form of disease (called "chronic indeterminate") during which few or no parasites are found in the blood. During this time, most people are unaware of their infection. Many people may remain asymptomatic for life and never develop Chagas-related symptoms. However, an estimated 20%-30% of infected people will develop debilitating and sometimes life-threatening medical problems over the course of their lives. Complications of chronic Chagas disease may include: 1) cardiac complications including an enlarged heart (cardiomyopathy), a dilated heart that pumps blood poorly, heart failure, heart rhythm abnormalities, heart rate abnormalities, and cardiac arrest (sudden death); and/or 2) intestinal complications including an enlarged esophagus (megaesophagus), an enlarged esophagus colon (megacolon), difficulties with eating or difficulties with passing stool. In people who have suppressed immune systems (for example, due to AIDS or chemotherapy), Chagas disease can reactivate with parasites found in the circulating blood. This occurrence can potentially cause severe disease.

African sleeping sickness, or African trypanosomiasis, is caused by two subspecies of the parasite *Trypanosoma brucei*, that are morphologically indistinguishable. However, the clinical features of this disease depends on the subspecies involved. *T. b. rhodesiense* (East African sleeping sickness) is found in areas of eastern and southeastern Africa. Each year a few hundred cases of East African sleeping sickness are reported to the World Health Organization. Over 95% of the cases of human infection occur in Tanzania, Uganda, Malawi, and Zambia. Wild and domesticated animals are the primary reservoir of infection. Cattle have been implicated in the spread of the disease to new areas and in local outbreaks while a wild animal reservoir is thought to be responsible for sporadic transmission to hunters and visitors to game parks. Infection of international travelers with *T. b. rhodesiense* is rare, but it occasionally occurs. In the U.S., one case per year, on average, is diagnosed. Most cases of sleeping sickness imported into the U.S. have been in travelers who were on safari in East Africa.

*T. b. gambiense* (West African sleeping sickness) is found predominantly in central Africa and in limited areas of West Africa. Most of the sleeping sickness in Africa is caused by this form of the parasite. Epidemics of sleeping sickness have been a significant public health problem in the past, but the disease is reasonably well-controlled at present, with 7,000-10,000 cases reported annually in recent years. Over 95% of the cases of human infection are found in Democratic Republic of Congo, Angola, Sudan, Central African Republic, Chad, and northern Uganda. Humans are the important reservoir of infection, although the parasite can sometimes be found in domestic animals. Imported infection in the U.S. is extremely rare, and most cases have occurred in African nationals who have immigrated rather than in returning U.S. travelers.

Both subspecies *T. brucei* are transmitted by the bite of the tsetse fly (*Glossina* sp.). The tsetse fly becomes infected by feeding on human or animal blood that contains circulating trypomastigotes of the *T. brucei* parasites. In the fly's midgut, the ingested trypomastigotes transform into procyclic trypomastigotes, multiply by binary fission, leave the midgut, and transform into epimastigotes. The epimastigotes reach the fly's salivary glands and continue multiplication by binary fission where they transform into metacyclic trypomastigotes. The cycle in the fly takes approximately 3 weeks. A human or animal host can become infected when, during a blood meal on the host, an infected tsetse fly injects saliva containing metacyclic trypomastigotes of *T. brucei* into skin tissue. The parasites enter the lymphatic system and pass into the bloodstream. Inside the host, they transform into bloodstream trypomastigotes, are carried to other sites throughout the body, reach other blood fluids (e.g., lymph, spinal fluid), and continue the replication by binary fission. Although the primary means to become infected is through vectorbourne transmission, *T. brucei* can also be transmitted through contaminated blood products via transfusions, organ transplanted from an infected donor, transplacentally from mother to baby (congenital), ingestion of contaminated food or drink, sexual intercourse and/or by accidental exposure.

The clinical course of human African sleeping sickness has two stages. In the first stage, the parasite is found in the peripheral circulation, but it has not yet invaded the central nervous system. Once the parasite crosses the blood-brain barrier and infects the central nervous system, the disease enters the second stage. The subspecies have different rates of disease progression, and the clinical features depend on which form of the parasite, *T. b. rhodesiense* or *T. b. gambiense*, is causing the infection. However, infection with either form will eventually lead to coma and death if not treated. *T. b. rhodesiense* infection (East African sleeping sickness) progresses rapidly. In some patients, a large sore (a chancre) will develop at the site of the tsetse bite. Most patients develop fever, headache, muscle and joint aches, and enlarged lymph nodes within 1-2 weeks of the infective bite. Some people develop a rash. After a few weeks of infection, the parasite invades the central nervous system and eventually causes mental deterioration and other neurologic problems. Death ensues usually within months. *T. b. gambiense* infection (West African sleeping sickness) progresses more slowly. At first, there may be only mild symptoms. Infected persons may have intermittent fevers, headaches, muscle and joint aches, and malaise. Itching of the skin, swollen lymph nodes, and weight loss can occur. Usually, after 1-2 years, there is evidence of central nervous system involvement, with personality changes, daytime sleepiness with nighttime sleep disturbance, and progressive confusion. Other neurologic signs, such as partial paralysis or problems with balance or walking may occur, as well as hormonal imbalances. The course of untreated infection rarely lasts longer than 6-7 years and more often kills in about 3 years.

Aspects of the present invention provide, in part, an individual. An individual comprises any mammal including a human, and a human can be a patient.

A method disclosed herein comprises a treatment for a *Trypanosoma*-based disease. A treatment comprises any therapeutic or beneficial effect, including any objective or individually measurable or detectable improvement or benefit provided to a particular individual. A therapeutic or beneficial effect can but need not be complete ablation of all or any particular adverse condition, symptom, disorder, illness, disease or complication caused by or associated with a *Trypanosoma* infection, proliferation, replication, or pathology. Thus, a satisfactory clinical endpoint is achieved when there is an incremental improvement or a partial reduction in an adverse condition, symptom, disorder, illness, disease or complication caused by or associated with a *Trypanosoma* infection, proliferation, replication, or pathology, or an inhibition, decrease, reduction, suppression, prevention, limit or control of worsening or progression of one or more conditions, adverse symptoms, disorders, illnesses, diseases or complications caused by or associated with a *Trypanosoma* infection, proliferation, replication, or pathology over a short or long duration.

In aspects of this embodiment, a method of treatment or use disclosed herein may reduce, decrease, inhibit, limit, delay or prevent a *Trypanosoma* infection, proliferation, replication, or pathology. In other aspects of this embodiment, a method of treatment or use disclosed herein may reduce, decrease, suppress, limit, control or inhibit *Trypanosoma* pathogen numbers or titer; reduce, decrease, suppress, limit, control or inhibit *Trypanosoma* pathogen proliferation or replication; reduce, decrease, suppress, limit, control or inhibit the amount of a *Trypanosoma* protein synthesized; or reduce, decrease, suppress, limit, control or inhibit the amount of a *Trypanosoma* pathogen nucleic acid replicated. In yet other aspects of this embodiment, a method of treatment or use disclosed herein may decrease, reduce, inhibit, suppresses, prevent, control or limit one or more adverse conditions, symptoms, disorders, illnesses, diseases or complications caused by or associated with a *Trypanosoma* infection, proliferation or replication, or pathology. In still other aspects of this embodiment, a method of treatment or use disclosed herein may improve, accelerate, facilitate, enhance, augment, or hasten recovery of an individual from a *Trypanosoma* infection or pathology, or one or more adverse symptoms, disorders, illnesses, diseases or complications caused by or associated with *Trypanosoma* infection, proliferation or replication, or pathology.

In other aspects of this embodiment, a method of treatment or use disclosed herein may stabilize a *Trypanosoma* infection, pathology, or an adverse condition, symptom, disorder, illness, disease or complication caused by or associated with a *Trypanosoma* infection, proliferation, replication, or pathology. In yet other aspects of this embodiment, a method of treatment or use disclosed herein may decrease, reduce, inhibit, suppress, limit or control transmission of a *Trypanosoma* pathogen from an infected individual to an uninfected individual. In still other aspects of this embodiment, a method of treatment or use disclosed herein may reduce or eliminate the need, dosage frequency or amount of a concurrent or subsequent treatment such as another drug or other agent used for treating an individual having or at risk of having a *Trypanosoma* infection or pathology. For example, reducing an amount of an adjunct therapy, for example, a reduction or decrease of a treatment for a *Trypanosoma* infection or pathology, or a vaccination or immunization protocol is considered a beneficial effect. In addition, reducing or decreasing an amount of a *Trypanosoma* antigen used for vaccination or immunization of an individual to provide protection to the individual is considered a beneficial effect.

Aspects of the present specification provide, in part, administering a *Trypanosoma* antigen or immunogenic composition disclosed herein. As used herein, the term "administering" refers to any delivery mechanism that provides a *Trypanosoma* antigen or an immunogenic composition disclosed herein to an individual that potentially results in a clinically, therapeutically, or experimentally beneficial result. The actual delivery mechanism used to administer a composition disclosed herein to an individual can be determined by a person of ordinary skill in the art by taking into account factors, including, without limitation, the type of *Trypanosoma*-based disease, the location of the *Trypanosoma*-based disease, the cause of the *Trypanosoma*-based disease, the severity of the *Trypanosoma*-based disease, the degree of relief desired for *Trypanosoma*-based disease, the duration of relief desired for *Trypanosoma*-based disease, the particular *Trypanosoma* antigen and/or immunogenic composition used, the rate of excretion of the particular *Trypanosoma* antigen and/or immunogenic composition used, the pharmacodynamics of the particular *Trypanosoma* antigen and/or immunogenic composition used, the nature of the other compounds to be included in the immunogenic composition, the particular route of administration, the particular characteristics, history and risk factors of the individual, such as, e.g., age, weight, general health and the like, or any combination thereof.

A composition disclosed herein can be administered to an individual using a cellular uptake approach. Administration of a composition disclosed herein using a cellular uptake approach comprise a variety of enteral or parenteral approaches including, without limitation, oral administration in any acceptable form, such as, e.g., tablet, liquid, capsule, powder, an inhalable or the like; topical administration in any acceptable form, such as, e.g., drops, spray, creams, gels or ointments; intravascular administration in any acceptable form, such as, e.g., intravenous injection, intravenous infusion, intra-arterial injection, intra-arterial infusion and catheter instillation into the vasculature; perk and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A *Trypanosoma* antigen and/or immunogenic composition disclosed herein is administered in an amount sufficient to treat a *Trypanosoma*-based disease. In aspects of this embodiment, the amount of *Trypanosoma* antigen and/or immunogenic composition administered is an amount sufficient to reduce one or more physiological conditions or symptom associated with a *Trypanosoma* infection or pathology, an amount sufficient to immunize or vaccinate the individual against the *Trypanosoma* infection or pathology, or an amount sufficient to protect the individual against a *Trypanosoma* infection or pathology. As used herein, the term "amount sufficient" includes "effective amount", "effective dose", "therapeutically effective amount" or "therapeutically effective dose" and refers to the minimum amount of a *Trypanosoma* antigen and/or immunogenic composition necessary to achieve the desired therapeutic effect and includes an amount sufficient to reduce or inhibit one or more physiological conditions or symptom associated with a *Trypanosoma* infection or pathology.

In aspects of this embodiment, an effective amount of a *Trypanosoma* antigen and/or immunogenic composition disclosed herein reduces or inhibits one or more physiological conditions or symptom associated with a *Trypanosoma* infection or pathology by, e.g., at least 10%, at least 20%, at least 30%, at least 40%, at least 50%, at least 60%, at least 70%, at least 80%, at least 90% or at least 100%. In other aspects of this embodiment, an effective amount of a *Trypanosoma* antigen and/or immunogenic composition disclosed herein reduces or inhibits one or more physiological conditions or symptom associated with a *Trypanosoma* infection or pathology by, e.g., at most 10%, at most 20%, at most 30%, at most 40%, at most 50%, at most 60%, at most 70%, at most 80%, at most 90% or at most 100%. In yet other aspects of this embodiment, an effective amount of a *Trypanosoma* antigen and/or immunogenic composition disclosed herein reduces or inhibits one or more physiological conditions or symptom associated with a *Trypanosoma* infection or pathology by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, an effective amount of a *Trypanosoma* antigen and/or immunogenic composition disclosed herein reduces or inhibits one or more physiological conditions or symptom associated with a *Trypanosoma* infection or pathology for, e.g., at least one week, at least one month, at least two months, at least three months, at least four months, at least five months, at least six months, at least seven months, at least eight months, at least nine months, at least ten months, at least eleven months, or at least twelve months.

The actual effective amount of a *Trypanosoma* antigen and/or immunogenic composition disclosed herein to be administered to an individual can be determined by a person of ordinary skill in the art by taking into account factors, including, without limitation, the type of *Trypanosoma*-based disease, the location of the *Trypanosoma*-based disease, the cause of the *Trypanosoma*-based disease, the severity of the *Trypanosoma*-based disease, the degree of relief desired for *Trypanosoma*-based disease, the duration of relief desired for *Trypanosoma*-based disease, the particular *Trypanosoma* antigen and/or immunogenic composition used, the rate of excretion of the particular *Trypanosoma* antigen and/or immunogenic composition used, the pharmacodynamics of the particular *Trypanosoma* antigen and/or immunogenic composition used, the nature of the other compounds to be included in the immunogenic composition, the particular route of administration used, the particular characteristics, history and risk factors of the individual, such as, e.g., age, weight, general health and the like, or any combination thereof. Additionally, where repeated administration of a *Trypanosoma* antigen and/or immunogenic composition disclosed herein is used, the actual therapeutically effective amount will further depend upon factors, including, without limitation, the frequency of administration, the half-life of a *Trypanosoma* antigen and/ or immunogenic composition disclosed herein, or any combination thereof. It is known by a person of ordinary skill in the art that an effective amount of a *Trypanosoma* antigen and/or immunogenic composition disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

In other aspects of this embodiment, an effective amount of a *Trypanosoma* antigen and/or immunogenic composition disclosed herein generally is in the range of about 0.001 mg/kg/day to about 100 mg/kg/day. In aspects of this embodiment, an effective amount of a *Trypanosoma* antigen and/or immunogenic composition disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

In other aspects of this embodiment, an effective amount of a *Trypanosoma* antigen and/or immunogenic composition disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a *Trypanosoma* antigen and/or immunogenic composition disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a *Trypanosoma* antigen and/or immunogenic composition disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a *Trypanosoma* antigen and/or immunogenic composition disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a *Trypanosoma* antigen and/or immunogenic composition disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/ day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, an effective amount of a *Trypanosoma* antigen and/or immunogenic composition disclosed herein generally is in the range of about 0.001 mg/day to about 100 mg/day. In aspects of this embodiment, an effective amount of a *Trypanosoma* antigen and/or immunogenic composition disclosed herein may be, e.g., at least 0.001 mg/day, at least 0.01 mg/day, at least 0.1 mg/day, at least 1.0 mg/day, at least 5.0 mg/day, at least 10 mg/day, at least 15 mg/day, at least 20 mg/day, at least 25 mg/day, at least 30 mg/day, at least 35 mg/day, at least 40 mg/day, at least 45 mg/day, or at least 50 mg/day.

In other aspects of this embodiment, an effective amount of a *Trypanosoma* antigen and/or immunogenic composition disclosed herein may be in the range of, e.g., about 0.001 mg/day to about 10 mg/day, about 0.001 mg/day to about 15 mg/day, about 0.001 mg/day to about 20 mg/day, about 0.001 mg/day to about 25 mg/day, about 0.001 mg/day to about 30 mg/day, about 0.001 mg/day to about 35 mg/day, about 0.001 mg/day to about 40 mg/day, about 0.001 mg/day to about 45 mg/day, about 0.001 mg/day to about 50 mg/day, about 0.001 mg/day to about 75 mg/day, or about 0.001 mg/day to about 100 mg/day. In yet other aspects of this embodiment, an effective amount of a *Trypanosoma* antigen and/or immunogenic composition disclosed herein may be in the range of, e.g., about 0.01 mg/day to about 10 mg/day, about 0.01 mg/day to about 15 mg/day, about 0.01 mg/day to about 20 mg/day, about 0.01 mg/day to about 25 mg/day, about 0.01 mg/day to about 30 mg/day, about 0.01 mg/day to about 35 mg/day, about 0.01 mg/day to about 40 mg/day, about 0.01 mg/day to about 45 mg/day, about 0.01 mg/day to about 50 mg/day, about 0.01 mg/day to about 75 mg/day, or about 0.01 mg/day to about 100 mg/day. In still other aspects of this embodiment, an effective amount of a *Trypanosoma* antigen and/or immunogenic composition disclosed herein may be in the range of, e.g., about 0.1 mg/day to about 10 mg/day, about 0.1 mg/day to about 15 mg/day, about 0.1 mg/day to about 20 mg/day, about 0.1 mg/day to about 25 mg/day, about 0.1 mg/day to about 30 mg/day, about 0.1 mg/day to about 35 mg/day, about 0.1 mg/day to about 40 mg/day, about 0.1 mg/day to about 45 mg/day, about 0.1 mg/day to about 50 mg/day, about 0.1 mg/day to about 75 mg/day, or about 0.1 mg/day to about 100 mg/day.

In other aspects of this embodiment, an effective amount of a *Trypanosoma* antigen and/or immunogenic composition disclosed herein may be in the range of, e.g., about 1 mg/day to about 10 mg/day, about 1 mg/day to about 15 mg/day, about 1 mg/day to about 20 mg/day, about 1 mg/day to about 25 mg/day, about 1 mg/day to about 30 mg/day, about 1 mg/day to about 35 mg/day, about 1 mg/day to about 40 mg/day, about 1 mg/day to about 45 mg/day, about 1 mg/day to about 50 mg/day, about 1 mg/day to about 75 mg/day, or about 1 mg/day to about 100 mg/day. In yet other aspects of this embodiment, an effective amount of a *Trypanosoma* antigen and/or immunogenic composition disclosed herein may be in the range of, e.g., about 5 mg/day to about 10 mg/day, about 5 mg/day to about 15 mg/day, about 5 mg/day to about 20 mg/day, about 5 mg/day to about 25 mg/day, about 5 mg/day to about 30 mg/day, about 5 mg/day to about 35 mg/day, about 5 mg/day to about 40 mg/day, about 5 mg/day to about 45 mg/day, about 5 mg/day to about 50 mg/day, about 5 mg/day to about 75 mg/day, or about 5 mg/day to about 100 mg/day.

Dosing can be single dosage or cumulative (serial dosing), and can be readily determined by one skilled in the art. For instance, treatment of a *Trypanosoma*-based disease may comprise a one-time administration of an effective amount of a *Trypanosoma* antigen and/or immunogenic composition herein. As a non-limiting example, an effective amount of a *Trypanosoma* antigen and/or immunogenic composition disclosed herein can be administered once to an individual, e.g., as a single injection or deposition. Alternatively, treatment of a *Trypanosoma*-based disease may comprise multiple administrations of an effective amount of a *Trypanosoma* antigen and/or immunogenic composition disclosed herein carried out over a range of time periods, such as, e.g., daily, once every few days, weekly, monthly or yearly. As a non-limiting example, a *Trypanosoma* antigen and/or immunogenic composition disclosed herein can be administered one, two, three, four, five or six times yearly to an individual. The timing of administration can vary from individual to individual, depending upon such factors as the severity of an individual's symptoms. For example, an effective amount of a *Trypanosoma* antigen and/or immunogenic composition disclosed herein can be administered to an individual once every three months for an indefinite period of time, or until the individual no longer requires therapy. A person of ordinary skill in the art will recognize that the condition of the individual can be monitored throughout the course of treatment and that the effective amount of a *Trypanosoma* antigen and/or immunogenic composition disclosed herein that is administered can be adjusted accordingly.

A composition comprising a *Trypanosoma* antigen and/or immunogenic composition disclosed herein can also be administered to an individual in combination with other therapeutic compounds to increase the overall therapeutic effect of the treatment. The use of multiple compounds to treat an indication can increase the beneficial effects while reducing the presence of side effects.

Aspects of the present specification can be described as follows:

1. A *Trypanosoma* antigen, wherein the *Trypanosoma* antigen comprises, consists essentially of or consists of SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12, or a peptide having 75% amino acid identity SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12, or a peptide, at least 7 contiguous amino acids from SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12.

2. The *Trypanosoma* antigen according to embodiment 1, wherein the peptide has 75% amino acid identity SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12 comprises at least 1 contiguous amino acid deletion, addition, and/or substitution relative to SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12.

3. The *Trypanosoma* antigen according to embodiment 1, wherein the peptide has 75% amino acid identity SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12 comprises at least 1 non-contiguous amino acid deletion, addition, and/or substitution relative to SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12.

4. The *Trypanosoma* antigen according to embodiment 1, wherein the peptide has 75% amino acid identity SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12 comprises at most 11 contiguous amino acid deletion, addition, and/or substitution relative to SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12.

5. The *Trypanosoma* antigen according to embodiment 1, wherein the peptide has 75% amino acid identity SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12 comprises at most 11 non-contiguous amino acid deletion, addition, and/or substitution relative to SEQ ID NO: 6, SEQ ID NO: 9, SEQ ID NO: 5, SEQ ID NO: 7, SEQ ID NO: 8, SEQ ID NO: 11, SEQ ID NO: 1, SEQ ID NO: 2, SEQ ID NO: 3, SEQ ID NO: 4, SEQ ID NO: 10 or SEQ ID NO: 12.

6. An immunogenic composition comprises, consists essentially of or consists of one or more *Trypanosoma* antigens as defined in any one of embodiments 1-5.

7. The immunogenic composition according to embodiment 6, wherein the one or more *Trypanosoma* antigens comprise, consist essentially of or consist of SEQ ID NO: 6 (CH47).

8. The immunogenic composition according to embodiment 6 or embodiment 7, wherein the one or more *Trypanosoma* antigens comprise, consist essentially of or consist of SEQ ID NO: 9 (CH77).

9. The immunogenic composition according to any one of embodiments 6-8, wherein the one or more *Trypanosoma* antigens comprise, consist essentially of or consist of SEQ ID NO: 5 (CH37).

10. The immunogenic composition according to embodiment 6, wherein the one or more *Trypanosoma* antigens comprise, consist essentially of or consist of SEQ ID NO: 5 (CH37) and SEQ ID NO: 9 (CH77).

11. The immunogenic composition according to embodiment 6, wherein the one or more *Trypanosoma* antigens comprise, consist essentially of or consist of SEQ ID NO: 5 (CH37), SEQ ID NO: 6 (CH 47) and SEQ ID NO: 9 (CH77).

12. The immunogenic composition according to any one of embodiments 6-11, wherein the one or more *Trypanosoma* antigens comprise, consist essentially of or consist of SEQ ID NO: 7 (CH 69), SEQ ID NO: 8 (CH72) and SEQ ID NO: 11 (CH84).

13. The immunogenic composition according to embodiment 6 or embodiment 7, wherein the one or more *Trypanosoma* antigens comprise, consist essentially of or consist of SEQ ID NO: 2 (CH30), SEQ ID NO: 7 (CH 69), SEQ ID NO: 8 (CH72), SEQ ID NO: 9 (CH 77) and SEQ ID NO: 11 (CH84).

14. The immunogenic composition according to embodiment 6 or embodiment 7, wherein the one or more *Trypanosoma* antigens comprise, consist essentially of or consist of SEQ ID NO: 2 (CH30), SEQ ID NO: 5 (CH37), SEQ ID NO: 7 (CH 69), SEQ ID NO: 8 (CH72), SEQ ID NO: 9 (CH 77) and SEQ ID NO: 11 (CH84).

15. The immunogenic composition according to embodiment 6, wherein the one or more *Trypanosoma* antigens comprise, consist essentially of or consist of SEQ ID NO: 2 (CH30), SEQ ID NO: 5 (CH37), SEQ ID NO: 6 (CH47), SEQ ID NO: 7 (CH 69), SEQ ID NO: 8 (CH72), SEQ ID NO: 9 (CH 77) and SEQ ID NO: 11 (CH84).

16. The immunogenic composition according to any one of embodiments 6-15, wherein the one or more *Trypanosoma* antigens are each present in an amount of between about 1 mg to about 1,000 mg.

17. The immunogenic composition according to any one of embodiments 6-16, wherein the immunogenic composition further comprises, consists essentially of or consists of one or more adjuvants.

18. The immunogenic composition according to embodiment 17, wherein the one or more adjuvants are each present in an amount of between about 100 μg/mL to about 1,500 μg/mL.

19. The immunogenic composition according to any one of embodiments 6-18, further comprising, consisting essentially of or consisting of one or more pharmaceutical acceptable carriers.

20. A method of treating a *Trypanosoma*-based disease, the method comprising, consisting essentially of or consisting of the step of administering to an individual in need thereof an immunogenic composition as defined in any one of embodiments 6-18 in an amount sufficient to reduce one or more physiological conditions or symptom associated with a *Trypanosoma* infection or pathology, thereby treating the *Trypanosoma*-based disease.

21. The method according to embodiment 20, wherein the administration of the immunogenic composition is in an amount sufficient to increase, induce, enhance, augment, promote or stimulate *Trypanosoma* clearance or removal, or decrease, reduce, inhibit, suppress, prevent, control, or limit transmission of *Trypanosoma* to another individual.

22. The method according to embodiment 20 or embodiment 21, wherein the administration of the immunogenic composition is in an amount sufficient to reduce, decrease, suppress, limit, control or inhibit *Trypanosoma* pathogen numbers or titer; reduce, decrease, suppress, limit, control or inhibit *Trypanosoma* pathogen proliferation or replication; reduce, decrease, suppress, limit, control or inhibit the amount of a *Trypanosoma* protein synthesized; or reduce, decrease, suppress, limit, control or inhibit the amount of a *Trypanosoma* pathogen nucleic acid replicated.

23. The method according to any one of embodiments 20-22, wherein the administration of the immunogenic composition reduces one or more physiological conditions or symptom associated with a *Trypanosoma* infection or pathology by at least 10%.

24. The method according to any one of embodiments 20-23, wherein the administration of the immunogenic composition reduces one or more physiological conditions or symptom associated with a *Trypanosoma* infection or pathology by at least one week.

25. The method according to any one of embodiments 20-24, wherein the *Trypanosoma*-based disease is a Chagas disease or an African sleeping sickness.

26. Use of an α-*Trypanosoma* antigen as defined in any one of embodiments 1-5 or immunogenic composition as defined in any one of embodiments 6-18 to treat a *Trypanosoma*-based disease.

27. A method of treating a *Trypanosoma*-based disease, the method comprising, consisting essentially of or consisting of the step of administering to an individual in need thereof a *Trypanosoma* antigen as defined in any one of embodiments 1-5 or an immunogenic composition as defined in any one of embodiments 6-19 in an amount sufficient to immunize or vaccinate the individual against the *Trypanosoma* infection or pathology, thereby treating the *Trypanosoma*-based disease.

28. A method of treating a *Trypanosoma*-based disease comprising, consisting essentially of or consisting of administering to an individual in need thereof a *Trypanosoma* antigen as defined in any one of embodiments 1-5 or an immunogenic composition as defined in any one of embodiments 6-19 in an amount sufficient to protect the individual against a *Trypanosoma* infection or pathology.

29. The method according to embodiment 27 or embodiment 28, wherein the administration of the *Trypanosoma* antigen or the immunogenic composition is in an amount sufficient to increase, induce, enhance, augment, promote or stimulate an immune response against a *Trypanosoma*.

30. The method according to any one of embodiments 27-29, wherein the administration of the *Trypanosoma* antigen or the immunogenic composition is in an amount sufficient to immunize or vaccinate the individual against the *Trypanosoma* infection or pathology.

31. The method according to any one of embodiments 27-30, wherein the administration of the *Trypanosoma* antigen or the immunogenic composition is in an amount sufficient to reduce, decrease, limit, control or inhibit susceptibility to a *Trypanosoma* infection or pathology.

32. The method according to any one of embodiments 27-31, wherein the administration of the *Trypanosoma* antigen or the immunogenic composition is in an amount sufficient to increase, induce, enhance, augment, promote or stimulate *Trypanosoma* clearance or removal, or decrease, reduce, inhibit, suppress, prevent, control, or limit transmission of *Trypanosoma* to another individual.

33. The method according to any one of embodiments 27-32, wherein the *Trypanosoma*-based disease is a Chagas disease or an African sleeping sickness.

34. Use of a *Trypanosoma* antigen as defined in any one of embodiments 1-5 for the manufacture of a medicament.

35. Use of an immunogenic composition as defined in any one of embodiments 6-18 for the manufacture of a medicament.

36. The use according to any one of embodiments 34 or 35, wherein the *Trypanosoma*-based disease is a Chagas disease or an African sleeping sickness.

EXAMPLES

The following non-limiting examples are provided for illustrative purposes only in order to facilitate a more complete understanding of the disclosed subject matter. These examples should not be construed to limit any of the embodiments described in the present specification, including those pertaining to *Trypanosoma* antigens and/or immunogenic compositions, or methods and uses for treating a *Trypanosoma*-based disease.

Example 1

Identification of *Trypanosoma* Peptides

A computer algorithm capable of predicting T cell reactive epitopes within protein sequences peptides was used to identify *Trypanosoma* antigens. In this in-silico model as many protein sequences as possible and from as many different strains were gathered from *Trypanosoma* pathogens. Available sequences for a particular protein were then aligned using Clustal and a consensus sequence was generated using Jalview. This sequence was then uploaded into the algorithm which predicted all possible T cell reactive epitopes. Peptide sequences from regions containing high number of epitopes were identified and these highly T-cell immunogenic regions were further analysed for conservation amongst the different strains. Conserved peptide sequences of between 20-40 amino acids in length in which consecutive amino acids share at least 70% sequence identity amongst all the other sequences found were selected and further analyzed. For example, in order to avoid inducing autoimmune reactions post-vaccination, these conserved peptide sequences were evaluated to confirm that these sequence did not share significant identity with other human and murine protein sequences. In addition, these conserved peptide sequences were evaluated to confirm these sequence could be synthetically manufactured by Fmoc chemistry.

Using this approach, a total of 452 peptides from different antigens were identified. These peptides were ranked based on the number of predicted epitopes and the top 100 peptides from this analysis were evaluated for feasibility of manufacture. Ultimately, 12 candidate peptides were identified according to the number of predicted epitopes they contained and according to the feasibility of their manufacture. Peptides having the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, were each manufactured by Fmoc chemistry (Bachem AG, Switzerland) in accordance with Good Manufacturing Practice (GMP). SEQ ID NO: 1 (CH9) is a 40 amino acid peptide corresponding to residues 60 to 99 of a paraflagelar rod protein from *Trypanosoma cruzi*. SEQ ID NO: 2 (CH30) is a 30 amino acid peptide corresponding to residues 1 to 30 of a ADP ribosylation factor 1 from *Trypanosoma cruzi*. SEQ ID NO: 3 (CH32) is a 32 amino acid peptide corresponding to residues 1 to 32 of a tryparedoxin protein from *Trypanosoma cruzi*. SEQ ID NO: 4 (CH36) is a 25 amino acid peptide corresponding to residues 564 to 588 of a glucose 6 phosphate isomerase protein from *Trypanosoma cruzi*. SEQ ID NO: 5 (CH37) is a 39 amino acid peptide corresponding to residues 564 to 588 of a pyruvate phosphate dikinase protein from *Trypanosoma cruzi*. SEQ ID NO: 6 (CH47) is a 34 amino acid peptide corresponding to residues 1 to 34 of a Tcp2b protein from *Trypanosoma cruzi*. SEQ ID NO: 7 (CH69) is a 35 amino acid peptide corresponding to residues 441 to 475 of a DNA topoisomerase 2 protein from *Trypanosoma cruzi*. SEQ ID NO: 8 (CH72) is a 30 amino acid peptide corresponding to residues 116 to 145 of a phosphoinositide-specific phospholipase C protein from *Trypanosoma cruzi*. SEQ ID NO: 9 (CH77) is a 33 amino acid peptide corresponding to residues 108 to 140 of a Dihydroorotate dehydrogenase protein from *Trypanosoma cruzi*.

SEQ ID NO: 10 (CH82) is a 36 amino acid peptide corresponding to residues 43 to 78 of a Histone H3 protein from *Trypanosoma cruzi*. SEQ ID NO: 11 (CH84) is a 33 amino acid peptide corresponding to residues 36 to 68 of an AGP2b2 protein from *Trypanosoma cruzi*. SEQ ID NO: 12 (CH93) is a 31 amino acid peptide corresponding to residues 514 to 544 of a Poly-A binding protein from *Trypanosoma cruzi*. These sequences were identified in silico through multiple sequence (ClustalW) and immunogenicity analysis of all *Trypanosoma* protein sequences available at the National Centre for Biotechnology Information (NCBI) database (January 2006). Each polypeptide represents a short region of high sequence conservation (≥70%) containing >5 human T-cell epitopes.

Example 2

Cytokine Response to Individual *Trypanosoma* Peptides

In vivo immunogenicity of the identified peptides was assessed by production of IFNγ in the splenocytes of vaccinated animals after in vitro exposure to the sequence, or peptides inducing high IgG2a titer. immunizing BALB/c mice with 10 nmol of each peptide on day 1, a booster on day 15 and isolation of spleens and terminal bleeds on day 21.

BALB/c mice barrier bred (i.e. pathogen free), 7-9 weeks old at the start of the study were divided into 3 groups with 6 animals each (3 males/3 females). BALB/c mice were chosen for this study since they provide a model for acute Chagas disease. Group A mice were administered a 10 nmol/peptide equimolar mixture of the following peptides: CH9 (SEQ ID NO: 1), CH30 (SEQ ID NO: 2). CH32 (SEQ ID NO: 3), CH36 (SEQ ID NO: 4), CH37 (SEQ ID NO: 5) and CH47 (SEQ ID NO: 6). Group B mice were administered a 10 nmol/peptide equimolar mixture of the following peptides: CH69 (SEQ ID NO: 7), CH72 (SEQ ID NO: 8), CH77 (SEQ ID NO: 9), CH82 (SEQ ID NO: 10) and CH84 (SEQ ID NO: 11). Group C mice were administered a 10 nmol/peptide equimolar mixture of non-related peptides as a control. All animals were immunised subcutaneously at the base of the tail on day 1 and received a booster on day 15. On day 21 all animals were culled and spleens and sera were harvested for analysis.

T cell responses were assessed by cytokine ELISA as follows. Mouse spleens were gently pressed through cell strainers and red blood cells were removed with red cell lysis buffer (nine parts 0.16 M $NH_4Cl$ and one part of 0.17 M Tris, pH 7.2). Splenocyte suspensions from each experimental group were plated in 96-well plates at a density of $4 \times 10^6$ cells/well in RPMI-1640 supplemented with 50 IU/50 µg/mL of penicillin/streptomycin and 10% FCS, and containing either media alone, Concanavalin A (Con A)(5 µg/mL), single polyepitope peptides at 2 µM. After 48 hours of incubation, the supernatant was collected and analysed for IFN-γ and IL-4 production using a mouse cytokine ELISA kit (BD Biosciences) to assess the induction of an immune response. The threshold of detection for the assays was 31.25 pg/mL for IFN-γ and 7.81 pg/mL for IL-4. Responses were plotted as the differential in cytokine production (pg/mL) between the groups immunised with the Chagas peptides and their respective controls. Animals in all groups reacted to Con A with IFN-γ levels above 1000 pg/mL and IL-4 levels above 200 pg/mL. No animals showed spontaneous proliferation with all media alone readings being below or around the threshold of detection for both IFN-γ and IL-4.

Figure 1B:
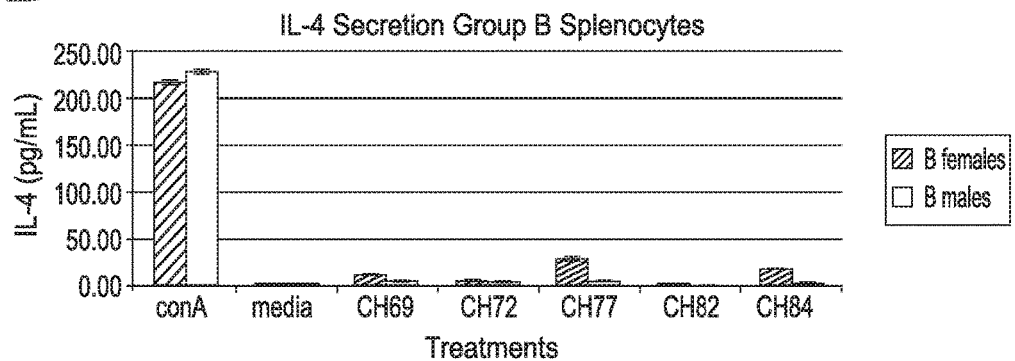
Figure 1C:
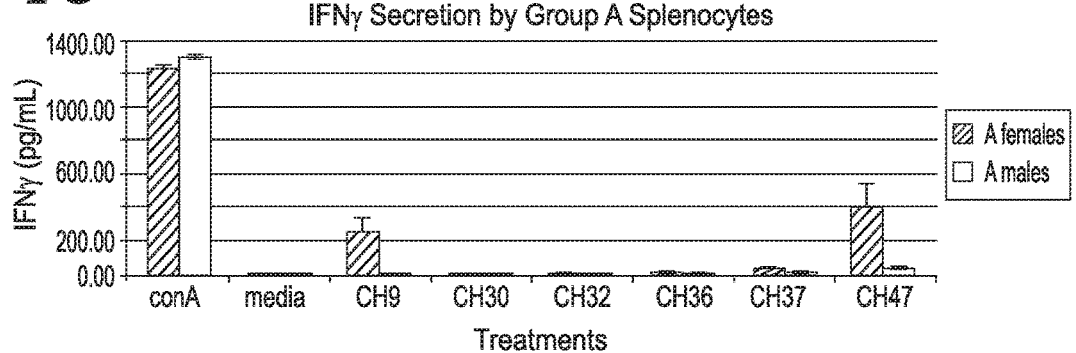
Figure 1D:
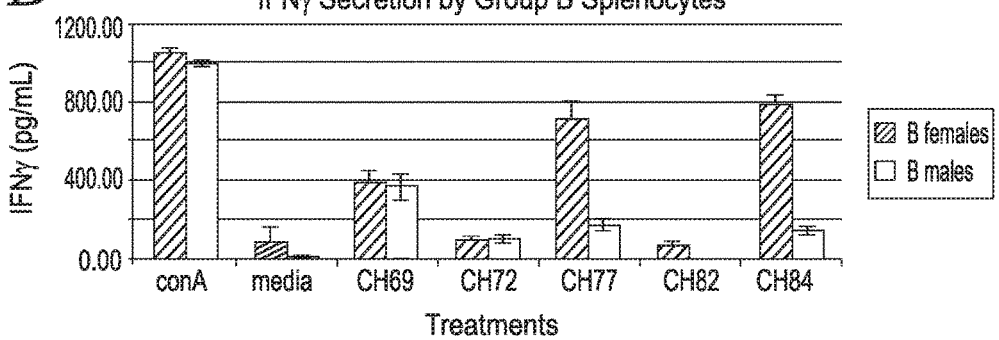

As expected, little or no IL-4 was secreted in response to the various peptides compared to the secretion observed with Con A non-specific stimulation of the splenocytes (FIGS. 1A & 1B). As for IFN-γ secretion, the results highlight the fact that females respond by secreting higher amounts of IFN-γ than males do. Peptides CH9, CH47, CH77, CH82 and CH84 induce IFN-γ secretion in females but not in males (FIGS. 1C & 1D). On the other hand CH72 induced similar moderate IFN-γ secretion in males than females and only CH69 induced a similar strong response in both sexes (FIG. 1D). These results are very interesting taking into account the different immune responses between males and females and the different susceptibility of the genders to *T. cruzi* infection. The production of IFN-γ by the splenocytes of vaccinated BALB/c mice after in vitro exposure to the recall antigen in the absence of IL-4 production clearly indicates that immunisation with the Chagas peptides induces a Th1 response. The absence of a response to CH30, CH32, CH36 and CH37 in BALB/c mice could reflect a significantly reduced rate of epitope generation from this sequence (i.e. the sequence is resistant to degradation).

To further analyze the immune response induced by vaccination with these peptides total Ig titers specific to each peptides were measured in the sera of the animals in all groups. ELISA 96-well plates were coated overnight at +4° C. with 2 µM of single Chagas peptides. Plates were washed twice with PBST (PBS with 0.05% TWEEN 20) and blocked for 1 hour with 1% BSA Fraction V in PBS. Plates were washed thrice with PBST before adding test sera samples at double decreasing dilutions from 1:100 to 1:3, 200 and incubating for 2 hours. After washing six times with PBST, wells were loaded with HRP-conjugated goat anti-mouse-Ig sera. After 1 hour incubation, plates were washed eight times with PBST, and TMB substrate was added. The reaction was stopped with 0.5 M $H_2SO_4$ and the absorbance of each well read at 450 nm.

Figure 2A:
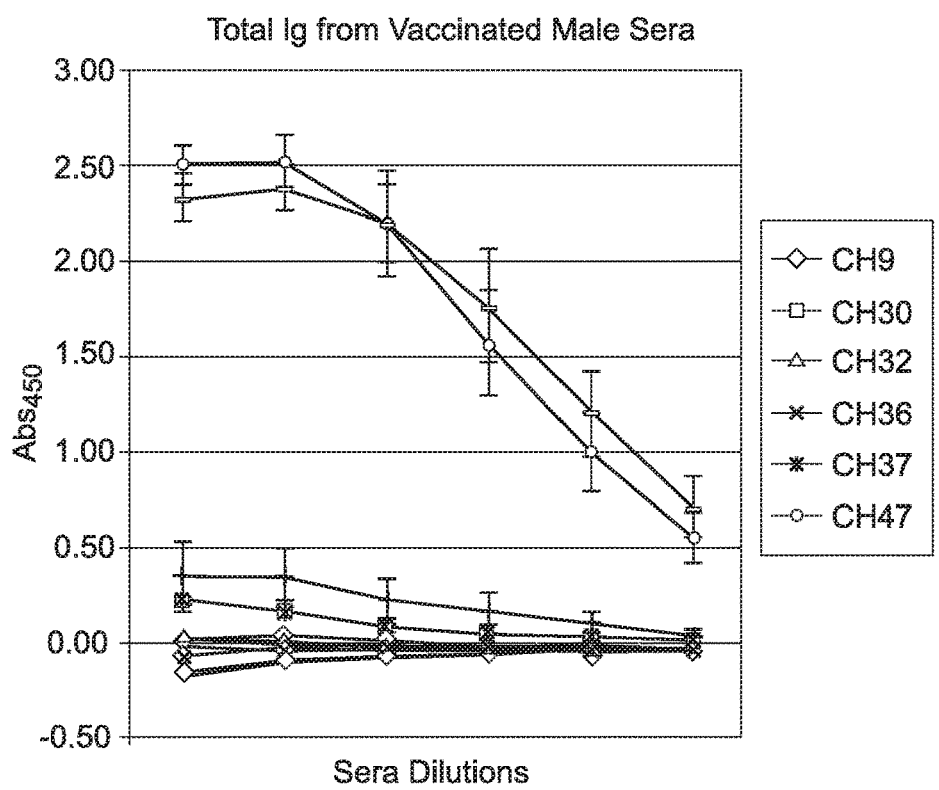
FIGS. 2A-B shows total immunoglobulin responses specific to individual peptides in serum of vaccinated mice with FIG. 2A showing total immunoglobulin responses in male animals.
Figure 2B:
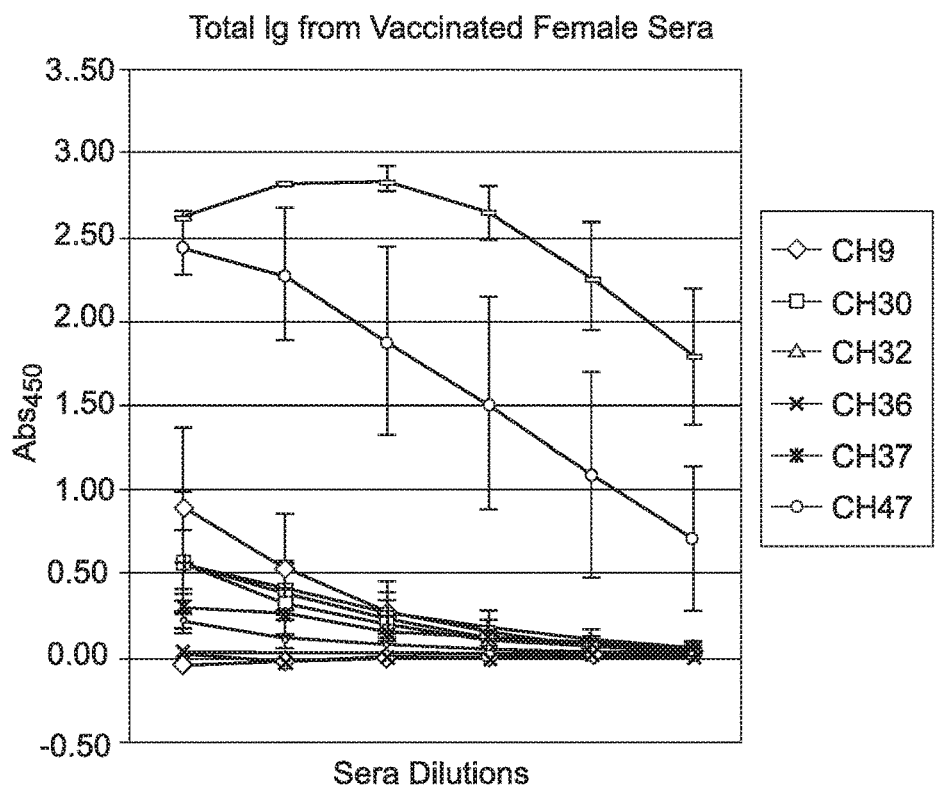
Figure 3B:
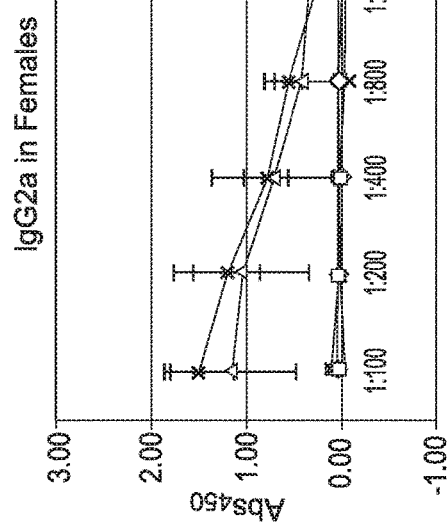
FIGS. 3A-D shows IgG1 and IgG2 responses specific to individual peptides in serum of vaccinated mice with FIG. 3A showing IgG2 responses in male animals.
Figure 3A:
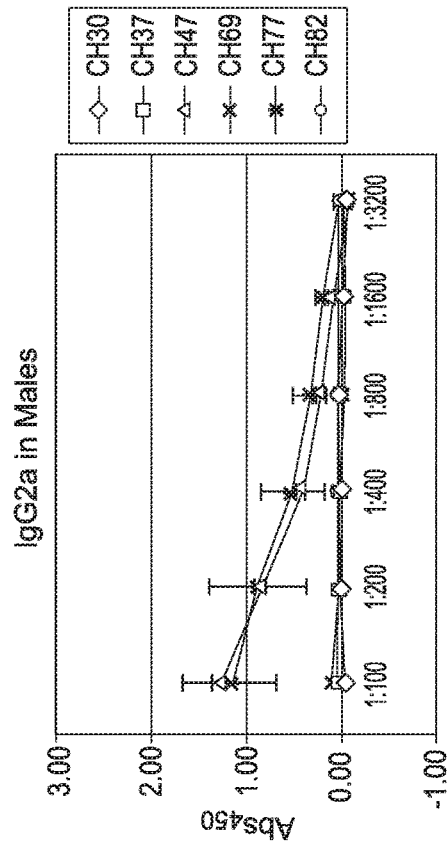
Figure 3D:
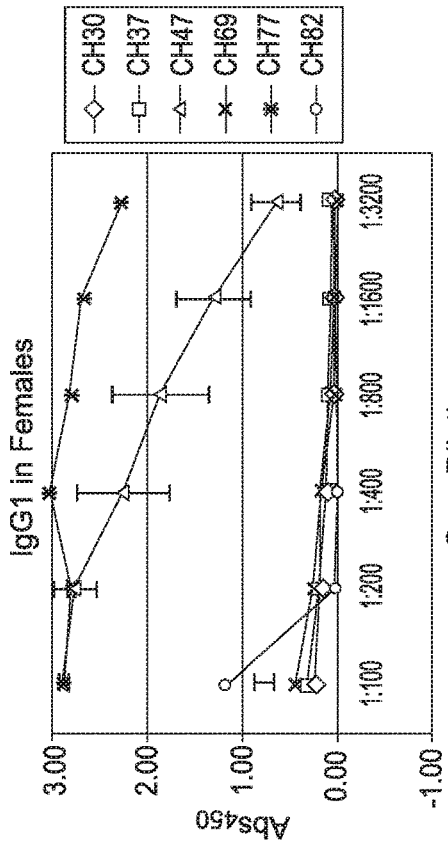
Figure 3C:
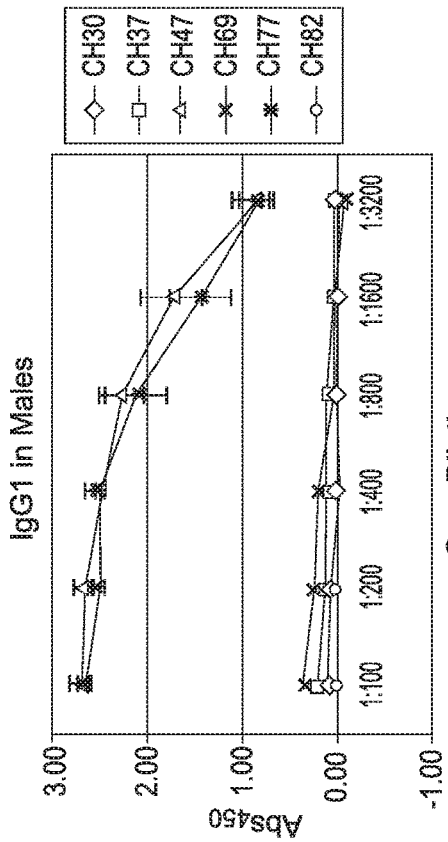

The results show a better antibody response in the vaccinated females versus the vaccinated males. Peptides CH47 and CH77 show the best antibody response in both genders, followed by CH69 inducing a lower antibody titer similar in both genders (FIGS. 2A & 2B).

To further dissect the antibody response, IgG1 and IgG2a antibodies specific to the peptides that showed strong antibody responses were measured. For that purpose ELISA 96-well plates were coated overnight at +4° C. with 2 µM of single Chagas peptides. Plates were washed twice with PBST and blocked for 1 hour with 1% BSA Fraction V in PBS. Plates were washed thrice with PBST before adding test sera samples for 2 hours. After washing six times with PBST, wells were loaded with either goat anti-mouse IgG1 or anti-mouse IgG2a. After 1 h incubation HRP-conjugated anti-goat IgG was added and incubated for a further 1 h. Plates were then washed eight times with PBST, and TMB substrate added for 30 minutes. The reaction was stopped with 0.5 M $H_2SO_4$ and the absorbance of each well read at 450 nm.

As seen in the graphs, peptides CH47 and CH77 exhibit a strong antibody response of both IgG2a and IgG1 (FIG. 3A-D). We cannot make assumptions on whether the antibody tends more towards a Th1 response (higher IgG2a) or a Th2 response (higher IgG1) since these ELISAs are not quantitative only qualitative.

Thus, the results of this Example show that in vivo testing of the newly synthesized Chagas peptides resulted identified a group of 6 peptides that demonstrated good in vivo immunogenicity and an induction of a significant Th1 response. For example, CH9, CH47, CH69, CH72, CH77 and CH84 showed strong production of IFN-γ in the splenocytes of vaccinated animals after in vitro exposure to the sequence while CH47 and CH77 also induced a good antibody response as shown by high IgG1 and IgG2a titers.

Example 3

Cytokine Response to *Trypanosoma* Peptides

To further test CH47 (SEQ ID NO: 6), CH69 (SEQ ID NO: 7), CH72 (SEQ ID NO: 8), CH77 (SEQ ID NO: 9), CH84 (SEQ ID NO: 11) as well as additional peptide CH93 (SEQ ID NO: 12), additional in vivo immunogenicity testing was performed. BALB/c mice barrier bred (i.e. pathogen free), 7-9 weeks old at the start of the study were divided into 4 groups with 6 animals each (3 males/3 females). Animals were administered a 0.2 mL composition comprising 0.1 mL of peptide mix of CH47, CH69, CH72, CH77, CH84 and CH93 in water emulsified with 0.1 mL of Montanide ISA-51 adjuvant as a subcutaneous injection on day 1 and on day 15. Group 1 was composed of three female mice receiving an equimolar concentration of 2.5 nmol for each peptide; Group 2 was composed of three male mice receiving an equimolar concentration of 2.5 nmol for each peptide; Group 3 was composed of three female mice receiving an equimolar concentration of 10 nmol for each peptide; and Group 4 was composed of three male mice receiving an equimolar concentration of 10 nmol for each peptide. Seven days after the last dose all animals were culled, terminally bled and spleens were harvested.

T cell responses were assessed by cytokine ELISA. Spleens of the same gender and group were pooled together and gently pressed through cell strainers and red blood cells were removed with red cell lysis buffer (nine parts 0.16 M $NH_4Cl$ and one part of 0.17 M Tris, pH 7.2). Isolated splenocyte suspensions from each experimental group were plated in 96-well plates at a density of $4 \times 10^5$ cells/well in RPMI-1640 supplemented with 50 IU/50 μg/mL of penicillin/streptomycin and 10% FCS, and containing either media alone, Concanavalin A (Con A)(5 μg/mL), single polyepitope peptides at 2 μM. After 48 hours of incubation, the supernatant was collected and analysed for IFN-γ and IL-4 production using a mouse cytokine ELISA kit (BD Biosciences) to assess the induction of an immune response. The cytokine detection threshold determined by the assay was 31.25 pg/mL for IFN-γ and 7.81 pg/mL for IL-4.

Figure 4A:
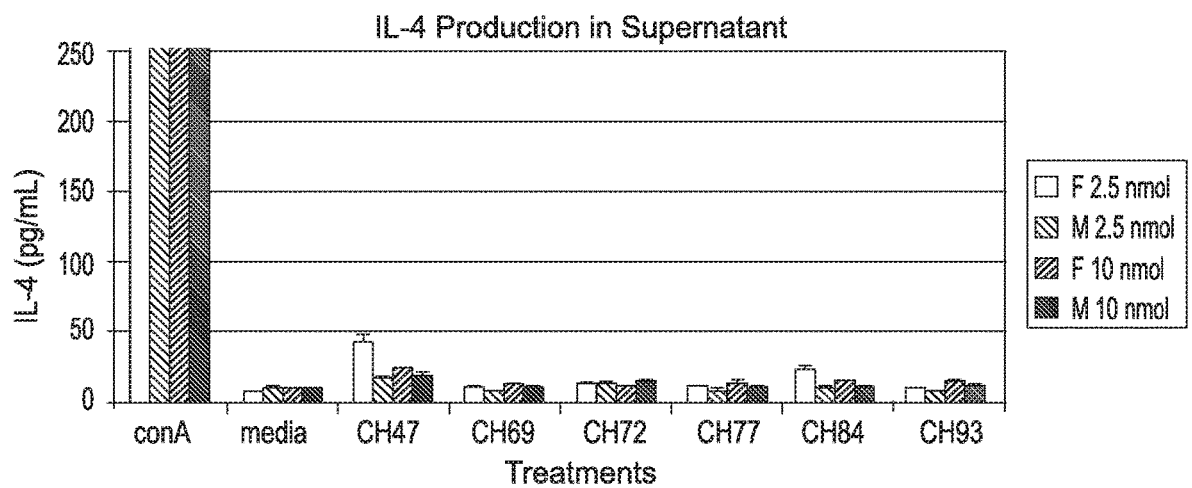
FIGS. 4A-B show the production of IL-4 and IFN-γ by splenocytes after 48 hour exposure to single peptides in vitro with FIG. 4A showing IL-4 production.
Figure 4B:
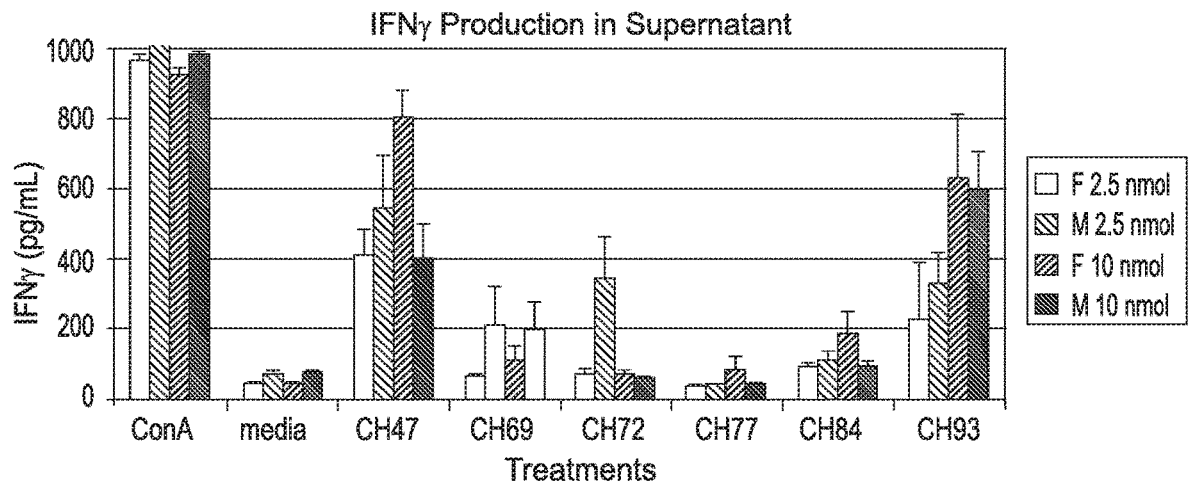

The results for IFN-γ and IL-4 secretion according to the dose received and the gender are shown in FIGS. 4A & 4B. As expected, little or no IL-4 was secreted in response to the various peptides compared to the secretion observed with Con A non-specific stimulation of the splenocytes (FIG. 4A). As for IFN-γ secretion, the two higher responders were peptides CH47 and CH93 (FIG. 4B). The IFN-γ response to CH69, CH77 and CH84 is lower in this study compared to previous studies (e.g. Example 2). A reason for this could be that peptides CH47 and CH93 are immunodominant, basically even though all peptides are administered in equimolar amounts, CH47 and CH93 are more efficient at binding to MHC and therefore highly represented compared to the rest of the peptides. In Example 2, peptides CH69, CH77 and CH84 were in a different group to CH47 and CH93 and therefore unaffected. There were no major differences in terms of cytokine expression between animals receiving a 2.5 nmol dose or a 10 nmol dose. Only CH93 showed a clear increase in IFN-γ production in both genders vaccinated with 2.5 nmol verses 10 nmol (FIG. 4B).

In order to ascertain whether the IFN-γ response observed is specific, we tested the single peptides in splenocytes from a different mouse strain (C57BLK6) that had not been vaccinated (naïve). A total of 10 spleens (5 males/5 females) were processed as previously explained and pooled as a single splenocyte suspension. Cells were seeded in 96 well plates at $4 \times 10^5$ cells/well in RPMI-1640 supplemented with 50 IU/50 μg/mL of penicillin/streptomycin and 10% FCS, and containing either media alone, Concanavalin A (Con A)(5 μg/mL), single polyepitope peptides at 2 μM. After 48 hours of incubation, the supernatant was collected and analysed for IFN-γ production using a mouse cytokine ELISA kit (BD Biosciences) to assess the induction of an immune response. The cytokine detection threshold determined by the assay for IFN-γ was 31.25 pg/mL.

Figure 5:
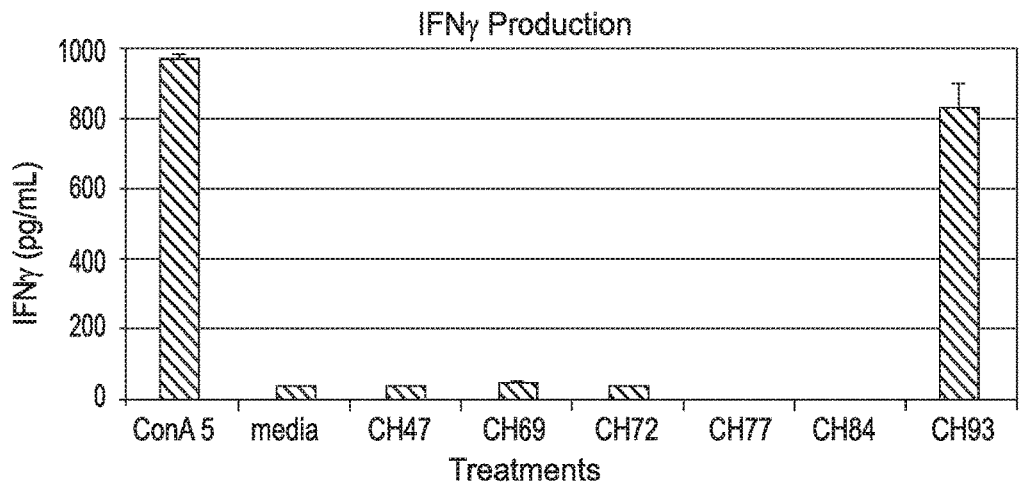
FIG. 5 shows the production of IFN-γ by splenocytes from naïve mice exposed to the single peptides.

The results indicate that the response obtained with CH93 is non-specific since splenocytes from naïve animals exposed to CH93 secrete very high levels of IFN-γ after 48 h incubation (FIG. 5). CH93 most likely stimulates the innate immunity through binding to Pattern Recognition Receptors such as TLR.

To further analyse the immune response induced by vaccination with these peptides total Ig titers were measured by ELISA on the sera samples from the different groups as follows. ELISA 96-well plates were coated overnight at +4° C. with 2 μM of single Chagas peptides. Plates were washed twice with PBST and blocked for 1 hour with 1% BSA Fraction V in PBS. Plates were washed thrice with PBST before adding test sera samples at double decreasing dilutions from 1:100 to 1:3,200 and incubating for 2 hours. After washing six times with PBST, wells were loaded with HRP-conjugated goat anti-mouse-Ig sera. After 1 hour incubation, plates were washed eight times with PBST, and TMB substrate was added. The reaction was stopped with 0.5 M $H_2SO_4$ and the absorbance of each well read at 450 nm.

Figure 6A:
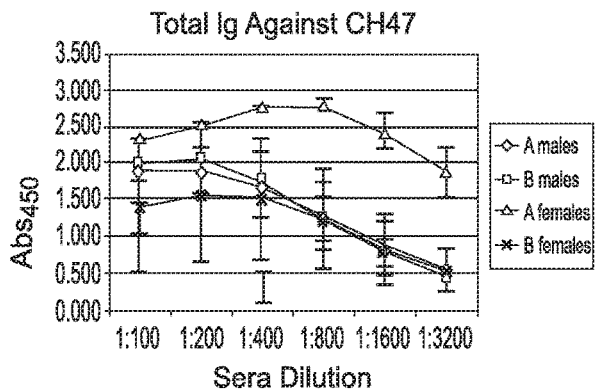
FIGS. 6A-F shows total Immunoglobulin responses specific to individual peptides in serum of vaccinated mice with FIG. 6A showing total immunoglobulin responses against CH47 in animals.
Figure 6B:
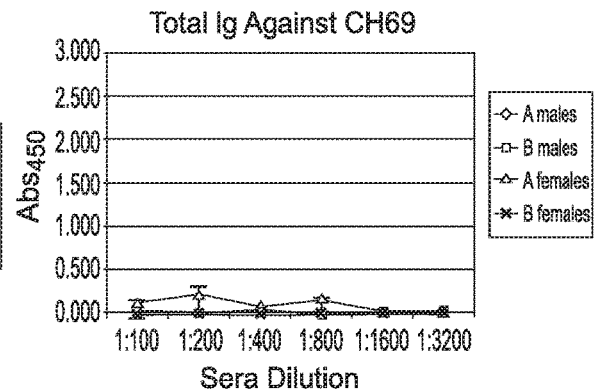
Figure 6C:
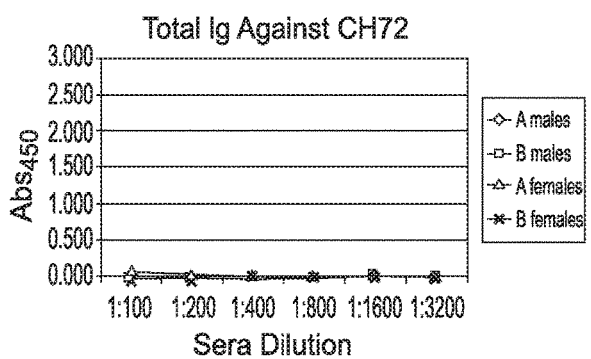
Figure 6D:
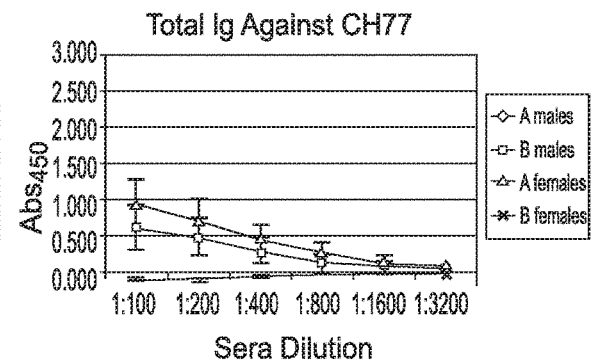
Figure 6E:
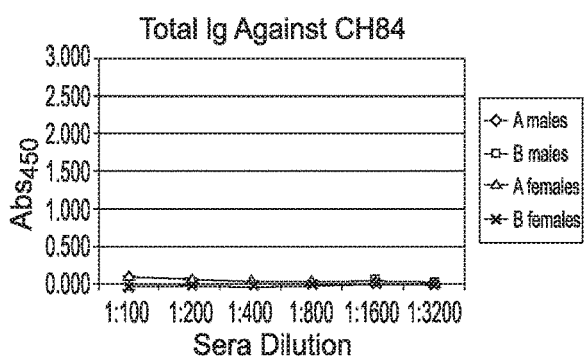
Figure 6F:
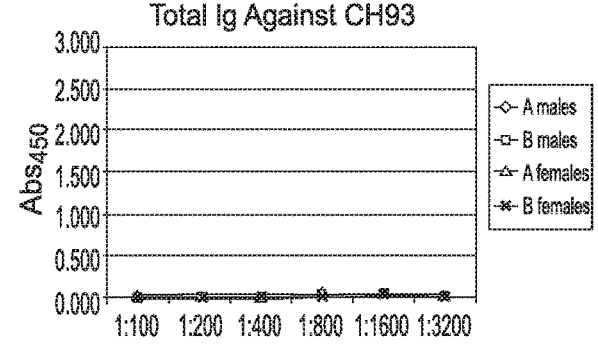

After analysing the ELISA results, CH47 shows an excellent response in males and females (FIG. 6A). This high response however dampens the antibody response of peptides CH69 and CH77 (FIGS. 6B & 6D) which in Example 2 showed a marked antibody response. CH93 did not induce an antibody response.

To further dissect the antibody response generated by CH47 and CH77, IgG1 and IgG2a antibodies specific to each single peptide were measured. For that purpose ELISA 96-well plates were coated overnight at +4° C. with 2 μM of single peptides. Plates were washed twice with PBST and blocked for 1 hour with 1% BSA Fraction V in PBS. Plates were washed thrice with PBST before adding test sera samples for 2 hours. After washing six times with PBST, wells were loaded with either goat anti-mouse IgG1 or anti-mouse IgG2a. After 1 hour incubation HRP-conjugated anti-goat IgG was added and incubated for a further 1 hour. Plates were then washed eight times with PBST, and TMB substrate added for 30 minutes. The reaction was stopped with 0.5 M $H_2SO_4$ and the absorbance of each well read at 450 nm.

Figure 7A:
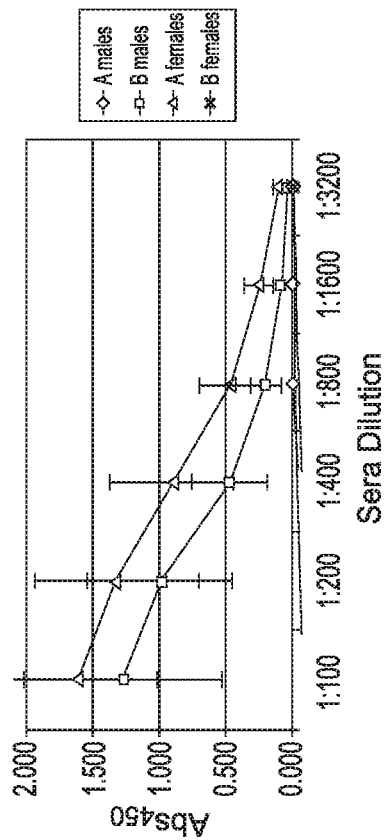
FIGS. 7A-D shows IgG1 and IgG2 responses specific to individual peptides in serum of vaccinated mice with FIG. 7A showing IgG1 responses against CH77 in animals.
Figure 7B:
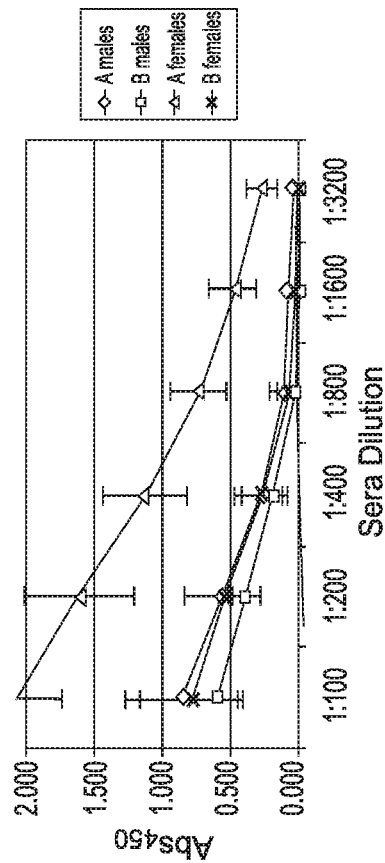
Figure 7C:
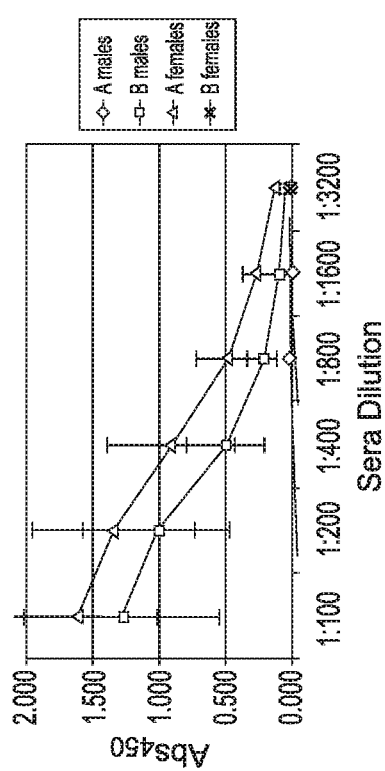
Figure 7D:
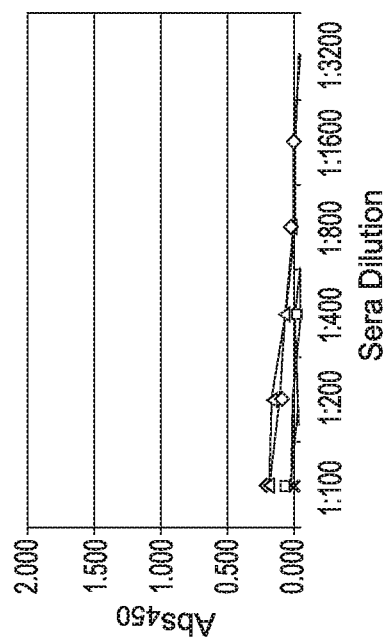
Figure 9A:
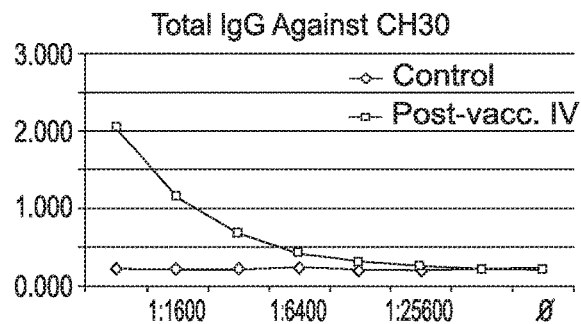
FIGS. 9A-H shows total Immunoglobulin responses specific to individual peptides in serum of vaccinated mice with FIG. 9A showing total immunoglobulin responses against CH30 in animals.
Figure 9B:
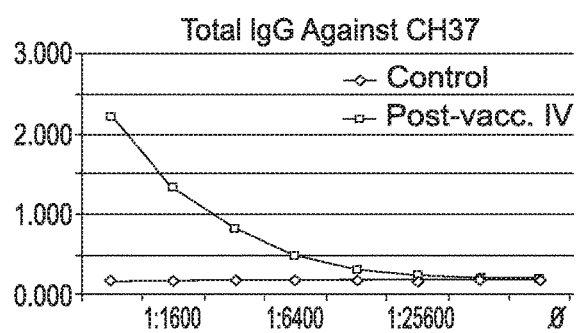
Figure 9C:
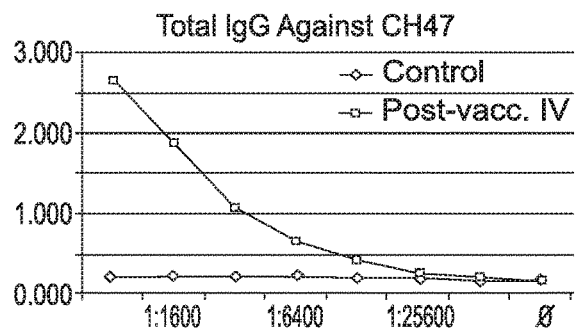
Figure 9D:
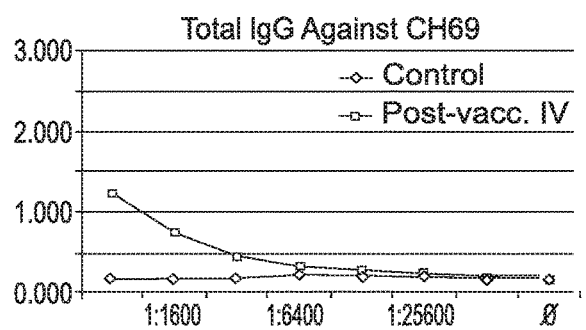
Figure 9E:
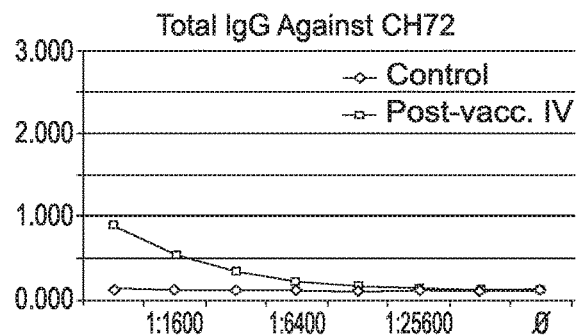
Figure 9F:
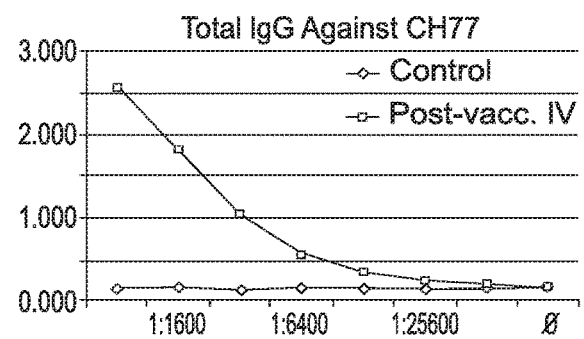
Figure 9G:
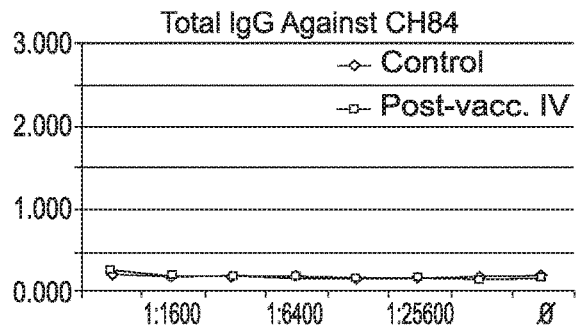
Figure 9H:
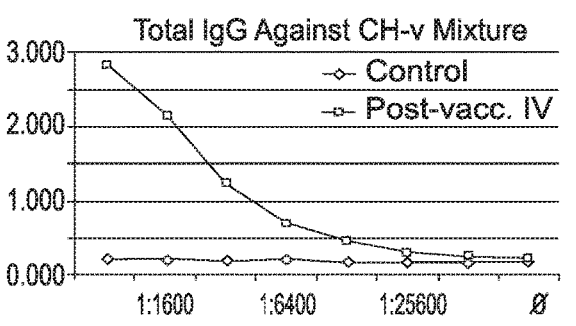

As seen in the FIG. 7A-D, peptides CH47 and CH77 exhibit a strong IgG1 antibody response which is characteristic of a Th2 response (FIGS. 7A & 7B). Interestingly, only CH47 is capable of inducing a strong IgG2a response (FIG. 7D), which is indicative of a Th1 response in mice.

Example 4

Immunodominance of CH47

In order to test the effect of CH47 on the immunogenicity of other peptides, the other peptides tested together with CH47 (as disclosed in Examples 2 and 3) were split into two groups and mice were vaccinated with peptides in group 1 or in group 2 on day 1. Then each group was split into A and B, and on day 14, subgroups A received a dose of the same peptides received on day 1, whereas subgroups B received the peptides as on day 1 plus CH47. The dosage regimes were as follows: Group 1A, 10 nmol of each of CH9, CH30, CH32, CH36 and CH37 on day 1 and day 14; Group 1B, 10 nmol of each of CH9, CH30, CH32, CH36 and CH37 on day 1, and on day 14 the same peptide combination plus 10 nmol of CH47; Group 2A, 10 nmol of each of CH69, CH72, CH77, CH82 and CH84 on day 1 and day 14; and Group 2B, 10 nmol of each of CH69, CH72, CH77, CH82 and CH84 on day 1, and on day 14 the same combination of peptides plus 10 nmol of CH47.

The study was carried out in BALB/c mice, barrier bred (i.e. pathogen free), 7-9 weeks old at the start of the study. Each of the 4 groups included 4 animals (2 males/2 females). All animals received 2 doses of 0.2 mL composition (0.1 mL of peptide mix in water emulsified with 0.1 mL of Montanide ISA-51 adjuvant) as a subcutaneous injection on day 1 and on day 14. Spleen and serum samples were analysed as described in Examples 2 and 3.

The Table 3 indicates the IL-4 production (pg/mL) in supernatants of splenocyte cultures according to the dose received and the gender. Little IL-4 is produced in response to any of the peptides tested compared to the response obtained with Concanavalin A (ConA).

TABLE 3

IL-4 production (pg/mL) in supernatants of splenocyte cultures

| | | Group 1 Peptides | | | | | | |
|---|---|---|---|---|---|---|---|---|
| Group | Gender | CH9 | CH30 | CH32 | CH36 | CH37 | Media | ConA |
| 1A | F | <7.80 ± *0.12* | <7.80 ± *2.03* | <7.80 ± *0.29* | <7.80 ± *0.00* | 9.13 ± *1.70* | <7.80 ± *0.92* | 416.63 ± *9.83* |
|  | M | <7.80 ± *0.00* | <7.80 ± *0.56* | <7.80 ± *0.00* | <7.80 ± *0.00* | <7.80 ± *0.53* | <7.80 ± *0.00* | 342.46 ± *14.60* |
| 1B | F | <7.80 ± *0.39* | <7.80 ± *0.00* | <7.80 ± *0.00* | <7.80 ± *0.00* | 9.13 ± *0.00* | <7.80 ± *0.00* | 393.67 ± *1.17* |
|  | M | <7.80 ± *0.00* | <7.80 ± *0.00* | <7.80 ± *0.00* | <7.80 ± *0.00* | <7.80 ± *1.69* | <7.80 ± *0.00* | 223.45 ± *5.22* |
| 2A | F | <7.80 ± *0.00* | <7.80 ± *0.00* | <7.80 ± *0.00* | <7.80 ± *0.00* | 9.13 ± *0.00* | <7.80 ± *0.00* | 408.81 ± *1.29* |
|  | M | <7.80 ± *0.00* | <7.80 ± *0.00* | <7.80 ± *0.00* | <7.80 ± *0.00* | <7.80 ± *0.00* | <7.80 ± *0.00* | 224.51 ± *5.54* |
| 2B | F | <7.80 ± *0.00* | <7.80 ± *0.00* | <7.80 ± *0.00* | 9.49 ± *1.59* | <7.80 ± *0.00* | <7.80 ± *0.00* | 500.00 ± *0.00* |
|  | M | <7.80 ± *0.00* | <7.80 ± *1.76* | <7.80 ± *0.00* | 8.19 ± *2.24* | 13.55 ± *3.09* | <7.80 ± *0.00* | 312.01 ± *9.21* |

| | | Group 2 Peptides | | | | | | |
|---|---|---|---|---|---|---|---|---|
| Group | Gender | CH69 | CH72 | CH77 | CH82 | CH84 | Media | ConA |
| 1A | F | <7.80 ± *0.67* | <7.80 ± *0.25* | <7.80 ± *0.00* | <7.80 ± *0.00* | <7.80 ± *0.00* | <7.80 ± *0.92* | 416.63 ± *9.83* |
|  | M | <7.80 ± *0.00* | <7.80 ± *0.00* | <7.80 ± *0.00* | <7.80 ± *0.00* | <7.80 ± *0.00* | <7.80 ± *0.00* | 342.46 ± *14.60* |
| 1B | F | <7.80 ± *0.00* | <7.80 ± *0.00* | <7.80 ± *0.00* | <7.80 ± *0.00* | <7.80 ± *0.00* | <7.80 ± *0.00* | 393.67 ± *1.17* |
|  | M | <7.80 ± *0.00* | <7.80 ± *0.00* | <7.80 ± *0.00* | <7.80 ± *0.00* | <7.80 ± *0.00* | <7.80 ± *0.00* | 223.45 ± *5.22* |
| 2A | F | <7.80 ± *0.00* | <7.80 ± *0.00* | <7.80 ± *0.00* | <7.80 ± *0.00* | <7.80 ± *0.00* | <7.80 ± *0.00* | 408.81 ± *1.29* |
|  | M | <7.80 ± *0.00* | <7.80 ± *0.00* | <7.80 ± *0.00* | <7.80 ± *0.00* | <7.80 ± *0.00* | <7.80 ± *0.00* | 224.51 ± *5.54* |
| 2B | F | 10.02 ± *2.81* | <7.80 ± *1.24* | 13.61 ± *3.20* | <7.80 ± *0.90* | 19.28 ± *4.66* | <7.80 ± *0.00* | 500.00 ± *0.00* |
|  | M | 19.84 ± *0.87* | 10.30 ± *1.05* | 16.09 ± *0.92* | <7.80 ± *0.00* | 24.42 ± *1.88* | <7.80 ± *0.00* | 312.01 ± *9.21* |

Standard error of three replicates represented in italics.
M: males,
F: females.

The Table 4 indicates the IFN-γ production (pg/mL) in supernatants of splenocyte cultures according to the dose received and the gender. Peptides CH30, CH69, CH72, CH77 and CH84 (marked in black box) induced a moderate to good IFN-γ response that was increased by having CH47 in the booster vaccine preparation. CH9 and CH32 induced strong production of IFN-γ but it was non-specific since it was high even in splenocytes from animals not vaccinated with the peptides. This non-specific response is most likely due to their low solubility and particulated nature.

TABLE 4

IFN-γ production (pg/mL) in supernatants of splenocyte cultures

| | | Group 1 Peptides | | | | | | |
|---|---|---|---|---|---|---|---|---|
| Group | Gender | CH9 | CH30 | CH32 | CH36 | CH37 | Media | ConA |
| 1A | F | 847.37 ± *152.63* | 122.83 ± *51.11* | 113.25 ± *72.30* | 31.25 ± *0.00* | 69.67 ± *23.12* | 43.58 ± *12.33* | >1000 ± *0.00* |
|  | M | 975.09 ± *17.84* | 45.59 ± *14.34* | 189.68 ± *154.09* | 31.25 ± *0.00* | 31.25 ± *0.00* | 31.25 ± *0.00* | >1000 ± *0.00* |
| 1B | F | >1000 ± *0.00* | 225.46 ± *133.57* | 139.36 ± *83.07* | 23.98 ± *7.27* | 57.73 ± *16.76* | 40.73 ± *9.48* | >1000 ± *0.00* |
|  | M | 891.32 ± *108.68* | 144.91 ± *53.07* | 583.19 ± *432.73* | 195.63 ± *164.38* | 38.76 ± *7.51* | 32.76 ± *1.51* | >1000 ± *0.00* |
| 2A | F | 702.67 ± *164.09* | 31.56 ± *0.310* | 39.50 ± *8.25* | 31.25 ± *0.00* | 31.25 ± *0.00* | 31.25 ± *0.00* | >1000 ± *0.00* |
|  | M | >1000 ± *0.00* | 31.25 ± *0.00* | 539.54 ± *256.36* | 51.44 ± *14.03* | 84.81 ± *53.56* | 31.25 ± *0.00* | >1000 ± *0.00* |

TABLE 4-continued

| | | IFN-γ production (pg/mL) in supernatants of splenocyte cultures | | | | | | |
|---|---|---|---|---|---|---|---|---|
| 2B | F | >1000 ± *0.00* | 31.25 ± *0.00* | 539.89 ± *260.11* | 137.64 ± *88.25* | 31.25 ± *0.00* | 34.23 ± *2.98* | >1000 ± *0.00* |
| | M | 910.43 ± *89.57* | 31.25 ± *0.00* | 299.76 ± *119.18* | 81.58 ± *50.33* | 31.25 ± *0.00* | 31.25 ± *0.00* | >1000 ± *0.00* |

| | | Group 2 Peptides | | | | | | |
|---|---|---|---|---|---|---|---|---|
| Group | Gender | CH69 | CH72 | CH77 | CH82 | CH84 | Media | ConA |
| 1A | F | 31.25 ± *0.00* | 31.25 ± *0.00* | 31.25 ± *0.00* | 39.17 ± *7.92* | 31.25 ± *0.00* | 43.58 ± *12.33* | >1000 ± *0.00* |
| | M | 31.25 ± *0.00* | 31.25 ± *0.00* | 31.25 ± *0.00* | 31.25 ± *0.00* | 31.25 ± *0.00* | 31.25 ± *0.00* | >1000 ± *0.00* |
| 1B | F | 31.25 ± *0.00* | 31.25 ± *0.00* | 31.25 ± *0.00* | 31.25 ± *0.00* | 184.60 ± *153.35* | 40.73 ± *9.48* | >1000 ± *0.00* |
| | M | 31.25 ± *0.00* | 31.25 ± *0.00* | 31.25 ± *0.00* | 31.25 ± *0.00* | 33.16 ± *1.91* | 32.76 ± *1.51* | >1000 ± *0.00* |
| 2A | F | 54.37 ± *23.12* | 31.25 ± *0.00* | 74.30 ± *43.05* | 31.25 ± *0.00* | 48.71 ± *13.10* | 31.25 ± *0.00* | >1000 ± *0.00* |
| | M | 40.52 ± *9.27* | 42.05 ± *10.80* | 77.01 ± *30.80* | 76.10 ± *32.45* | 69.51 ± *23.34* | 31.25 ± *0.00* | >1000 ± *0.00* |
| 2B | F | 574.33 ± *436.07* | 110.71 ± *22.75* | 87.40 ± *17.45* | 31.25 ± *0.00* | 483.74 ± *261.91* | 34.23 ± *2.98* | >1000 ± *0.00* |
| | M | 736.59 ± *263.41* | 105.54 ± *57.63* | 87.76 ± *7.95* | 37.59 ± *6.34* | 91.80 ± *30.51* | 31.25 ± *0.00* | >1000 ± *0.00* |

Standard error of three replicates represented in italics.
M: males,
F: females.

As for the antibody responses, CH37 and CH77 are both capable of inducing antibody responses (Table 5). Table 5 shows the antibody titer (abs 450 nm-570 nm) at 1:400 dilution of the sera. CH77 has consistently showed high levels of antibody response in all studies carried out. We had never measured such a strong antibody response for CH37 because in past studies CH37 had always been used in a peptide combination including CH47 and therefore its antibody response was silenced by CH47.

TABLE 5

| | | Total Ig specific to peptide | | | | | | | | | |
|---|---|---|---|---|---|---|---|---|---|---|---|
| | | Peptides | | | | | | | | | |
| Group | Gender | CH9 | CH30 | CH32 | CH36 | CH37 | CH69 | CH72 | CH77 | CH82 | CH84 | Blank |
| 1A | M | 0.107 | 0.046 | 0.057 | 0.047 | 0.064 | 0.063 | 0.040 | 0.078 | 0.057 | 0.072 | 0.056 |
| | F | 0.190 | 0.065 | 0.067 | 0.157 | 2.465 | 0.064 | 0.057 | 0.095 | 0.084 | 0.102 | 0.085 |
| 1B | M | 0.152 | 0.095 | 0.067 | 0.073 | 2.151 | 0.058 | 0.063 | 0.088 | 0.068 | 0.087 | 0.088 |
| | F | 0.140 | 0.136 | 0.058 | 0.050 | 0.771 | 0.044 | 0.047 | 0.075 | 0.068 | 0.068 | 0.055 |
| 2A | M | 0.142 | 0.049 | 0.054 | 0.051 | 0.053 | 0.057 | 0.040 | 1.904 | 0.053 | 0.088 | 0.056 |
| | F | 0.212 | 0.117 | 0.095 | 0.093 | 0.175 | 0.084 | 0.078 | 0.710 | 0.110 | 0.137 | 0.106 |
| 2B | M | 0.197 | 0.062 | 0.070 | 0.063 | 0070 | 0.151 | 0.097 | 2.952 | 1.059 | 0.176 | 0.070 |
| | F | 0.188 | 0.071 | 0.080 | 0.067 | 0.174 | 0.068 | 0.061 | 1.639 | 0.077 | 0.091 | 0.076 |

To further dissect the antibody response generated by CH37 and CH77, IgG1 and IgG2a antibodies specific to each single peptide were measured (FIG. 8A-D). Results are expressed as relative absorbance where the absorbance of the control groups has been subtracted from the test group. As seen in FIG. 8A-D, the IgG1 titer is higher than the IgG2a titer for both CH37 and CH77. IgG2a responses tend to be associated with activation of complement and ADCC responses against infected cells, whereas IgG1 antibodies may bind to available antigens on the surface of extracellular trypanosomas inducing neutralising responses.

To summarise, the results indicate that a single dose of CH47 in the booster increases both cytokine and antibody responses. From the list of peptides tested we felt that the vaccine should consist of CH37 and CH77 for their antibody response and CH30, CH69, CH72 and CH84 for their IFN-γ response, plus CH47 in the booster vaccination to potentiate the effects of the other peptides.

Example 5

Rabbit Antiserum

To generate antibodies against the disclosed Chaga peptides in rabbits two male New Zealand Rabbits weighing about 3 Kg each were used. One was terminally bled at the beginning of the study in order to collect blood that was used as negative control. The other male was immunised using the following schedule. On Day 0 the animal received a 600 μL subcutaneous injection of an immunogenic composition. The Day 0 immunogenic composition was made by emulsifying a 300 μL peptide mixture including 30 nmol of each of CH30, CH37, CH69, CH72, CH77 and CH84 dissolved in water and with 300 μL Montanide ISA-51 adjuvant (Seppic). On Day 14 the animal received another 600 μL subcutaneous injection of an immunogenic composition. The Day 14 immunogenic composition was made by emulsifying a 300 μL peptide mixture including 30 nmol of each of CH30, CH37, CH69, CH72, CH77, CH84 and CH47 dissolved in water and with 300 μL Montanide ISA-51 adjuvant (Seppic). On Day 28 the animal received a third 600 μL subcutaneous injection of an immunogenic composition. The Day 14 immunogenic composition was made by emulsifying a 300 μL peptide mixture including 30 nmol of each of CH30, CH37, CH69, CH72, CH77 and CH84 dissolved in water and with 300 μL Montanide ISA-51 adjuvant (Seppic). On Day 42 the animal received a fourth 600 μL subcutaneous injection of an immunogenic composition. The Day 42 immunogenic composition was made by emulsifying a 300 μL peptide mixture including 30 nmol of each of CH30, CH37, CH69, CH72, CH77, CH84 and CH47 dissolved in water and with 300 μL Montanide ISA-51 adjuvant (Seppic). A 0.5 mL blood sample was obtained from the animal on Day 0 (prevaccination), Day 14, Day 25 (11 days after second immunisation), Day 39 (7 days after third immunisation) and Day 67 (25 days after fourth immunisation on culling day). Blood was left to clot at room temperature and sera was collected and analysed for antibody responses.

To assess the immune response induced by these immunogenic compositions total Ig titers were measured by ELISA on the sera samples from the different groups as follows. Wells of ELISA 96-well plates was individually coated with 2 μM of one of the Chagas peptides overnight at +4° C. Plates were washed twice with PBST and blocked for 1 hour with 1% BSA Fraction V in PBS. Plates were washed thrice with PBST before adding a 180 μL sera sample at double decreasing dilutions from 1:100 to 1:3,200 and incubating for 2 hours. After washing four times with PBST, wells were loaded with HRP-conjugated goat anti-rabbit-Ig sera. After 1 hour incubation in the dark, plates were washed six times with PBST, and 100 μL of a TMB substrate was added and the plates were incubated for 30 minutes at ambient temperature in the dark. The reaction was stopped with 50 μL of 0.5 M $H_2SO_4$. Absorbance of each well was read at 450 nm and background subtracted by reading absorbance at 570 nm.

The FIGS. 9A-H show the level of IgG on Day 67, 25 days after receiving the fourth immunisation. Peptides CH30, CH37, CH47 and CH77 each individually elicited a strong immunogenic response as compared to both the negative control sera as well as the total peptide mixture. Peptides CH69 and CH72 also individually elicited a good immunogenic response.

Example 6

Vaccine Efficacy in a *Trypanosoma* Murine Challenge

Figure 10:
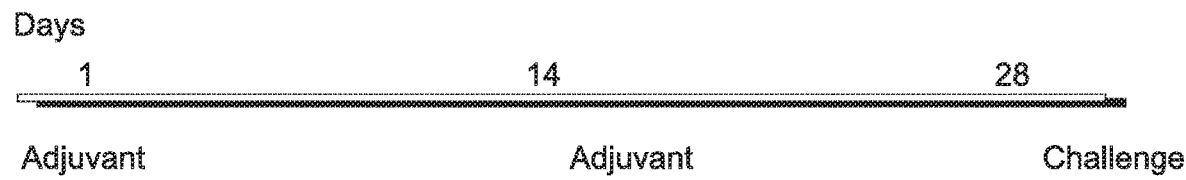
FIG. 10 shows the dosing regime for groups A, B, C and D.
Figure 10:
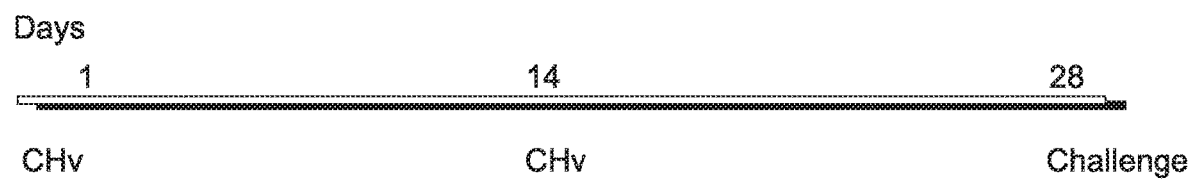
Figure 10:
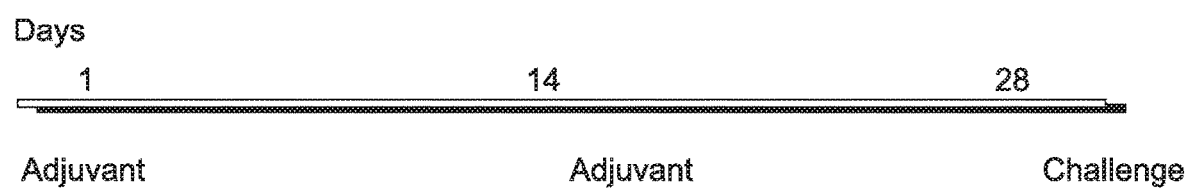
Figure 10:
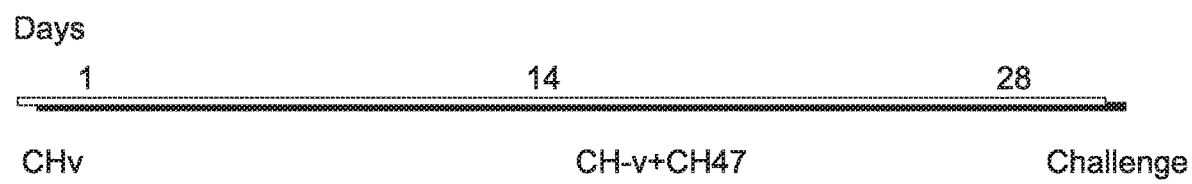

To examine the use of the *Trypanosoma* antigens disclosed herein as a prophylactic vaccine against Chagas, a vaccine composition was tested in BALB/cJ mice, 2 months of age. The composition, designated CH-v, comprised the adjuvant Montanide ISA-51 (Seppic) and the following peptides: CH30, CH37, CH69, CH72, CH77 and CH84. An additional composition consisting of CH-v plus CH47 was also used. Immunizations were carried out on male BALB/cJ mice, 2 months of age. Animals were first acclimatized to the installations of the BSL-3 laboratory prior to immunization. Immunizations were carried out as depicted in FIG. 10.

Immunized animals were challenged with *Trypanosoma cruzi* bloodstream trypomastigotes, strain RA (evolutionary lineage/typing unit=TcVI) (Risso, et al, J Infect Dis 189: 2250, 2004) animals received 50 trypomastigotes through intraperitoneal injection (IP). The RA strain is maintained by serial passages in male CF1 mice at the Institute's animal facilities. Another plasma sample was obtained and stored from each mouse after immunization, and before the challenge. The presence of circulating parasites was evaluated by counting parasites from a drop of blood (30 fields at 400× under light microscopy) at 10, 13 and 40 days post-infection (dpi). From 16 dpi onwards, parasitemia was determined by counting parasites in a hemocytometer (Neubauer), starting from 5 ul of peripheral blood mixed with 45 ul of a lytic solution (to lyse red blood cells). Values are expressed as number of parasites per ml. Mortality was followed up daily.

Figure 11:
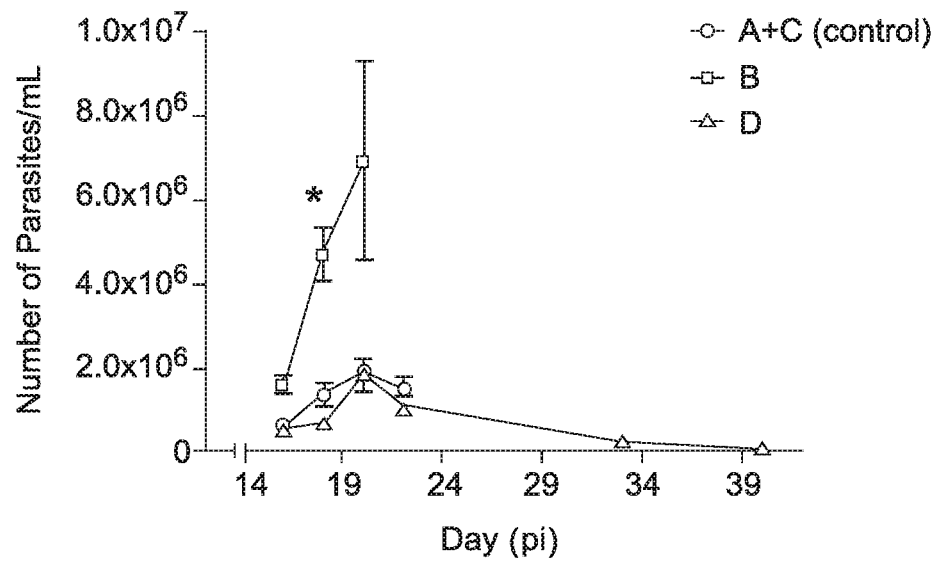
FIG. 11 shows parasitemia in control (A+C) and vaccinated (B and D) animal groups post-*Trypanosoma* infection (pi=post infection).

Parasitemia data for all groups were determined. Significant differences were observed at 18 dpi in group B verses Control (A+C) in the number of parasites (p<0.00014) (FIG. 11). Surprisingly, the number of parasites in the animals vaccinated with CH-v alone (group B) exceeded the number of parasites in the control group.

Figure 12:
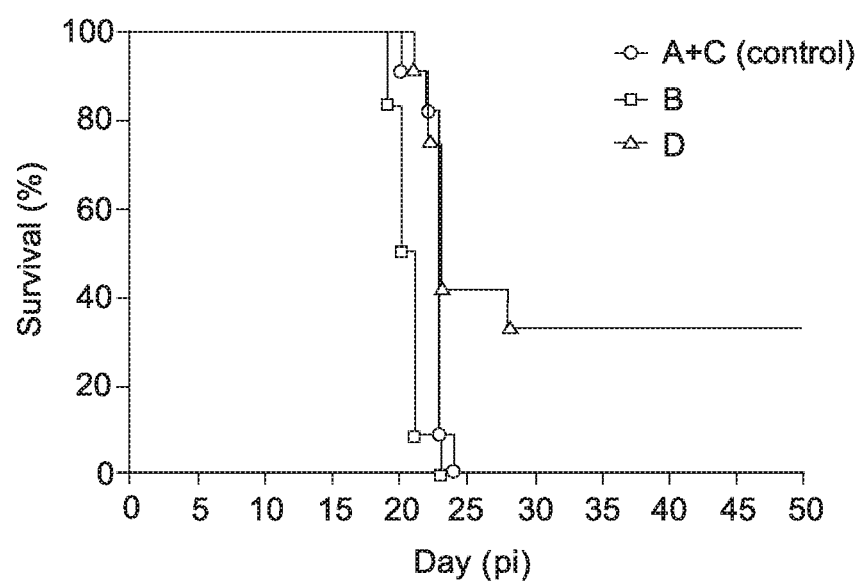
FIG. 12 shows mortality in control (A+C) and vaccinated (B and D) animal groups post-*Trypanosoma* infection (pi=post infection).

Mortality data for all groups were determined (FIG. 12). Interestingly, 40% of the animals in group D (CH-v in combination with CH47) survived the challenge after 25 days post-challenge and 33% remained alive by day 50. The analysis was performed using Student's test (parasitemia values), ANOVA followed by Bonferroni and Gehan-Breslow-Wilcoxon (GraphPad Software). Significant differences in mortality were also identified: B verses Control (A+C), p<0.0005; D verses Control (A+C), p<0.0394 (FIG. 11). The results obtained showed that animals immunized with the CH-v (group B) developed a higher parasitemia, which correlated with the early mortality observed in this group. This suggests that either this mixture, or one of its components, could be acting as a modulatory factor that negatively influences the outcome of the host response, leading to the observed faster mortality. Parasitemia values in animals from group D (CH-v in combination with CH47) were similar to those observed in control mice, in spite of this, mortality at 27 dpi was reduced to 58.3% and to 66.7% by day 40 dpi, whereas controls reached 100% mortality at 24 dpi. Overall, the results suggest that the inclusion of peptide CH47 in the booster received by animals vaccinated with CH-v is important to elicit a protective immune response. It is also important to notice that the effect of this peptide may be counteracting the negative effects induced by the CH-v mixture on the immune response.

The model of infection with the RA strain of *T. cruzi* represents a tough challenge for the vaccine candidates being evaluated, because it causes 100% mortality as well as alteration and destruction of the tissue architecture of spleen, thymus and ganglia. Maintenance of this strain by serial passage in mice favors the conservation of biological features of this strain, such as its virulence, which is attenuated when cultured in vitro.

Example 7

Vaccine Efficacy in a *Trypanosoma* Murine Challenge

Figure 13:
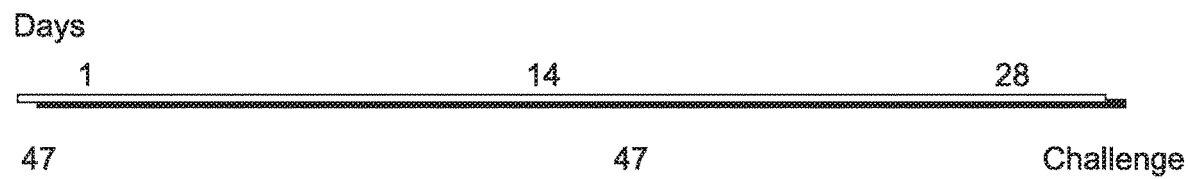
FIG. 13 shows the dosing regime for groups A, B and C.
Figure 13:
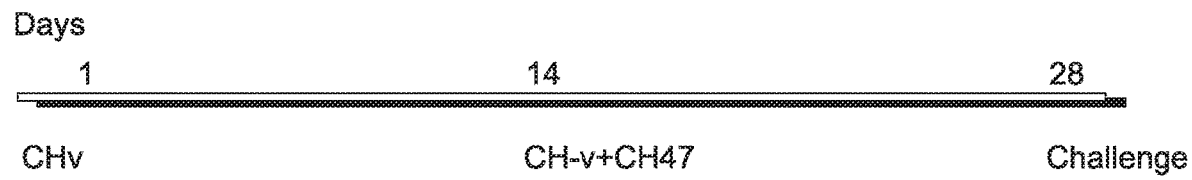
Figure 13:
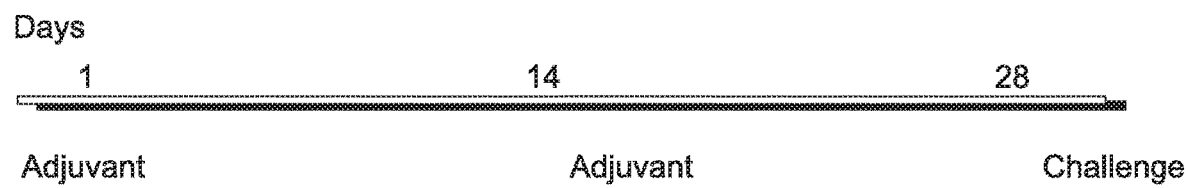

To examine the efficacy of CH-v in combination with CH47 or CH47 alone (two doses) as prophylactic vaccine against Chagas, a vaccine composition was tested in BALB/cJ mice, 2 months of age. The study consisted of three groups (A, B and C) each containing 12 male BALB/cJ mice, 2 months of age. As represented in FIG. 13, animals in group A received two doses of adjuvanted CH47 alone on days 1 and day 14. Animals in group B received adjuvanted CH-v (CH30, CH37, CH69, CH72, CH77, CH84) on day 1 followed by adjuvanted CH-v in combination with CH47 on day 14. Group C (control) received an emulsion of water and Montanide ISA-51 adjuvant as a subcutaneous dose on day 1 and day 14.

Immunized animals were challenged with *Trypanosoma cruzi* bloodstream trypomastigotes, strain RA (evolutionary lineage/typing unit=TcVI) (Risso, et al, J Infect Dis 189: 2250, 2004) animals received 50 trypomastigotes through intraperitoneal injection (IP). The RA strain is maintained by serial passages in male CF1 mice at the Institute's animal facilities. Parasitemia was determined by counting parasites in a hemocytometer (Neubauer), starting from 5 µL of peripheral blood mixed with 45 µL of a lytic solution (to lyse red blood cells). Values are expressed as number of parasites per ml. Mortality was followed up daily.

Figure 14:
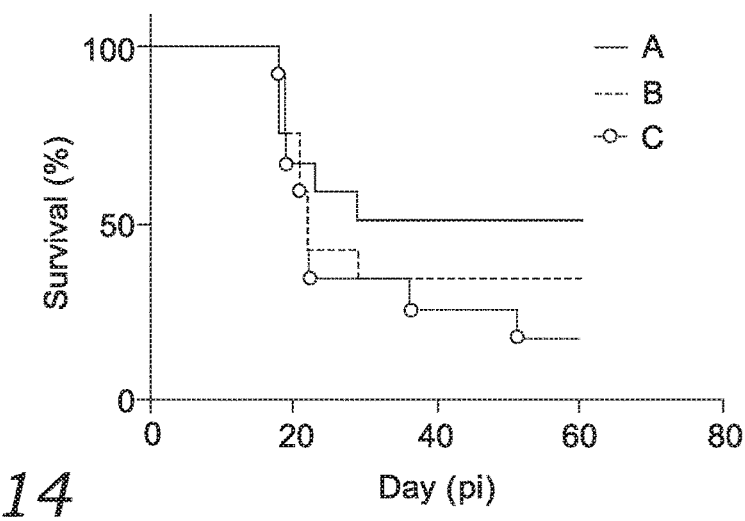
FIG. 14 shows mortality in control (C) and vaccinated (A and B) animal groups post-*Trypanosoma* infection (pi=post infection).

As seen on FIG. 14, the survival rates obtained with CH-v in combination with CH47 are very similar to those obtained in study 1 (33.3%). Surprisingly, survival in group immunized with only CH47 experienced higher survival with only 50% of the animals succumbing to the infection compared to 83.5% in the control group 60 days after a lethal *Trypanosoma* challenge.

Figure 15:
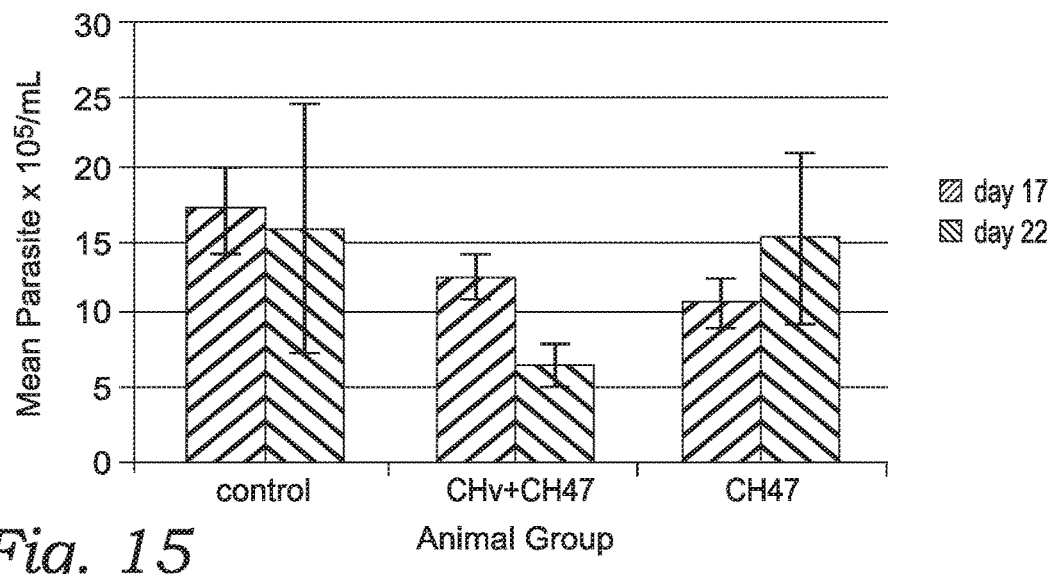
FIG. 15 shows mean parasitemia concentration and standard error in all groups at day 17 and day 22 post-challenge. Units are number of parasites×$10^5$/mL blood.
Figure 16:
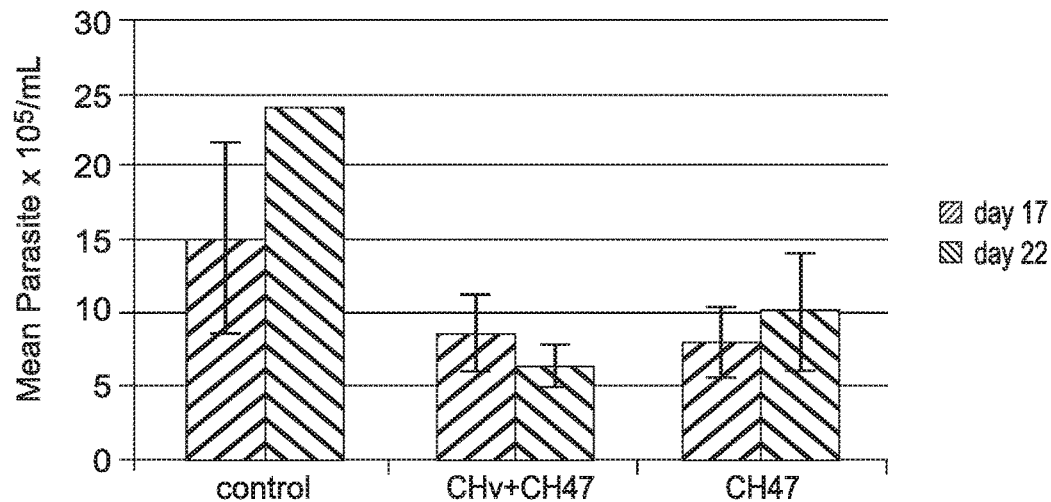
FIG. 16 shows mean parasitemia concentration and standard error in all groups at day 17 and day 22 post-infection in animals that survived at least day 25 post-challenge. Units are number of parasites×$10^5$/mL blood.

Parasitemia at day 17 was reduced in both vaccinated groups compared to the control group. Surviving animals in group CH-v+CH47 experienced further reduction in parasitemia on day 22 (FIG. 15). However, looking at the parasitemia at day 17 and day 22 post-challenge of those animals that survived past day 25, parasitemia is reduced in both vaccinated groups compared to the control group (FIG. 16). The most likely explanation is that the animals that survived the acute infection in the control group entered the chronic infection rather than clear infection.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A trypanosome antigen consisting of the amino acid sequence of SEQ ID NO: 6.

2. An immunogenic composition comprising one or more trypanosome antigens and one or more adjuvants, wherein the one or more trypanosome antigens comprise the amino acid sequence of SEQ ID NO: 6, or a peptide having at least 80% sequence identity to the amino acid sequence of SEQ ID NO: 6 or fragments thereof, wherein a fragment is at least 7 and at most 34 amino acids in length, or a peptide of at most 34 amino acids and having at least 7 contiguous amino acids from the amino acid sequence of SEQ ID NO: 6.

3. The immunogenic composition according to claim 2, wherein the one or more trypanosome antigens comprise the amino acid sequence of SEQ ID NO: 6.

4. The immunogenic composition according to claim 3, wherein the one or more trypanosome antigens further comprise the amino acid sequence of SEQ ID NO: 2, or a peptide having at least 80% amino acid identity to the amino acid sequence of SEQ ID NO: 2, or a peptide of at most 30 amino acids and having at least 7 contiguous amino acids from the amino acid sequence of SEQ ID NO: 2, the amino acid sequence of SEQ ID NO: 7, or a peptide having at least 80% amino acid identity to the amino acid sequence of SEQ ID NO: 7, or a peptide of at most 35 amino acids and having at least 7 contiguous amino acids from the amino acid sequence of SEQ ID NO: 7, the amino acid sequence of SEQ ID NO: 8, or a peptide having at least 80% amino acid identity to the amino acid sequence of SEQ ID NO: 8, or a peptide of at most 30 amino acids and having at least 7 contiguous amino acids from the amino acid sequence of SEQ ID NO: 8, the amino acid sequence of SEQ ID NO: 9, or a peptide having at least 80% amino acid identity to the amino acid sequence of SEQ ID NO: 9, or a peptide of at most 33 amino acids and having at least 7 contiguous amino acids from the amino acid sequence of SEQ ID NO: 9, and the amino acid sequence of SEQ ID NO: 11, or a peptide having at least 80% amino acid identity to the amino acid sequence of SEQ ID NO: 11, or a peptide of at most 33 amino acids and having at least 7 contiguous amino acids from the amino acid sequence of SEQ ID NO: 11.

5. The immunogenic composition according to claim 2, wherein the one or more trypanosome antigens further comprise the amino acid sequence of SEQ ID NO: 2, or a peptide having at least 80% amino acid identity to the amino acid sequence of SEQ ID NO: 2, or a peptide of at most 30 amino acids and having at least 7 contiguous amino acids from the amino acid sequence of SEQ ID NO: 2, the amino acid sequence of SEQ ID NO: 5, or a peptide having at least 80% amino acid identity to the amino acid sequence of SEQ ID NO: 5, or a peptide of at most 39 amino acids and having at least 7 contiguous amino acids from the amino acid sequence of SEQ ID NO: 5, the amino acid sequence of SEQ ID NO: 7, or a peptide having at least 80% amino acid identity to the amino acid sequence of SEQ ID NO: 7, or a peptide of at most 35 amino acids and having at least 7 contiguous amino acids from the amino acid sequence of SEQ ID NO: 7, the amino acid sequence of SEQ ID NO: 8, or a peptide having at least 80% amino acid identity to the amino acid sequence of SEQ ID NO: 8, or a peptide of at most 35 amino acids and having at least 7 contiguous amino acids from the amino acid sequence of SEQ ID NO: 8, the amino acid sequence of SEQ ID NO: 9, or a peptide having at least 80% amino acid identity to the amino acid sequence of SEQ ID NO: 9, or a peptide of at most 30 amino acids and having at least 7 contiguous amino acids from the amino acid sequence of SEQ ID NO: 9, and the amino acid sequence of SEQ ID NO: 11, or a peptide having at least 80% amino acid identity to the amino acid sequence of SEQ ID NO: 11, or a peptide of at most 33 amino acids and having at least 7 contiguous amino acids from the amino acid sequence of SEQ ID NO: 11.

6. The immunogenic composition according to claim 2, wherein the one or more trypanosome antigens further comprise the amino acid sequence of SEQ ID NO: 9, or a peptide having at least 80% amino acid identity to the amino acid sequence of SEQ ID NO: 9, or a peptide of at most 33 amino acids and having at least 7 contiguous amino acids from the amino acid sequence of SEQ ID NO: 9.

7. The immunogenic composition according to claim 2, wherein the one or more trypanosome antigens further comprise the amino acid sequence of SEQ ID NO: 5, or a peptide having at least 80% amino acid identity to the amino acid sequence of SEQ ID NO: 5, or a peptide of at most 39 amino acids and having at least 7 contiguous amino acids from the amino acid sequence of SEQ ID NO: 5.

8. The immunogenic composition according to claim 2, wherein the one or more trypanosome antigens further comprise the amino acid sequence of SEQ ID NO: 5, or a peptide having at least 80% amino acid identity to the amino acid sequence of SEQ ID NO: 5, or a peptide of at most 39 amino acids and having at least 7 contiguous amino acids from the amino acid sequence of SEQ ID NO: 5 and the amino acid sequence of SEQ ID NO: 9, or a peptide having at least 80% amino acid identity to the amino acid sequence of SEQ ID NO: 9, or a peptide of at most 33 amino acids and having at least 7 contiguous amino acids from the amino acid sequence of SEQ ID NO: 9.

9. The immunogenic composition according to claim 2, wherein the one or more trypanosome antigens further comprise the amino acid sequence of SEQ ID NO: 5, the amino acid sequence of SEQ ID NO: 6 and the amino acid sequence of SEQ ID NO: 9, respectively.

10. The immunogenic composition according to claim 3, wherein the one or more trypanosome antigens further comprise the amino acid sequence of SEQ ID NO: 7, or a peptide having at least 80% amino acid identity to the amino acid sequence of SEQ ID NO: 7, or a peptide of at most 35 amino acids and having at least 7 contiguous amino acids from the amino acid sequence of SEQ ID NO: 7, the amino acid sequence of SEQ ID NO: 8, or a peptide having at least 80% amino acid identity to the amino acid sequence of SEQ ID NO: 8, or a peptide of at most 30 amino acids and having at least 7 contiguous amino acids from the amino acid sequence of SEQ ID NO: 8, and the amino acid sequence of SEQ ID NO: 11, or a peptide having at least 80% amino acid identity to the amino acid sequence of SEQ ID NO: 11, or a peptide of at most 33 amino acids and having at least 7 contiguous amino acids from the amino acid sequence of SEQ ID NO: 11.

11. The immunogenic composition according to claim 2, wherein the one or more trypanosome antigens further comprise the amino acid sequence of SEQ ID NO: 2, the amino acid sequence of SEQ ID NO: 5, the amino acid sequence of SEQ ID NO: 6, the amino acid sequence of SEQ ID NO: 7, the amino acid sequence of SEQ ID NO: 8, the amino acid sequence of SEQ ID NO: 9 and the amino acid sequence of SEQ 10 NO: 11, respectively.

12. The immunogenic composition according to claim 2, wherein the one or more trypanosome antigens are each present in an amount of between about 1 mg to about 1,000 mg.

13. The immunogenic composition according to claim 2, wherein the one or more adjuvants are each present in an amount of between about 100 µg/mL to about 1,500 µg/mL.

14. The immunogenic composition according to claim 2, further comprising one or more pharmaceutical acceptable carriers.

* * * * *

SEQUENCE LISTING

```
<160> NUMBER OF SEQ ID NOS: 12

<210> SEQ ID NO 1
<211> LENGTH: 40
<212> TYPE: PRT
<213> ORGANISM: Artificial Sequence
<220> FEATURE:
<223> OTHER INFORMATION: Peptide fragment from Trypanosoma cruzi

<400> SEQUENCE: 1

Ala Gly Ile Arg Ser Ile Leu Arg Thr Leu Gln Glu Thr Arg Thr Gln
1               5                   10                  15

Leu Pro Arg Gly Arg Phe Leu Leu Met Arg Asp Asn Leu Ser Ala Leu
            20                  25                  30

Lys Pro His Gln Pro Pro Asp Leu
        35                  40

<210> SEQ ID NO 2
<211> LENGTH: 30
<212> TYPE: PRT
<213> ORGANISM: Artificial Sequence
<220> FEATURE:
<223> OTHER INFORMATION: Peptide fragment from Trypanosoma cruzi ADP
      ribosylation factor 1

<400> SEQUENCE: 2

Met Gly Gln Trp Leu Ala Ser Ala Phe Lys Ser Leu Leu Gly Lys Gln
1               5                   10                  15
```

Glu Val Arg Ile Leu Met Val Gly Leu Asp Ala Ala Gly Lys
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Peptide fragment from Trypanosoma cruzi

<400> SEQUENCE: 3

Met Leu Pro Arg Val Leu Gly Ala Gly Thr Leu Glu Leu Leu Arg Gln
1               5                   10                  15

Asp Gly Ser Asn Val Thr Ala Ser Lys Ala Leu Gln Gly Lys Lys Tyr
            20                  25                  30

<210> SEQ ID NO 4
<211> LENGTH: 25
<212> TYPE: PRT
<213> ORGANISM: Artificial Sequence
<220> FEATURE:
<223> OTHER INFORMATION: Peptide fragment from Trypanosoma cruzi

<400> SEQUENCE: 4

Asp Gln Trp Gly Val Glu Leu Gly Lys Leu Leu Ala Lys Ser Ile Leu
1               5                   10                  15

Pro Gln Leu Gln Pro Gly Gln Lys Val
            20                  25

<210> SEQ ID NO 5
<211> LENGTH: 39
<212> TYPE: PRT
<213> ORGANISM: Artificial Sequence
<220> FEATURE:
<223> OTHER INFORMATION: Peptide fragment from Trypanosoma cruzi
      pyruvate phosphate dikinase

<400> SEQUENCE: 5

Ser Arg Ile Asp Ala Ile Arg Glu Met Ile Leu Ala Asp Thr Leu Glu
1               5                   10                  15

Gly Arg Lys Ala Ala Ile Gln Lys Leu Leu Pro Val Gln Arg Gly Asp
            20                  25                  30

Phe Leu Gly Ile Phe Arg Thr
        35

<210> SEQ ID NO 6
<211> LENGTH: 34
<212> TYPE: PRT
<213> ORGANISM: Artificial Sequence
<220> FEATURE:
<223> OTHER INFORMATION: Peptide fragment from Trypanosoma cruzi acidic
      ribosomal P1 protein Tcp2b

<400> SEQUENCE: 6

Met Lys Tyr Leu Ala Ala Tyr Ala Leu Val Gly Leu Ser Gly Gly Thr
1               5                   10                  15

Pro Ser Lys Ser Ala Val Glu Ala Val Leu Lys Ala Ala Gly Val Pro
            20                  25                  30

Val Asp

<210> SEQ ID NO 7
<211> LENGTH: 35
<212> TYPE: PRT
<213> ORGANISM: Artificial Sequence

```
<220> FEATURE:
<223> OTHER INFORMATION: Peptide fragment from Trypanosoma cruzi DNA
      topoisomerase 2

<400> SEQUENCE: 7

Ser Ala Lys Ala Leu Ala Gln Asn Ser Leu Ser Ser Asp Gln Lys Arg
1               5                   10                  15

Tyr Thr Gly Val Phe Pro Leu Arg Gly Lys Leu Leu Asn Val Arg Asn
            20                  25                  30

Lys Asn Leu
        35

<210> SEQ ID NO 8
<211> LENGTH: 30
<212> TYPE: PRT
<213> ORGANISM: Artificial Sequence
<220> FEATURE:
<223> OTHER INFORMATION: Peptide fragment from Trypanosoma cruzi
      phosphoinositide-specific phospholipase C

<400> SEQUENCE: 8

Ser Leu Arg Glu Leu Gly Lys Leu Val Lys Gly Leu Asn Phe Pro Ala
1               5                   10                  15

Asp Leu Ser Lys Gln Leu Ile Ala Ala Val Lys Ala Ala Gly
            20                  25                  30

<210> SEQ ID NO 9
<211> LENGTH: 33
<212> TYPE: PRT
<213> ORGANISM: Artificial Sequence
<220> FEATURE:
<223> OTHER INFORMATION: Peptide fragment from Trypanosoma cruzi
      dihydroorotate dehydrogenase

<400> SEQUENCE: 9

Asn Val Ala Met Val Arg Arg Leu Ala Pro Val Ala Gln Glu Lys Gly
1               5                   10                  15

Val Leu Leu Glu Leu Asn Leu Ser Cys Pro Asn Val Pro Gly Lys Pro
            20                  25                  30

Gln

<210> SEQ ID NO 10
<211> LENGTH: 36
<212> TYPE: PRT
<213> ORGANISM: Artificial Sequence
<220> FEATURE:
<223> OTHER INFORMATION: Peptide fragment from Trypanosoma cruzi

<400> SEQUENCE: 10

Val Ala Leu Arg Glu Ile Arg Gln Phe Gln Arg Ser Thr Asp Leu Leu
1               5                   10                  15

Leu Gln Lys Ala Pro Phe Gln Arg Leu Val Arg Glu Val Ser Gly Ala
            20                  25                  30

Gln Lys Glu Gly
        35

<210> SEQ ID NO 11
<211> LENGTH: 33
<212> TYPE: PRT
<213> ORGANISM: Artificial Sequence
<220> FEATURE:
<223> OTHER INFORMATION: Peptide fragment from Trypanosoma cruzi AGP2b2

<400> SEQUENCE: 11
```

```
Gly Asp Lys Ile His Ala Ser Ser Pro Pro Leu Ile Ala Asp Asp Gly
1               5                   10                  15

Gly Lys Leu His Val Asn Leu Ser Arg Ile Phe Thr Ser Thr Leu Gln
            20                  25                  30

Arg

<210> SEQ ID NO 12
<211> LENGTH: 31
<212> TYPE: PRT
<213> ORGANISM: Artificial Sequence
<220> FEATURE:
<223> OTHER INFORMATION: Peptide fragment from Trypanosoma cruzi

<400> SEQUENCE: 12

Met Leu Leu Glu Met Asp Asn Gly Glu Ile Leu Asn Leu Leu Asp Thr
1               5                   10                  15

Pro Gly Leu Leu Asp Ala Lys Val Gln Glu Ala Leu Glu Val Leu
            20                  25                  30
```